(12) United States Patent
Nonaka et al.

(10) Patent No.: US 8,886,936 B2
(45) Date of Patent: Nov. 11, 2014

(54) HEALTH CARE SYSTEM

(75) Inventors: Masao Nonaka, Osaka (JP); Natsume Matsuzaki, Osaka (JP); Hideki Matsushima, Osaka (JP); Yuichi Futa, Osaka (JP)

(73) Assignee: Panasonic Corporation, Osaka (JP)

( * ) Notice: Subject to any disclaimer, the term of this patent is extended or adjusted under 35 U.S.C. 154(b) by 120 days.

(21) Appl. No.: 13/201,062

(22) PCT Filed: Mar. 30, 2010

(86) PCT No.: PCT/JP2010/002296
§ 371 (c)(1),
(2), (4) Date: Aug. 11, 2011

(87) PCT Pub. No.: WO2010/116678
PCT Pub. Date: Oct. 14, 2010

(65) Prior Publication Data
US 2011/0314280 A1 Dec. 22, 2011

(30) Foreign Application Priority Data
Mar. 30, 2009 (JP) ................. 2009-083662

(51) Int. Cl.
*H04L 29/06* (2006.01)
*H04L 9/08* (2006.01)
*A61B 5/00* (2006.01)

(52) U.S. Cl.
CPC ............ *A61B 5/0002* (2013.01); *H04L 9/0866* (2013.01); *H04L 9/0822* (2013.01); *H04L 9/085* (2013.01)
USPC ........................................... 713/168; 380/44

(58) Field of Classification Search
CPC ............... A61B 5/0002; H04L 9/085
USPC ......................................................... 713/168
See application file for complete search history.

(56) References Cited

U.S. PATENT DOCUMENTS

| 2002/0106086 A1 | 8/2002 | Kamiya et al. |
| 2006/0005258 A1 | 1/2006 | Hirose |

(Continued)

FOREIGN PATENT DOCUMENTS

| CN | 1353849 | 6/2002 |
| CN | 1638326 | 7/2005 |

(Continued)

OTHER PUBLICATIONS

International Search Report issued May 11, 2010 in corresponding International Application No. PCT/JP2010/002296.

(Continued)

*Primary Examiner* — Vu Le
*Assistant Examiner* — Tracy Mangialaschi
(74) *Attorney, Agent, or Firm* — Wenderoth, Lind & Ponack, L.L.P.

(57) ABSTRACT

A measurement device measures vital data, encrypts the vital data using an encryption key to generate encrypted vital data, and generates, from a decryption key of the vital data, two pairs of a first share FSD and a second share SSD which enable reproduction of the decryption key. The measurement device generates an encrypted second share by encrypting the second share SSD. The measurement device transmits the encrypted vital data, the first share FSD, and the encrypted second share to a server device via an intermediate device.

21 Claims, 102 Drawing Sheets

(56) References Cited

U.S. PATENT DOCUMENTS

| | | |
|---|---|---|
| 2007/0180259 A1* | 8/2007 | Bulot et al. .................. 713/183 |
| 2007/0239615 A1 | 10/2007 | Matsuzaki et al. |
| 2008/0097908 A1* | 4/2008 | Dicks et al. .................. 705/50 |
| 2009/0125084 A1* | 5/2009 | Juels et al. .................. 607/60 |
| 2009/0222658 A1* | 9/2009 | Sandhu et al. .................. 713/156 |
| 2011/0022851 A1 | 1/2011 | Yokota et al. |

FOREIGN PATENT DOCUMENTS

| | | |
|---|---|---|
| JP | 2002-261746 | 9/2002 |
| JP | 2003-348065 | 12/2003 |
| JP | 2006-127161 | 5/2006 |
| JP | 2008-132101 | 6/2008 |
| JP | 2008-136778 | 6/2008 |
| WO | 00/72286 | 11/2000 |
| WO | 2005/104430 | 11/2005 |
| WO | 2009/119079 | 10/2009 |

OTHER PUBLICATIONS

Bruce Schneier, "Applied Cryptography", Second Edition, John Wiley & Sons, Inc., 1996, pp. 528-529.

Tatsuaki Okamoto et al., "Gendai Ango (Modern Cryptography)", Sangyo Tosho Publishing Co., 1997, pp. 214-215 (with English translation).

Chinese Search Report (in English) dated Aug. 5, 2013 in Chinese Application No. 201080011249.2.

* cited by examiner

Case where threshold value is 3

Fig. 94

| Key identifier | Encryption key | Decryption key | Valid period |
|---|---|---|---|
| 001-01 /220a | A59··· /221a | 625··· /222a | 2008/8 /223a |
| 001-02 /220b | 249··· /221b | DA2··· /222b | 2008/9 /223b |
| 001-03 /220c | 82A··· /221c | 73A··· /222c | 2008/10 /223c |

/172

HEALTH CARE SYSTEM

BACKGROUND OF INVENTION

1. Technical Field

The present invention relates to a health care system capable of protecting confidentiality of vital data such as the weight and blood pressure of a patient measured using measurement devices.

2. Background Art

Recent years have seen a rapidly aging society with an increase in the number of patients who need to take medical treatment (such as consultation and surgery). However, on the other hand, due to reduction in medical expenses, the numbers of doctors and hospital beds have not been increased especially in the rural areas. For this reason, it is predicted that, in the future, the hospital sides will try to reduce the hospitalization periods of patients as much as possible because the hospital sides will become short of the hospital beds with respect to an increasing number of patients. A countermeasure specifically conceivable in view of this is home care in the homes of the patients. In such a case, the use of the following health care system can be considered. First, a patient leases, from a hospital, various kinds of measurement devices for measuring vital data such as weight, blood pressure, and body composition. The patient measures his or her vital data everyday using these devices, and accumulates the measured vital data in the devices. A nursing staff member dispatched from the hospital periodically visits the patient's home, collects the vital data accumulated in the measurement devices, and registers the collected vital data in a server device managed by the hospital. At the same time, the nursing staff member gives the patient guidance and advice relating to the health of the patient based on the collected vital data. Furthermore, a doctor in charge checks the vital data registered in the server and gives the nursing staff member appropriate instructions as necessary. Providing such home care services makes it possible to reduce the hospitalization periods of patients in the hospital, which solves the problem of a lack of the hospital beds.

From the standpoint of the patient, the vital data is private information. Thus, it is essential that a countermeasure against the leakage of the private information is taken. For example, the nursing staff member may lose the information terminal in which the vital data obtained from the patient is recorded. One of conceivable countermeasures against such a threat is to encrypt the measured patient's vital data in such a manner that the server device that is the destination of the vital data can decrypt the vital data. More specifically, each of the measurement devices and the server device shares a secret key in advance, the measurement device encrypts the vital data using the secret key and transmits the encrypted vital data to the server device, and the server device decrypts the vital data into the original vital data using the shared secret key. This eliminates the possibility that the vital data is exposed to a third party when the nursing staff member who receives and passes the vital data loses the information terminal that has been held.

However, in the case where the measurement device encrypts and transmits the vital data using the secret key shared with the server device as described above, the vital data cannot be decrypted using the information terminal held by the nursing staff member because the information terminal does not store the secret key. For this reason, the nursing staff member cannot refer to the vital data of the patient using the information terminal. This is inconvenient for the nursing staff member. However, allowing the nursing staff member to always refer to the patient's vital data using the information terminal may result in the exposure of the vital data to a third party if the information terminal is lost. One of known techniques for satisfying the two demands of the convenience for the operator and the confidentiality of the confidential data is a system using a secret sharing scheme as disclosed in Patent Literature (PTL) 1. Constituent devices of the system hold mutually different shares. It is possible to obtain secret information by combining the shares although none of the constituent devices can obtain the secret information independently. According to the secret sharing scheme, it is possible to configure a system which allows obtainment of secret information when an information terminal held by a nursing staff member and a measurement device held by a patient are present at a same place and does not allow the information terminal held by the nursing staff member to obtain the secret information independently. The system can satisfy the aforementioned two demands.

CITATION LIST

Patent Literature

[PTL 1]
Japanese Laid-open Patent Application Publication No. 2003-348065

SUMMARY OF INVENTION

Patent Literature 1 discloses a technique relating to how to distribute shares and how to reconstruct secret information in a situation where constituent devices of such a system can directly communicate with each other.

However, when there is a plurality of devices, one of the devices may not able to directly communicate with another one of the devices. For example, in the aforementioned case, each of the measurement devices held by the patient cannot directly communicate with the server device held by the hospital. More specifically, each of the measurement devices and the server device can communicate with the same information terminal held by the nursing staff member, but the transmission of the shares from the measurement device to the server device is performed via the information terminal held by the nursing staff member. At this time, in the case where the nursing staff member loses the information terminal, the shares may be exposed to the third party.

The present invention has been conceived in view of the aforementioned problem, and has an object to provide a health care system which allows secure distribution of shares even when each of measurement devices cannot directly transmit the shares to a server device.

In order to achieve the afore-mentioned object, a health care system according to an aspect of the present invention is a health care system for measuring vital data, including: a measurement device which measures the vital data; a server device which collects the vital data; and an intermediate device which receives the vital data from the measurement device, and transmits the received vital data to the server device, wherein the measurement device includes: a measurement unit configured to measure the vital data of a patient; a vital data encryption unit configured to encrypt the vital data using a predetermined encryption key to generate encrypted vital data; a share generation unit configured to generate a first share and a second share from a decryption key for decrypting the encrypted vital data, the first share and the second share being two mutually different shares which enable reconstruction of the decryption key only when both of the two shares are available; a second share encryption unit configured to generate an encrypted second share by encrypting the second share generated by the share generation unit using an encryption key corresponding to a decryption key stored in the server device; and a first communication unit configured to transmit, to the intermediate device, the encrypted vital data generated by the vital data encryption unit, the first share generated by the share generation unit, and the encrypted second share generated by the second share encryption unit, the intermediate device includes: a second communication unit configured to receive, from the measurement device, the encrypted vital data, the first share, and the encrypted second share; and a third communication unit configured to transmit, to the server device, the encrypted vital data, the first share, and the encrypted second share received by the second communication unit, and the server device includes: a fourth communication unit configured to receive, from the intermediate device, the encrypted vital data, the first share, and the encrypted second share; a share decryption unit configured to decrypt the encrypted second share received by the fourth communication unit using the decryption key stored in the server device, to generate the second share; a reconstruction unit configured to reconstruct the decryption key for decrypting the encrypted vital data using the first share received by the fourth communication unit and the second share generated by the share decryption unit; and a vital data decryption unit configured to decrypt the encrypted vital data received by the fourth communication unit, using the decryption key reconstructed by the reconstruction unit, to generate the vital data.

With this structure, the first share and the second share are generated from the decryption key corresponding to the encryption key used to encrypt the measured vital data. The second share is encrypted using the encryption key corresponding to the decryption key stored in the server device, and, together with the first share, the encrypted second share is transmitted to the server device via the intermediate device. Since the encrypted second share can be decrypted only by the server device, the decryption key can be reconstructed only when both of the first share and the second share are available. Thus, the intermediate device which stores the first share and the encrypted second share cannot reconstruct the decryption key. On the other hand, the server device is capable of generating the second share by decrypting the encrypted second share, and reconstructing the decryption key from the first share and the second share. Therefore, the server device is capable of decrypting the encrypted vital data using the decryption key. Accordingly, even if the intermediate device is lost, it is impossible for a third party to decrypt the decryption key. Accordingly, it is possible to securely distribute the share even when it is impossible to directly transmit the share from the measurement device to the server device.

Preferably, the first communication unit be further configured to transmit the second share to the intermediate device, the second communication unit be further configured to receive the second share from the measurement device, the intermediate device further include: a storage unit configured to store only the first share received by the second communication unit; an intermediate device side vital data decryption unit configured to reconstruct the decryption key for decrypting the encrypted vital data using the first share stored in the storage unit and the second share received by the second communication unit, and decrypt the encrypted vital data received by the second communication unit using the reconstructed decryption key, to generate the vital data; and a display unit configured to display the vital data generated by the intermediate device side vital data decryption unit.

With this structure, the intermediate device stores only the first share. Thus, the intermediate device can reconstruct the decryption key when both of the first share and the second share become available when the second share is received from the measurement device. Therefore, the intermediate device is capable of decrypting the encrypted vital data using the decryption key, and displaying the vital data on the display unit. Since the intermediate device stores only the first share, the intermediate device is capable of displaying the vital data only when the second share is received from the measurement device. For this reason, it becomes possible to display the vital data on the display unit only when both of the measurement device and the intermediate device are available. Accordingly, it is impossible to check the vital data using only the intermediate device. Therefore, it is possible to prevent the vital data from being seen by a third party at a place unknown by the patient who is the user of the measurement device.

In addition, it is possible to prevent leakage of the vital data to the outside even when the intermediate device is lost because it is impossible for a third party to display the vital data on the display unit of the intermediate device when the measurement device and the intermediate device are not present at a same place.

Furthermore, the use of the technique of the secret sharing scheme makes it possible to completely prevent the risk of leakage of the secret.

More preferably, the health care system further include an access device which receives the vital data from the intermediate device, and transmits the received vital data to the server device, wherein the share generation unit be configured to generate a third share from the decryption key for decrypting the encrypted vital data, wherein the first share, the second share, and the third share be different from each other and enable reconstruction of the decryption key when selected as two shares available for the reconstruction, the measurement device further include a third share encryption unit configured to encrypt the third share generated by the share generation unit using an encryption key corresponding to a decryption key stored in the access device, to generate an encrypted third share, the first communication unit further transmit the encrypted third share to the intermediate device, the second communication unit further receive the encrypted third share from the measurement device, the third communication unit transmit, to the access device, the encrypted vital data, the first share, the encrypted second share, and the encrypted third share received by the second communication unit, the access device include: a fifth communication unit configured to receive, from the intermediate device, the encrypted vital data, the first share, the encrypted second share, and the encrypted third share; a third share decryption unit configured to decrypt the encrypted third share received by the fifth communication unit using the decryption key stored in the access device, to generate the third share; and a sixth communication unit configured to transmit, to the server device, the encrypted vital data, the first share, the encrypted second share received by the fifth communication unit, and the fourth communication unit is configured to receive, from the access unit, the encrypted vital data, the first share, and the encrypted second share.

The third share is encrypted by the measurement device, and is transmitted as the encrypted third share to the intermediate device. However, the encrypted third share can be decrypted only by the access device. For this reason, the intermediate device cannot independently obtain the two shares. Furthermore, the first share is encrypted by the intermediate device, and is transmitted as the second encrypted first share to the access device. Although the encrypted third share can be decrypted by the access device, the second encrypted first share can be decrypted only by the server device. For this reason, the access device cannot independently obtain the two shares. Accordingly, even if either the intermediate device or the access device is lost, it is impossible for a third party to reconstruct the decryption key. Accordingly, it is possible to securely distribute the share even when it is impossible to directly transmit the share from the measurement device to the server device.

Furthermore, since the intermediate device stores the first share and the access device stores the third share, the two shares are available when both the devices are present at a same place. This enables the reconstruction of the decryption key. Therefore, the intermediate device is capable of decrypting the encrypted vital data using the decryption key, and displaying the vital data on the display unit.

More preferably, the server device further include: a holding unit configured to hold the second share; and a supply unit configured to supply the second share held in the holding unit to an other measurement device having the same structure as a structure of the measurement device.

With this structure, even if the second share stored in the measurement device is lost due to a loss or a trouble of the measurement device, a supply of the second share from the sever device to another measurement device makes it possible to obtain the second share using the other measurement device. For this reason, it is possible to decrypt the encrypted vital data using the other measurement device as long as the first share stored in the intermediate device is also used.

Alternatively, the server device may further include: a holding unit configured to hold the first share; and a supply unit configured to supply the first share held in the holding unit to an other intermediate device having the same structure as a structure of the intermediate device.

With this structure, even if the first share stored in the intermediate device is lost due to a loss or a trouble of the intermediate device, a supply of the first share from the sever device to another intermediate device makes it possible to obtain the first share using the other intermediate device. For this reason, it is possible to decrypt the encrypted vital data using the other intermediate device as long as the second share stored in the measurement device is also used.

Alternatively, the server device may further include a supply unit configured to generate, from the decryption key reconstructed by the reconstruction unit, a share associated with an other measurement device having the same structure as a structure of the measurement device, and supply the generated share to the other measurement device, the supplied share being different from the first share and the second share.

With this structure, even if the second share stored in the measurement device is lost due to a loss or a trouble of the measurement device, a supply of the share from the sever device to another measurement device makes it possible to obtain the share using the other measurement device. For this reason, it is possible to decrypt the encrypted vital data using the other measurement device as long as the first share stored in the intermediate device is also used. Furthermore, the share that is supplied from the server device is different from the first share and the second share, and is associated with the other measurement device. For this reason, if the shares leak from the other measurement device to the outside, it is possible to identify the measurement device as the source of the shares.

Alternatively, the server device may further include a supply unit configured to generate, from the decryption key reconstructed by the reconstruction unit, a share associated with an other intermediate device having the same structure as a structure of the intermediate device, and supply the generated share to the other intermediate device, the supplied share being different from the first share and the second share.

With this structure, even if the first share stored in the intermediate device is lost due to a loss or a trouble of the intermediate device, a supply of the share from the sever device to the other intermediate device makes it possible to obtain the share using the other intermediate device. For this reason, it is possible to decrypt the encrypted vital data using the other intermediate device as long as the second share stored in the measurement device is also used. Furthermore, the share that is supplied from the server device is different from the first share and the second share, and is associated with the other intermediate device. For this reason, if the shares leak from the other intermediate device to the outside, it is possible to identify the intermediate device as the source of the shares.

Alternatively, the measurement device may include a measurement terminal and a management terminal, the measurement terminal may include: the measurement unit; the vital data encryption unit; the share generation unit; the first share encryption unit; and a transmission unit configured to transmit, to the management terminal, the encrypted vital data, the encrypted first share, and the second share, the management terminal may include: a reception unit configured to receive, from the measurement terminal, the encrypted vital data, the encrypted first share, and the second share; a second share encryption unit; and a first communication unit, and the second share encryption unit may be configured to encrypt the second share received by the reception unit using an encryption key corresponding to the decryption key stored in the server device, to generate the encrypted second share.

With this structure, the measurement device is separated as the measurement terminal and the management terminal, and the first share and the second share are encrypted by the measurement terminal and the management terminal, respectively. In this way, separately encrypting the two shares using the terminals makes it difficult to reconstruct the shares in the case where a leakage to the outside occurs.

It is to be noted that the present invention can be implemented not only as a health care system including the above-described unique processing units, but also a vital data measurement method including the steps corresponding to the processing executed by the unique processing units included in the health care system, and also a program causing a computer to execute the unique steps of the vital data measurement method. Naturally, the program can be distributed via non-volatile computer-readable recording media such as Compact Disc-Read Only Memories (CD-ROMs) and communication networks such as the Internet.

The present invention provides a health care system that enables secure distribution of share even when it is impossible to directly transmit the share from a measurement device to a server device.

BRIEF DESCRIPTION OF DRAWINGS

FIG. 94 is a diagram showing a structure of an encryption key DB in (3) of Variation.

DETAILED DESCRIPTION OF INVENTION

Embodiment 1

Hereinafter, Embodiment 1 of the present invention will be described with reference to the drawings.

Figure 1:
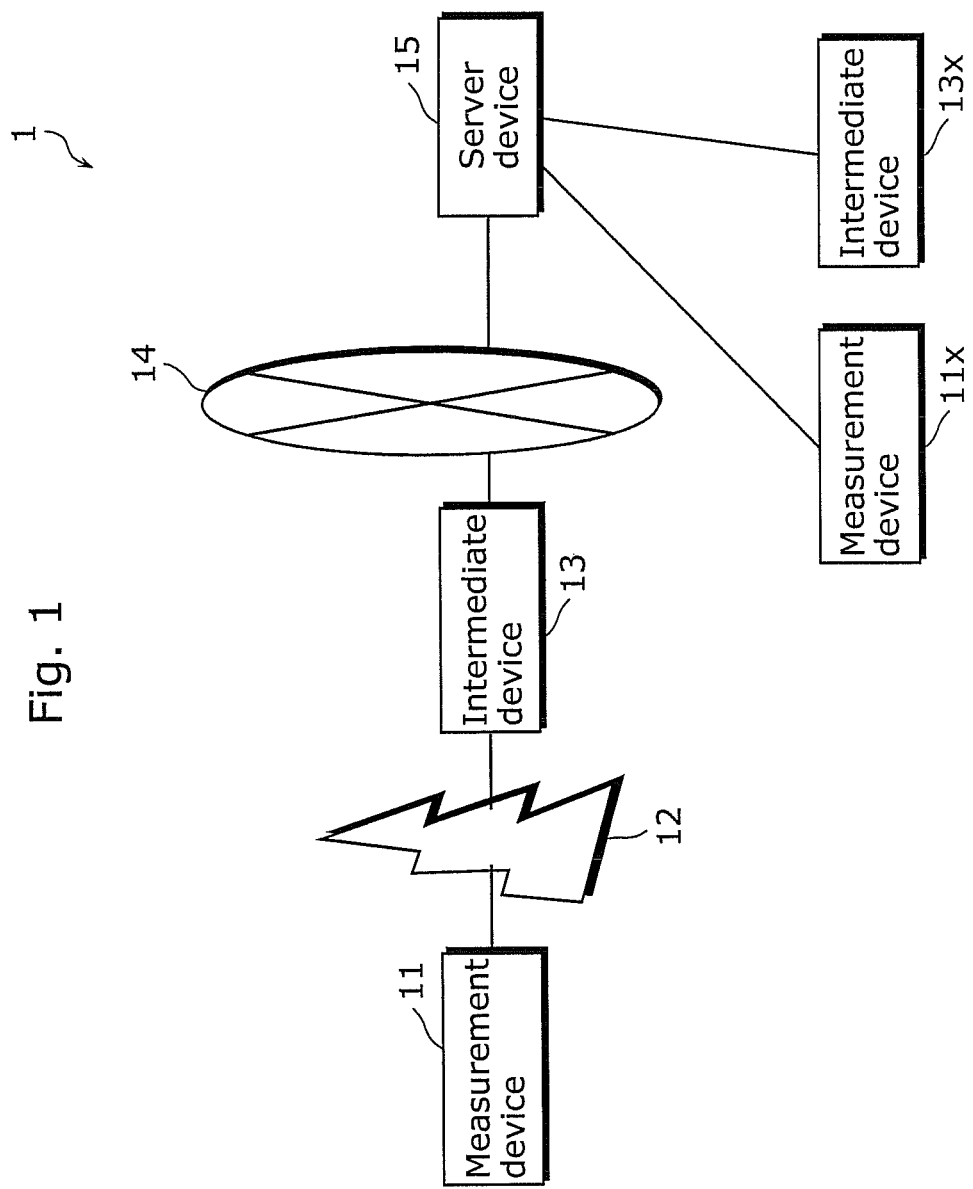
FIG. 1 is a block diagram showing a structure of a health care system according to Embodiment 1 of the present invention.

FIG. 1 is a diagram showing a structure of a health care system 1.

The health care system 1 includes a measurement device 11, an intermediate device 13, and a server device 15. The measurement device 11 and the intermediate device 13 are connected via a first computer network 12, and the intermediate device 13 and the server device 15 are connected via a second computer network 14. The measurement device 11 is a device held by a patient, and has a function for measuring vital data such as a body temperature of the patient. The intermediate device 13 is a device held by a nursing staff member, and takes a role for receiving the vital data measured by the measurement device 11 and passing the vital data to the server device 15. In addition, the intermediate device 13 has a function for allowing the nursing staff member to browse past vital data of the patient when the nursing staff visits the patient's home. In this way, the nursing staff member can give the patient suitable advice. The sever device 15 is a device managed by a hospital, and manages the patient's vital data collected from the measurement device 11 via the intermediate device 13. The vital data managed here is browsed by a doctor in charge in the hospital.

The first computer network 12 and the second computer network 14 are described first, and then the structures of the measurement device 11, the intermediate device 13, and the server device 15 are described with reference to the drawings.

[Structure of First Computer Network 12]

The first computer network 12 is a computer network for transmission and reception of various kinds of data between the measurement device 11 and the intermediate device 13. Examples of the first computer network 12 include a computer network for wireless connection that is established by Bluetooth (trademark) etc., and a computer network for wired connection that is established using a Universal Serial Bus (USB) etc.

[Structure of Second Computer Network 14]

The second computer network 14 is a computer network for transmission and reception of various kinds of data between the intermediate device 13 and the server device 15. For example, the second computer network 14 is established by the Asymmetric Digital Subscriber Line (ADSL), a telephone line, a dedicated line, or the like.

[Structure of Measurement Device 11]

Next, the structure of the measurement device 11 is described.

Figure 2:
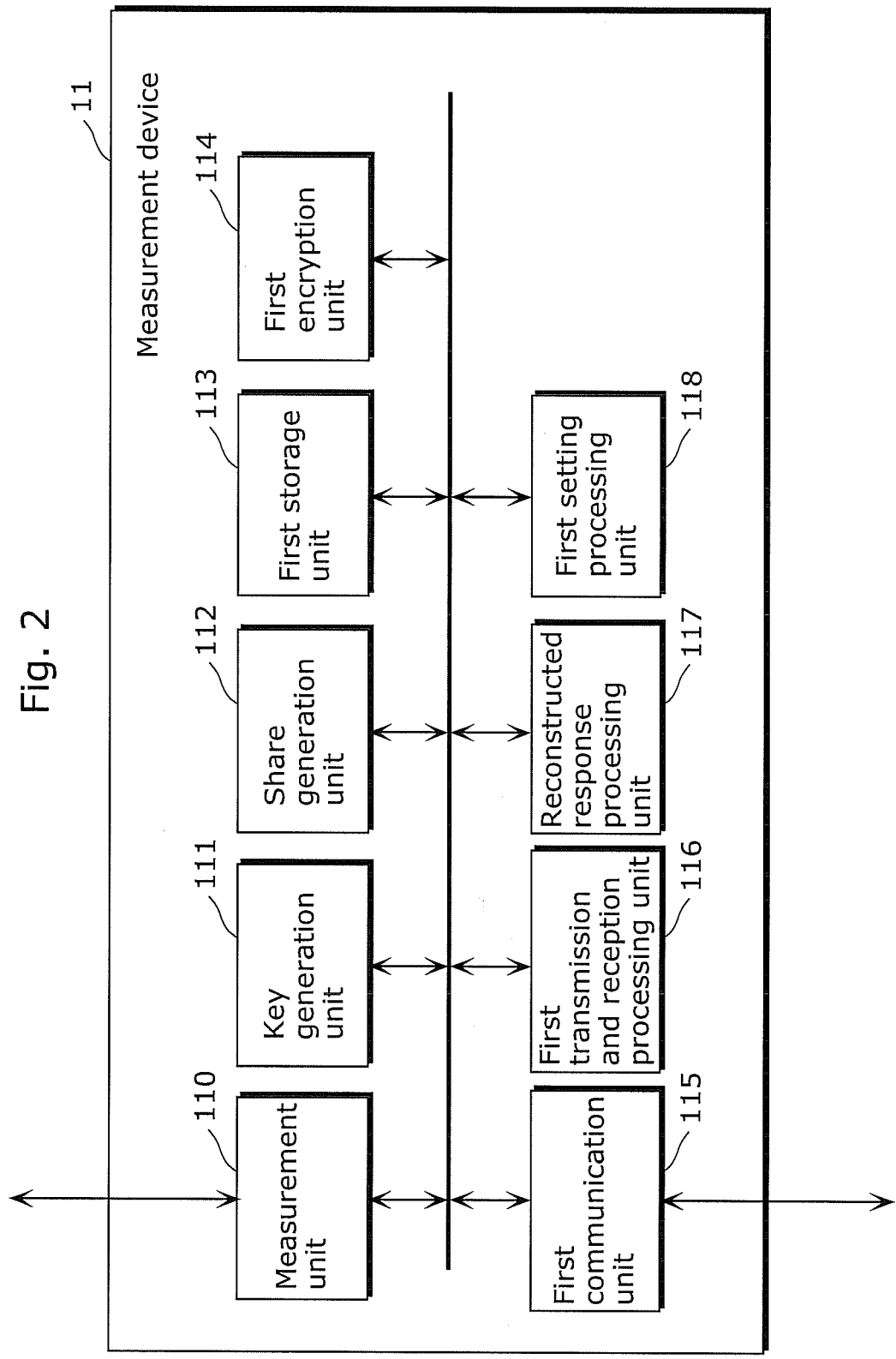
FIG. 2 is a block diagram showing a structure of a measurement device.

FIG. 2 is a block diagram showing a structure of the measurement device 11. As shown in FIG. 2, the measurement device 11 includes a measurement unit 110, a key generation unit 111, a share generation unit 112, a first storage unit 113, a first encryption unit 114, a first communication unit 115, a first transmission and reception processing unit 116, a reconstructed response processing unit 117, and a first setting processing unit 118. Among these structural elements, the essential structural elements are the measurement unit 110, the share generation unit 112, the first encryption unit 114, and the first communication unit 115.

It is to be noted that the measurement unit 110, the share generation unit 112, and the first communication unit 115 are respectively correspond to a measurement unit, a share generation unit, and a first communication unit in the CLAIMS of the present application. In addition, the first encryption unit 114 corresponds to a vital data encryption unit, a first share encryption unit, and a second share encryption unit in the CLAIMS of the present application.

(1) Measurement Unit 110

The measurement unit 110 measures vital data VD of a patient. Examples of vital data VD include weight, body fat, body temperature, blood pressure, blood sugar level, pulse, heart beat, the number of steps taken, and activities quantity. In the case where the vital data VD is the body temperature, the data size of the vital data VD is 3 bytes (1 byte for each of the tens place, ones place, and tenths place). The measurement device 11 includes a "measure button", and the measurement unit 110 has a function for measuring vital data VD when the button is pressed. It is to be noted that the measurement unit 110 has a clock function, and may add the measurement time to the vital data VD. As an example, when the body temperature measured at 11:26 on Oct. 16, 2008 is 36.5 degrees Celsius, the vital data VD is "10/16/2008 11:26 365". The measurement unit 110 outputs the generated vital data VD to another one of the functional blocks.

(2) Key Generation Unit 111

The key generation unit 111 generates an encryption key PK and a decryption key SK that are a pair of keys in public key encryption, when the encryption key PK and the decryption key SK are not set in the encryption key DB in the first storage unit 113. The public key encryption is, for example, Rivest Shamir Adleman (RSA) scheme, the elliptic curve cryptography scheme, or the like. The RSA scheme, the elliptic curve cryptography scheme, and the key generation methods according to the schemes are publicly known, thus no detailed descriptions are given here. The key generation unit 111 stores the encryption key PK and the decryption key SK into the encryption key DB in the first storage unit 113. For example, the key generation unit 111 may generate the encryption key PK and the decryption key SK when the measurement device 11 is firstly activated, or may generate these keys when the vital data VD is firstly measured by the measurement unit 110. It is to be noted that the key generation unit 111 may not always be included in the measurement device 11. In other words, the measurement device 11 may receive the encryption key PK and the decryption key SK from a device outside the measurement device 11.

(3) Share Generation Unit 112

After the key generation unit 111 generates the pair of keys, the share generation unit 112 generates two mutually different shares from the decryption key SK that is set in the encryption key DB in the first storage unit 113 according to the secret sharing scheme. The secret sharing scheme is an approach of dividing data into n number of data and allowing the reconstruction of the original data when k number of mutually different data among the n number of data are available. Here, each of k and n is a natural number, and k≤n is satisfied.

Non Patent Literature

[NPL 1]
"APPLIED CRYPTOGRAPHY Second edition", Bruce Schneier, WILEY, 1996, PP 528-529

[NPL 2]
"*Gendai Ango* (Modern Encryption)", Tatsuaki Okamoto, Hirosuke Yamamoto, Sangyo Tosho Publishing Co., 1997, pp. 214-215

Figure 3:
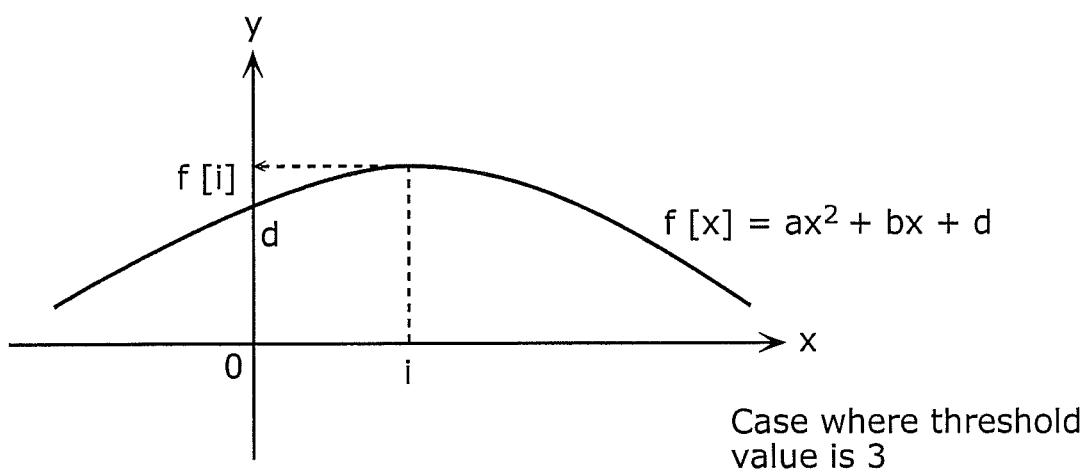
FIG. 3 is an illustration of a secret sharing scheme.

The secret sharing is described in more detail. The secret sharing is an approach for generating, from a secret, a plurality of pieces of information (referred to as a plurality of "shares"), and allowing the reconstruction of the original secret when k number of shares are available. Here, k is a threshold value that is arbitrarily set. The following descriptions are given taking an example case where the threshold value k is 3. With reference to FIG. 3, a quadratic polynomial $f[x]=ax^2+bx+d$ (a and b are arbitrarily determined) is determined assuming that the constant term (the intercept in FIG. 3) is the original secret d. At this time, the i-th share is $f[x]$ where i is set as x in the quadratic polynomial. In other words, the i-th share corresponds to the y-coordinate value when i is set as the x coordinate in the coordinate diagram of FIG. 3. It is to be noted that the quadratic polynomial is determined when the three points on the quadratic polynomial are determined, and the secret d that is the intercept is reconstructed. Although it is assumed here that the share is y-coordinate shown by $f[i]$ corresponding to the number of times of measurement i, the share may be the point (indicated by a pair of the x-coordinate and the y-coordinate) on the quadratic polynomial.

Here, one of the two mutually different shares is referred to as a first share FSD, and the other is referred to as a second share SSD. These shares are used to disable the reconstruction of the decryption key SK when only one of the shares is available, and enables the reconstruction of the decryption key when both of the two shares are available. The first share FSD and the second share SSD are stored in the share DB in the first storage unit 113. At this time, an initial value of a key transmission flag SF is set to "No".

(4) First Storage Unit 113

Figure 4:
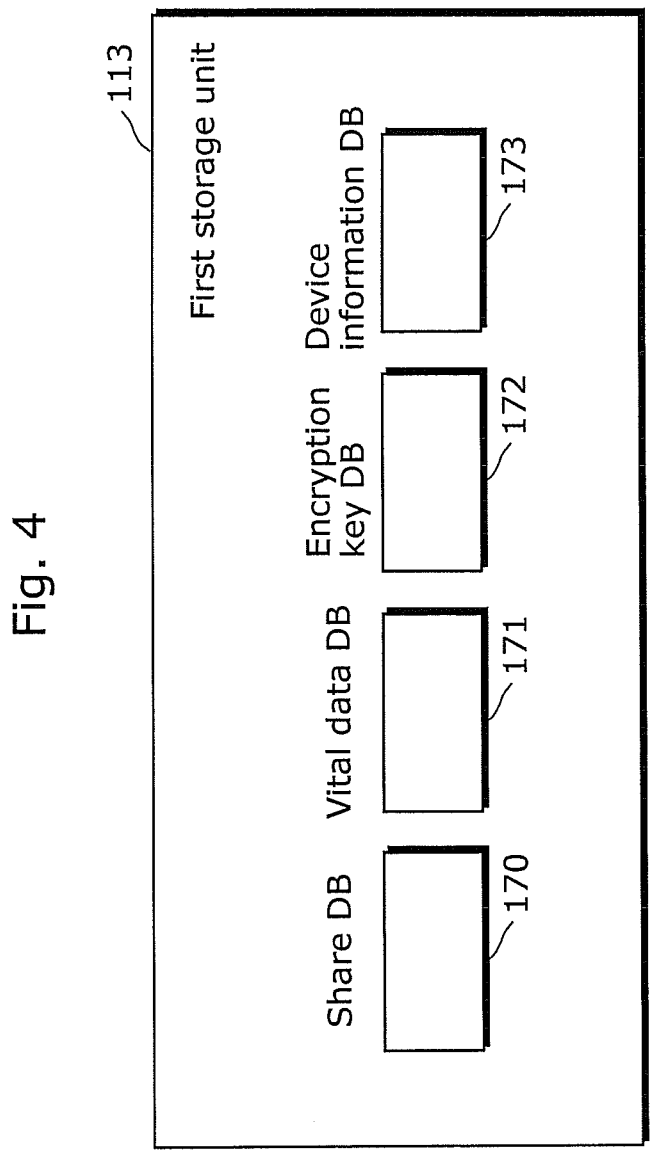
FIG. 4 is a block diagram showing a structure of a first storage unit of the measurement device.

As shown in FIG. 4, the first storage unit 113 holds a share DB 170, a vital data DB 171, an encryption key DB 172, and a device information DB 173.

Figure 5:
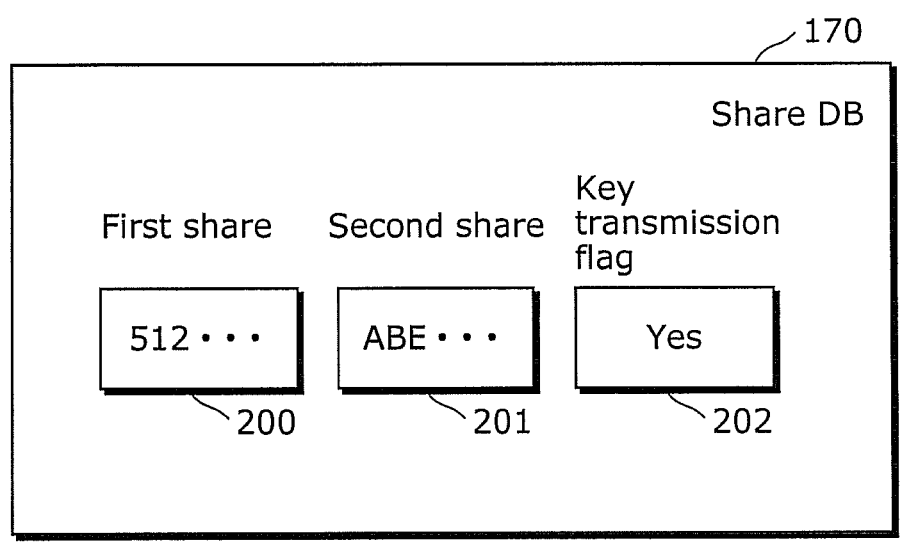
FIG. 5 is a diagram showing a structure of a share DB in the first storage unit of the measurement device.

As shown in FIG. 5, the share DB 170 includes a first share FSD (a first share 200 in FIG. 5), a second share SSD (a second share 201 in FIG. 5), and a key transmission flag SF (a key transmission flag 202 in FIG. 5). Each of the first share FSD and the second share SSD is a value generated when the share generation unit 112 performs sharing on the decryption key SK generated by the key generation unit 111. The key transmission flag SF is a value indicating whether or not each of the first share FSD and the second share SSD is already passed to the intermediate device 13. Here, "Yes" represents "Already transmitted", and "No" represents "Not yet transmitted". The key transmission flag SF is used when the measurement device 11 judges whether or not to transmit the first share FSD and the second share SSD to the intermediate device 13.

Figure 6:
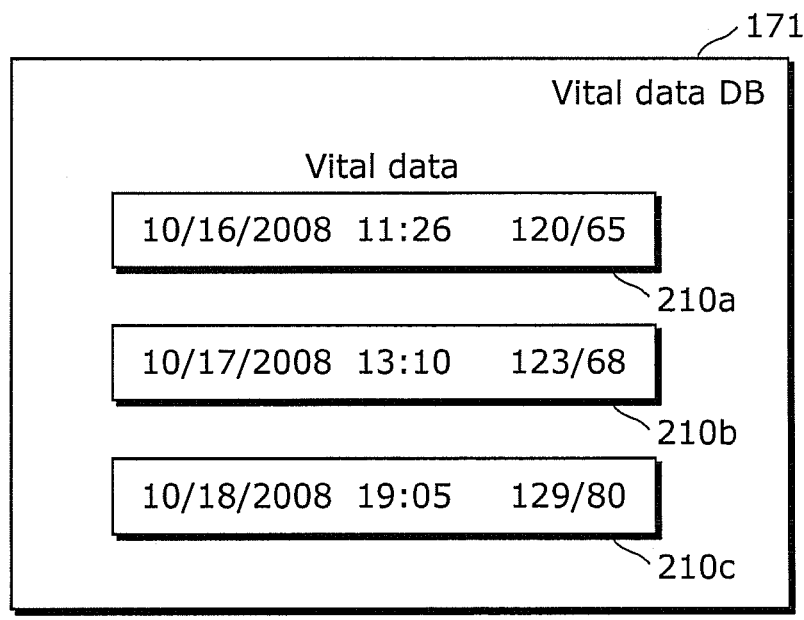
FIG. 6 is a diagram showing a structure of a vital data DB in the first storage unit of the measurement device.

As shown in FIG. 6, the vital data DB 171 includes one or more vital data VD (vital data 210a, 210b, and 210c in FIG. 6). Each of the vital data VD is vital data measured by the measurement unit 110.

Figure 7:
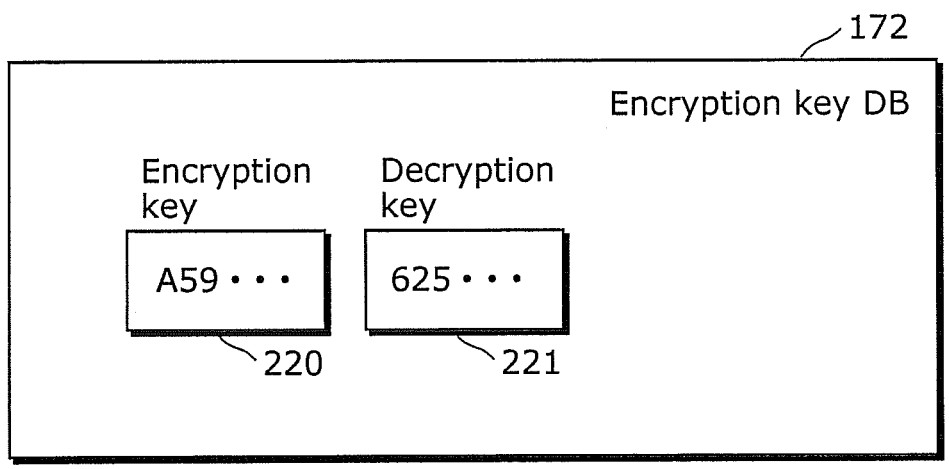
FIG. 7 is a diagram showing a structure of an encryption key DB in the first storage unit of the measurement device.

As shown in FIG. 7, the encryption key DB 172 includes the encryption key PK (an encryption key 220 in FIG. 7) and the decryption key SK (a decryption key 221 in FIG. 7). The encryption key PK and the decryption key SK are generated by the key generation unit 111.

Figure 8:
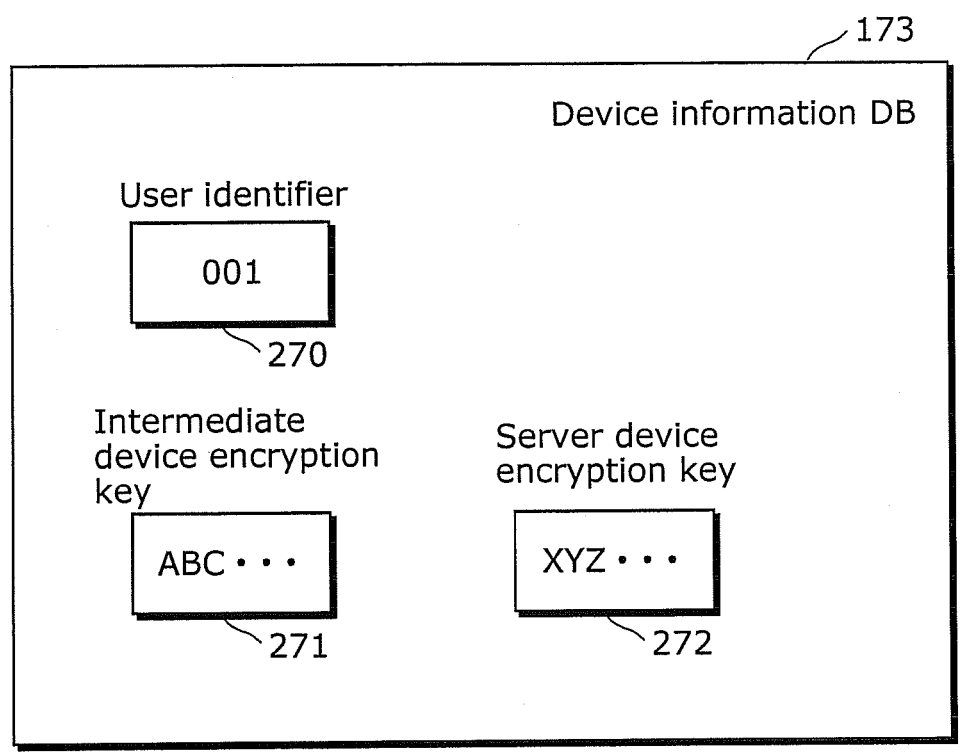
FIG. 8 is a block diagram showing a structure of a device information DB of the first storage unit of the measurement device.

As shown in FIG. 8, the device information DB 173 includes a user identifier ID (a user identifier 270 in FIG. 8), an intermediate device encryption key CPK (an intermediate device encryption key 271 in FIG. 8), and a server device encryption key (a server device encryption key 272 in FIG. 8). The user identifier ID is a number identifying the patient who holds the measurement device 11. The intermediate device encryption key CPK is a key corresponding to the intermediate device decryption key CSK held by the intermediate device 13, and the server device encryption key SPK is a key corresponding to the server device decryption key SSK held by the server device 15.

(5) First Encryption Unit 114

The first encryption unit 114 has the following two functions.

A. Encryption of Vital Data VD

Upon receiving the vital data VD from the one of the functional blocks, the first encryption unit 114 accesses the encryption key DB 172 in the first storage unit 113, and obtains the encryption key PK. Next, the first encryption unit 114 encrypts the vital data VD using the encryption key PK. The vital data VD encrypted is referred to as encrypted vital data EVD. The same encryption scheme as the scheme used by the key generation unit 111 to generate the pair of keys is employed here. For example, the encryption scheme is the RSA scheme or the elliptic curve cryptography scheme. Next, the first encryption unit 114 outputs the encrypted vital data EVD to the one of the functional blocks.

B. Encryption of Shares

Upon receiving the first share FSD and the second share SSD from the one of the functional blocks, the first encryption unit 114 accesses the device information DB 173 in the first storage unit 113, and obtains the intermediate device encryption key CPK. Next, the first encryption unit 114 encrypts the first share FSD using the intermediate device encryption key CPK. Subsequently, the first encryption unit 114 accesses the device information DB 173 in the first storage unit 113, and obtains the server device encryption key SPK. Next, the first encryption unit 114 encrypts the second share SSD using the server device encryption key SPK. The first share FSD encrypted and the second share SSD encrypted are also referred to as an encrypted first share EFSD and an encrypted second share ESSD, respectively. For example, the encryption scheme is the RSA scheme or the elliptic curve cryptography scheme. Next, the first encryption unit 114 outputs the encrypted first share EFSD and the encrypted second share ESSD to the one of the functional blocks.

(6) First Communication Unit 115

The first communication unit 115 has a function for transmitting and receiving various kinds of data to and from the intermediate device 13 via the first computer network 12, in response to the request from the one of the functional blocks.

(7) First Transmission and Reception Processing Unit 116

Figure 9:
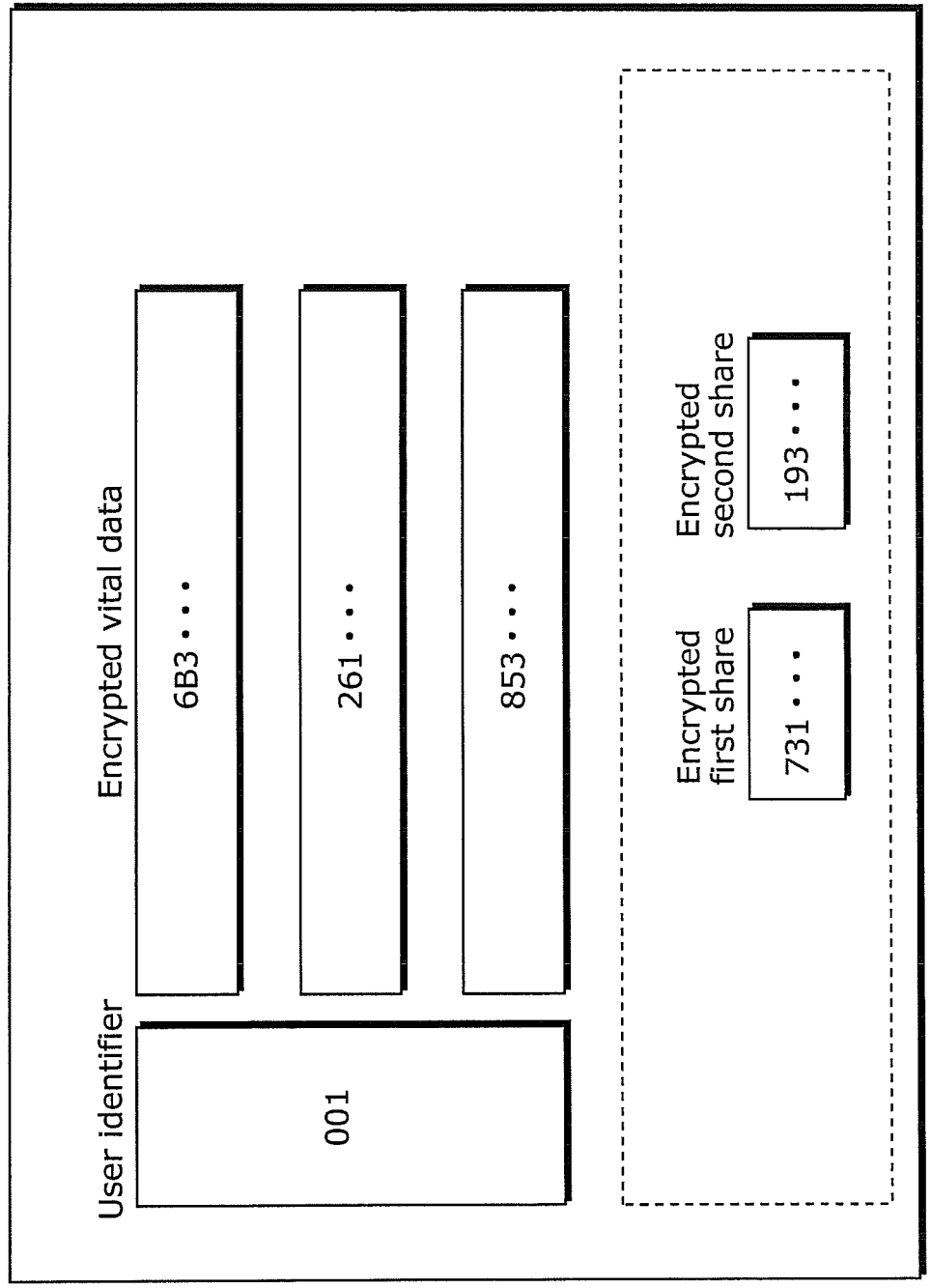
FIG. 9 is a diagram showing a structure of a first data FD.

The first transmission and reception processing unit 116 generates first data FD including a user identifier ID and one or more encrypted vital data EVD as shown in FIG. 9, in response to the request from the outside. For example, the measurement device 11 includes a "transmission button", and the first transmission and reception processing unit 116 generates the first data FD when the button is pressed. The first transmission and reception processing unit 116 obtains the user identifier ID from the device information DB 173 in the first storage unit 113. The encrypted vital data EVD is data that is obtained when the first encryption unit 114 encrypts the vital data VD. In the encryption, when the key transmission flag SF stored in the share DB 170 in the first storage unit 113 indicates "No", the first transmission and reception processing unit 116 makes an additional request to the first encryption unit 114 to generate the encrypted first share EFSD and the encrypted second share ESSD. Next, the first transmission and reception processing unit 116 includes, in the first data FD, the encrypted first share EFSD and the encrypted second share ESSD. Next, the first transmission and reception processing unit 116 transmits the generated first data FD to the intermediate device 13 via the first communication unit 115.

(8) Reconstructed Response Processing Unit 117

When the reconstructed response processing unit 117 receives the user identifier ID from the intermediate device 13 via the first communication unit 115, the reconstructed response processing unit 117 accesses the device information DB 173 in the first storage unit 113 first, and checks whether or not the received user identifier ID is the same as the user identifier ID stored in the device information DB 173. When the both are the same, the reconstructed response processing unit 117 obtains the second share SSD from the share DB 170 in the first storage unit 113, and transmits the second share SSD to the intermediate device 13 via the first communication unit 115.

(9) First Setting Processing Unit 118

The first setting processing unit 118 has a function for setting the user identifier ID, the intermediate device encryption key CPK, and the server device encryption key SPK, to the device information DB 173 in the first storage unit 113, based on the data that is input from the outside. For example, the first setting processing unit 118 may set the pieces of information based on the data that is input using a keyboard, or may be set based on data stored in a memory card such as a Secure Digital (SD) card. In addition, the first setting processing unit 118 includes a predetermined authentication function (such as password authentication), and performs authentication when the measurement device 11 establishes a connection with the server device 15. When the predetermined authentication is successfully performed, the server device 15 is capable of setting the first share FSD, the second share SSD, and the key transmission flag SF, into the share DB 170 in the first storage unit 113 via the first setting processing unit 118.

[Structure of Intermediate Device 13]

Figure 10:
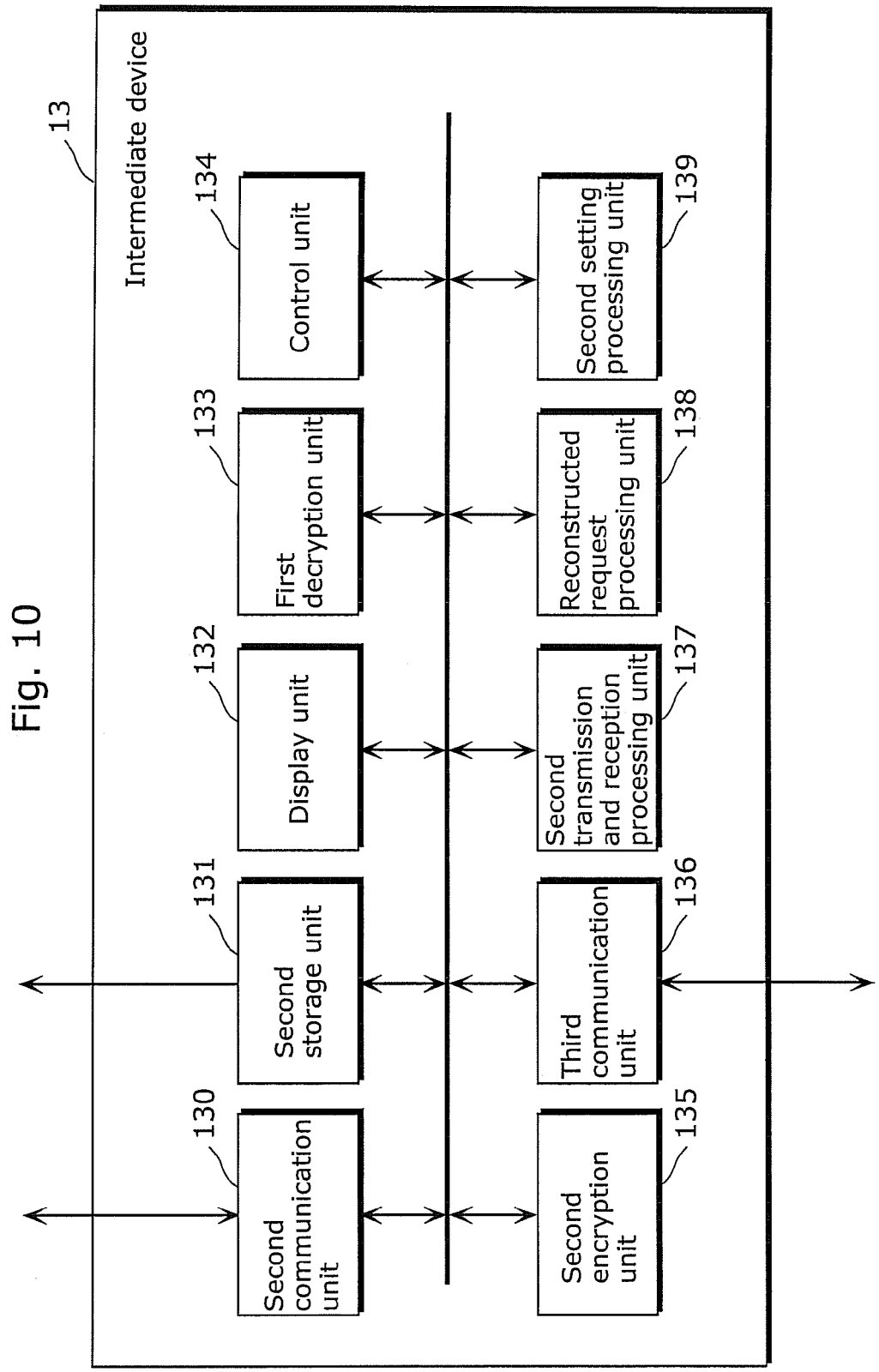
FIG. 10 is a block diagram showing a structure of an intermediate device.

Next, the structure of the intermediate device 13 is described. FIG. 10 is a block diagram showing the structure of the intermediate device 13. As shown in FIG. 10, the intermediate device 13 includes a second communication unit 130, a second storage unit 131, a display unit 132, a first decryption unit 133, a control unit 134, a second encryption unit 135, a third communication unit 136, a second transmission and reception processing unit 137, a reconstructed request processing unit 138, and a second setting processing unit 139. Among the structural elements, the essential elements are the second communication unit 130 and the third communication unit 136.

It is to be noted that the second communication unit 130, the display unit 132, and the third communication unit 136 respectively correspond to a second communication unit, a display unit, and a third communication unit in the CLAIMS of the present application. In addition, the second storage unit 131 corresponds to a storage unit in the CLAIMS of the present application. Furthermore, the first decryption unit 133 corresponds to a vital data decryption unit at the intermediate device side in the CLAIMS of the present application. Furthermore, the second encryption unit 135 corresponds to a first share decryption unit in the CLAIMS of the present application.

(1) Second Communication Unit 130

The second communication unit 130 has a function for transmitting and receiving various kinds of data to and from the measurement device 11 via the first computer network 12.

(2) Second Storage Unit 131

Figure 11:
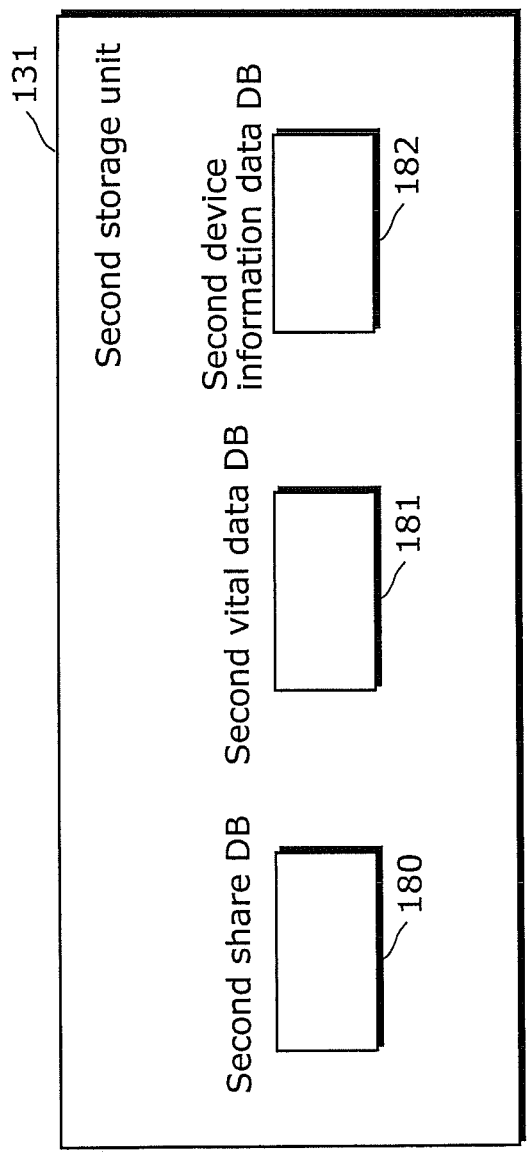
FIG. 11 is a diagram showing a structure of a second storage unit of the intermediate device.

As shown in FIG. 11, the second storage unit 131 holds a second share DB 180, a second vital data DB 181, and a second device information DB 182.

Figure 12:
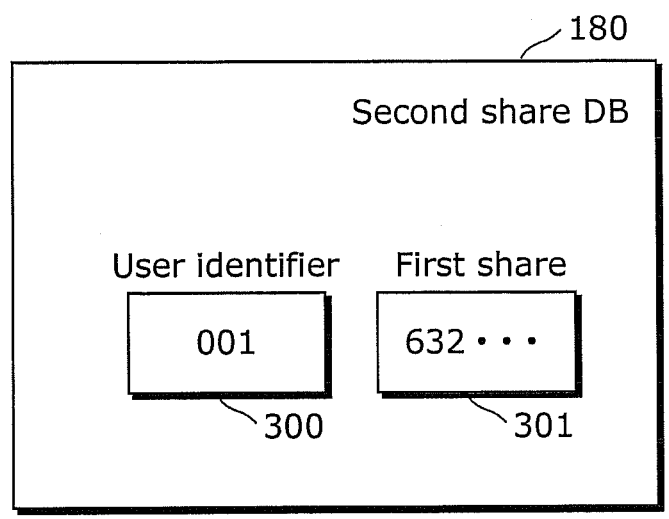
FIG. 12 is a diagram showing a structure of a second share DB in a second storage unit of the intermediate device.

As shown in FIG. 12, the second share DB 180 includes a user identifier ID (a user identifier 300 in FIG. 12) and a first share FSD (a first share 301 in FIG. 12).

Figure 13:
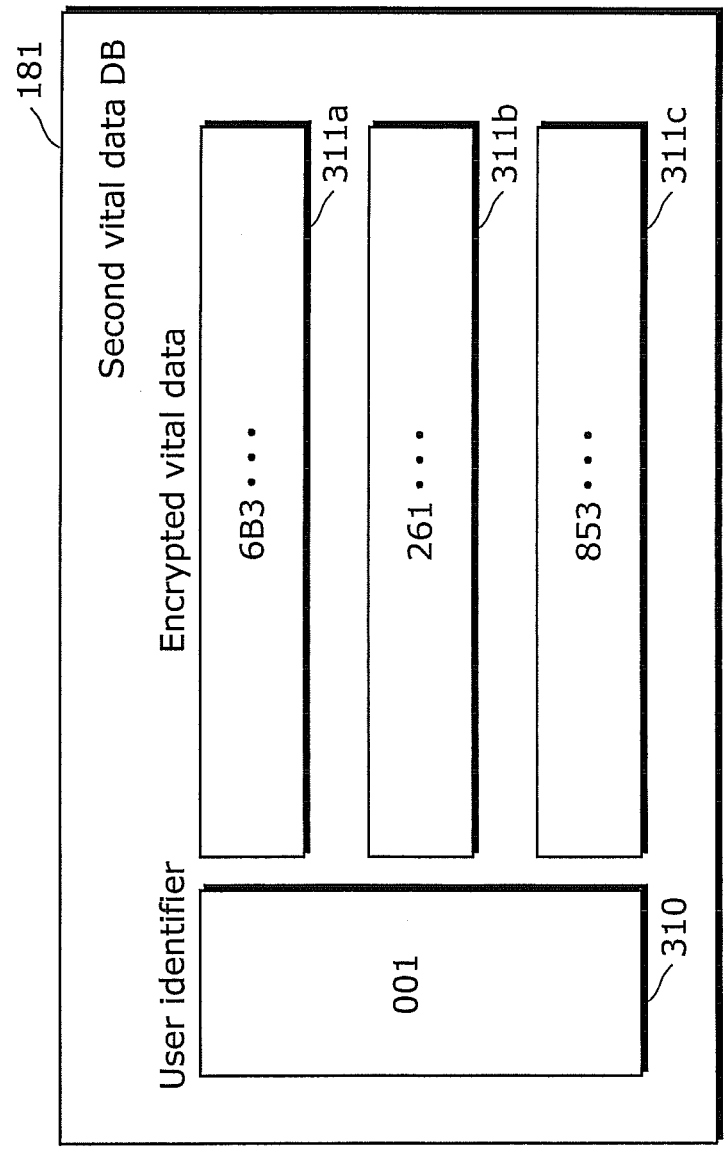
FIG. 13 is a diagram showing a structure of a second vital data DB in a second storage unit of the intermediate device.

As shown in FIG. 13, the second vital data DB 181 includes a user identifier ID (a user identifier 310 in FIG. 13) and one or more encrypted vital data EVD (encrypted vital data 311a, 311b, and 311c).

Figure 14:
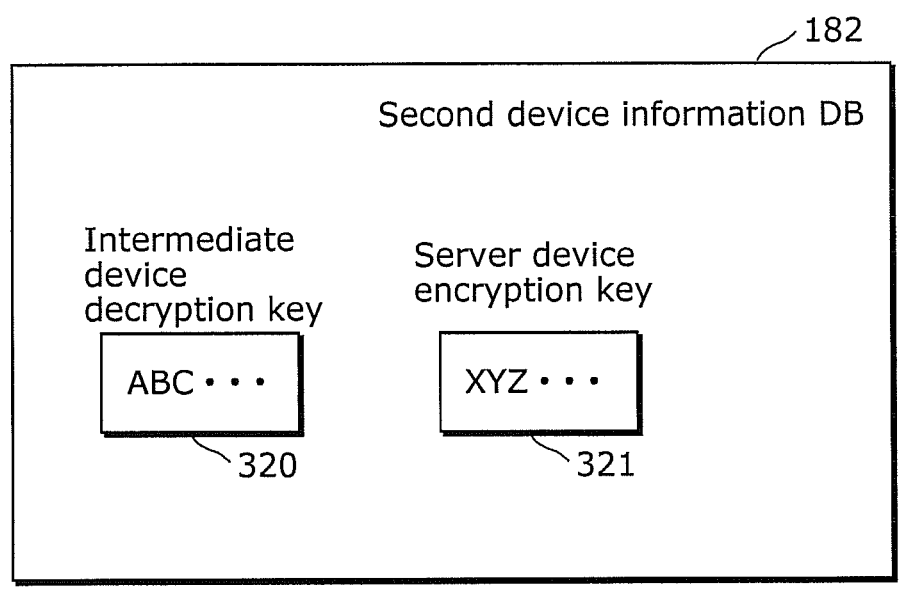
FIG. 14 is a diagram showing a structure of a second device information DB in the second storage unit of the intermediate device.

As shown in FIG. 14, the second device information DB 182 includes an intermediate device decryption key CSK (an intermediate device decryption key 320 in FIG. 14) and a server device encryption key SPK (a server device encryption key 321 in FIG. 14).

(3) Display Unit 132

The display unit 132 has a function for displaying vital data VD. For example, the display unit 132 displays a plurality of vital data VD in the form of a graph or a table.

(4) First Decryption Unit 133

When the first decryption unit 133 receives the first share FSD, the second share SSD, and the encrypted vital data EVD, the first decryption unit 133 firstly reconstructs the decryption key SK from the first share FSD and the second share SSD according to the secret sharing scheme. Next, the first decryption unit 133 decrypts the encrypted vital data EVD using the decryption key SK to obtain the vital data VD. The first decryption unit 133 has a function for outputting the vital data VD.

(5) Control Unit 134

When the control unit 134 receives a user identifier ID from the outside, the control unit 134 outputs the user identifier ID to the reconstructed request processing unit 138. For example, the intermediate device 13 has a "browse button" and a "keyboard", and the user identifier ID is input using the button and the keyboard. In response, the control unit 134 obtains the second share SSD from the reconstructed request processing unit 138. Furthermore, the control unit 134 obtains the first share FSD corresponding to the user identifier from the second share DB 180 in the second storage unit 131. Furthermore, the control unit 134 obtains the encrypted vital data EVD corresponding to the user identifier ID from the second vital data DB 181 in the second storage unit 131. Next, the control unit 134 outputs the first share FSD, the second share SSD, and the encrypted vital data EVD to the first decryption unit 133, and obtains the vital data VD from the first decryption unit 133. The control unit 134 has a function for causing the display unit 132 to display the vital data VD.

(6) Second Encryption Unit 135

When the second encryption unit 135 receives the user identifier ID and the encrypted first share EFSD, the second encryption unit 135 obtains the intermediate device decryption key CSK from the second device information DB 182 in the second storage unit 131. Next, the second encryption unit 135 decrypts the encrypted first share EFSD using the intermediate device decryption key CSK. The second encryption unit 135 stores the first share FSD that is a decryption result into the second share DB 180 in the second storage unit 131 in such a manner that the first share FSD is associated with the user identifier ID. Subsequently, the second encryption unit 135 obtains the server device encryption key SPK from the second device information DB 182 in the second storage unit 131. Next, the second encryption unit 135 encrypts the first share FSD using the server device encryption key SPK. The result is referred to as the second encrypted first share E2FSD. Lastly, the second encryption unit 135 outputs the second encrypted first share E2FSD to the one of the functional blocks.

(7) Third Communication Unit 136

The third communication unit 136 has a function for transmitting and receiving various kinds of data to and from the server device 15 via the second computer network 14.

(8) Second Transmission and Reception Processing Unit 137

Figure 15:
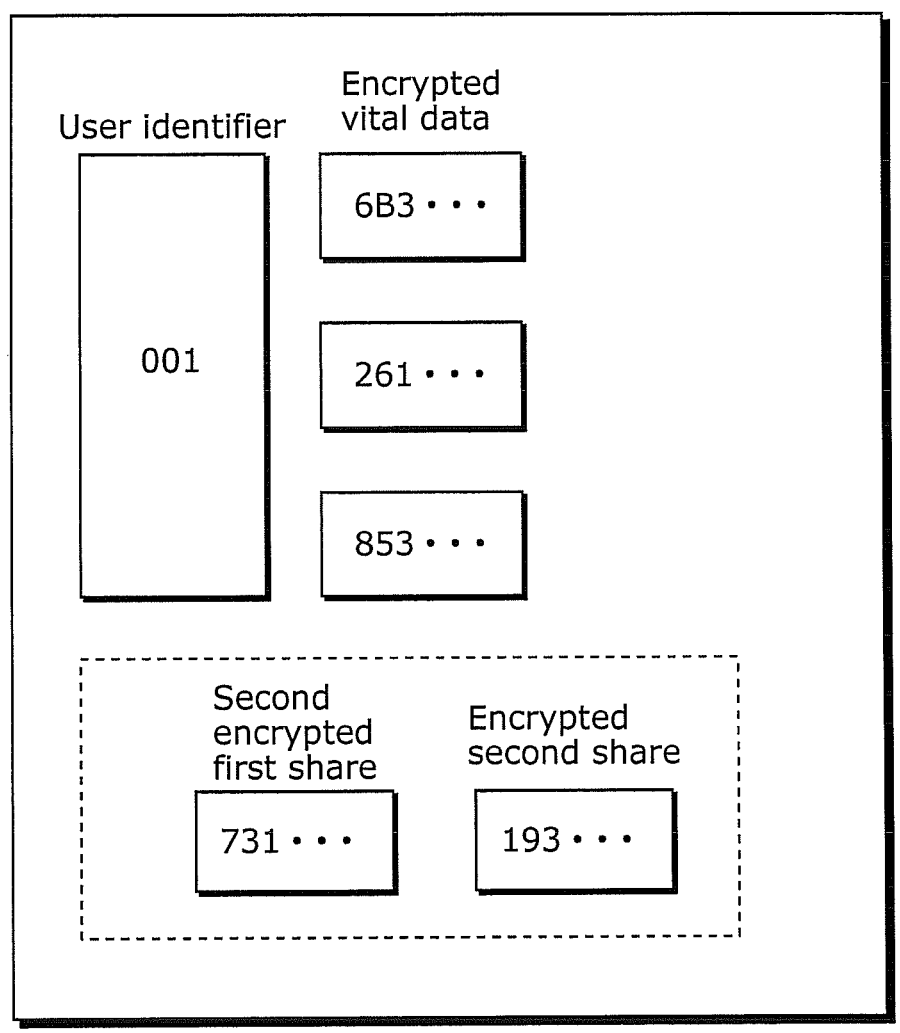
FIG. 15 is a diagram showing a structure of a second data SD.

When the second transmission and reception processing unit 137 receives the first data FD from the measurement device 11, the second transmission and reception processing unit 137 firstly stores the user identifier ID and the encrypted vital data EVD included in the first data FD into the second vital data DB 181 in the second storage unit 131. Subsequently, when the encrypted first share EFSD and the second encrypted first share E2FSD are included in the first data FD, the second transmission and reception processing unit 137 outputs the user identifier ID and the encrypted first share EFSD to the second encryption unit 135, and obtains the second encrypted first share E2FSD. As shown in FIG. 15, the second transmission and reception processing unit 137 generates the second data SD obtained by replacing the encrypted first share EFSD in the first data FD with the second encrypted first share E2FSD. Next, the second transmission and reception processing unit 137 transmits the second data SD to the server device 15 via the third communication unit 136. When the encrypted first share EFSD and the second encrypted first share E2FSD are not included in the first data FD, the second transmission and reception processing unit 137 transmits the first data FD as the second data SD to the server device 15 via the third communication unit 136.

(9) Reconstructed Request Processing Unit 138

Upon receiving the user identifier ID from the one of the functional blocks, the reconstructed request processing unit 138 transmits the user identifier ID to the measurement device 11 via the second communication unit 130. Next, the reconstructed request processing unit 138 receives the encrypted second share ESSD from the measurement device 11 via the second communication unit 130. The reconstructed request processing unit 138 outputs the encrypted second share ESSD to the first decryption unit 133.

(10) Second Setting Processing Unit 139

The second setting processing unit 139 is capable of setting the intermediate device decryption key CSK and the server device encryption key SPK, into the second device information DB 182 in the second storage unit 131, based on the data that is input from the outside. For example, the intermediate device 13 includes a keyboard, and the second setting processing unit 139 is capable of setting these pieces of information based on the data that is input using the keyboard. In addition, the second setting processing unit 139 includes a predetermined authentication function (such as password authentication), and performs authentication when the intermediate device 13 establishes a connection with the server device 15. When the predetermined authentication is successfully performed, the server device 15 is capable of setting the user identifier ID and the first share FSD, into the second share DB 180 in the second storage unit 131 via the second setting processing 139.

[Structure of Server Device 15]

Lastly, a structure of the server device 15 is described.

Figure 16:
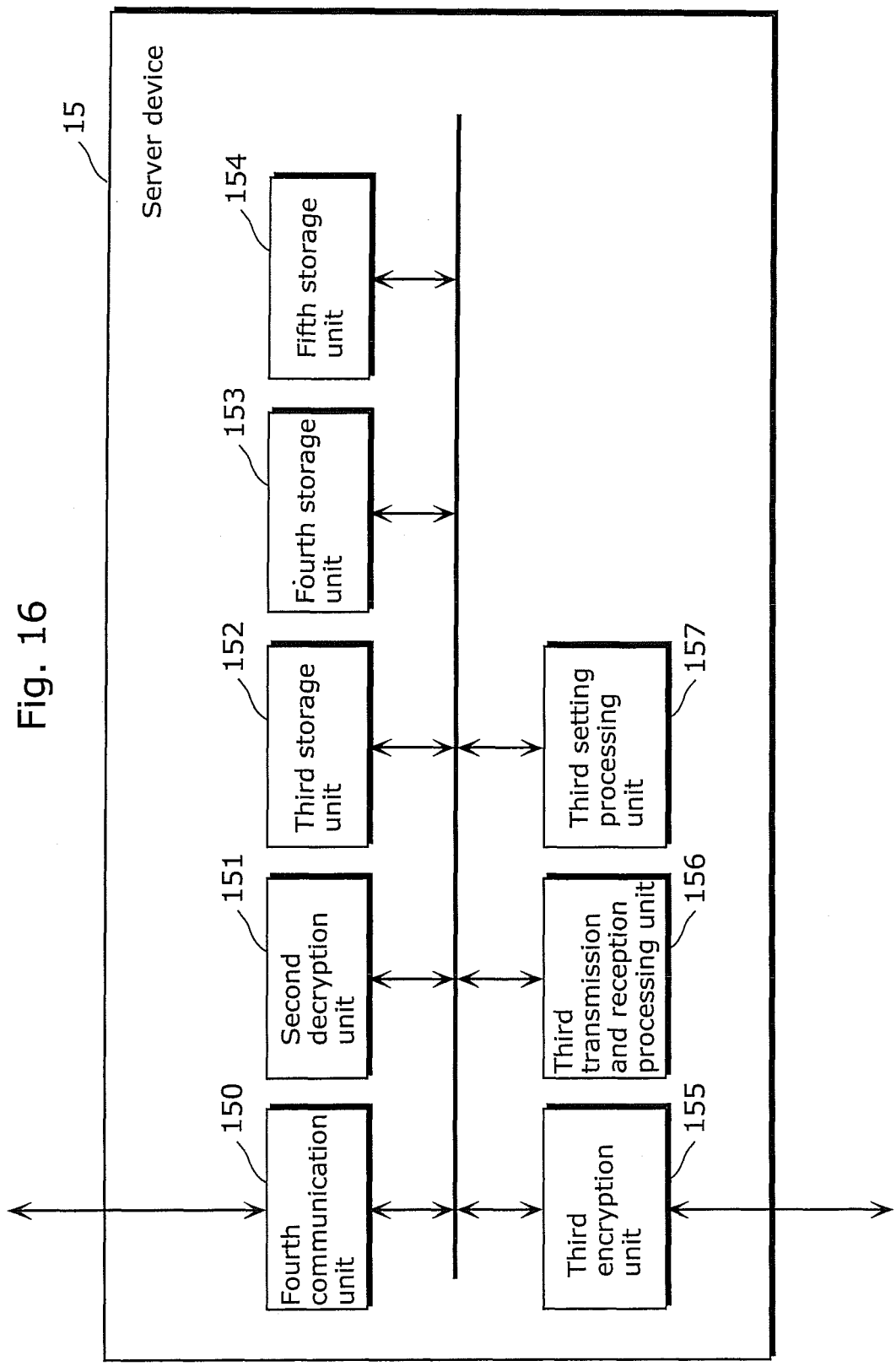
FIG. 16 is a block diagram showing a structure of a server device.

FIG. 16 is a block diagram showing the structure of the server device 15. As shown in FIG. 16, the server device 15 includes a fourth communication unit 150, a second decryption unit 151, a third storage unit 152, a fourth storage unit 153, a fifth storage unit 154, a third encryption unit 155, a third transmission and reception processing unit 156, and a third setting processing unit 157. Among the structural elements, the essential structural elements are the fourth communication unit 150, the second decryption unit 151, and the third encryption unit 155.

It is to be noted that the fourth communication unit 150 corresponds to a fourth communication unit in the CLAIMS of the present application. In addition, the second decryption unit 151 corresponds to a reconstruction unit and a vital data decryption unit in the CLAIMS of the present application. In addition, the third storage unit 152 corresponds to a holding unit in the CLAIMS of the present application. In addition, the third encryption unit 155 corresponds to a share decryption unit in the CLAIMS of the present application. In addition, the third setting processing unit 157 corresponds to a supply unit in the CLAIMS of the present application.

(1) Fourth Communication Unit 150

The fourth communication unit 150 has a function for transmitting and receiving various kinds of data to and from the intermediate device 13 via the second computer network 14.

(2) Second Decryption Unit 151

The second decryption unit 151 has the following two functions.

A. Reconstruction of Decryption Key from Shares

The second decryption unit 151 has a function for a case of receiving the first share FSD and the second share SSD from the one of the functional blocks; the function is for decrypting a decryption key SK according to the secret sharing scheme and outputting the decryption key SK to the one of the functional blocks.

B. Decryption of Encrypted Vital Data

The second decryption unit 151 has a function for a case of receiving encrypted vital data EVD and the decryption key SK from the one of the functional blocks; the function is for decrypting the encrypted vital data EVD using the decryption key SK and outputting the vital data VD as the decryption result to the one of the functional blocks.

(3) Third Storage Unit 152

Figure 17:
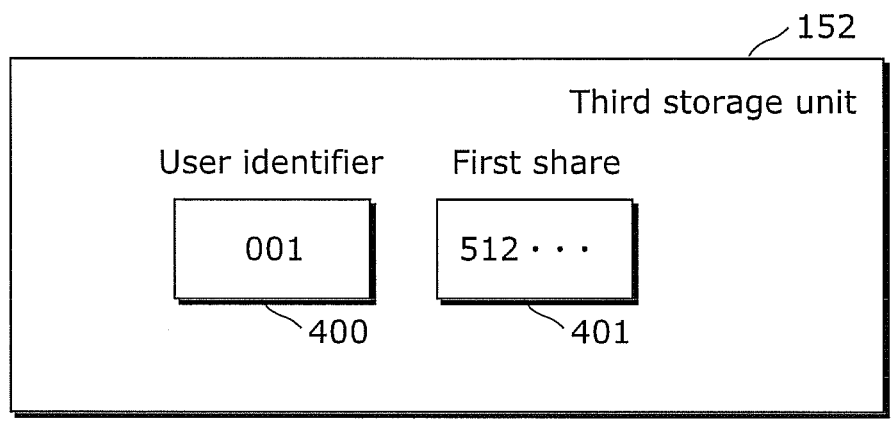
FIG. 17 is a diagram showing a structure of a third storage unit of the server device.

As shown in FIG. 17, the third storage unit 152 holds a user identifier ID (a user identifier 400 in FIG. 17) and a first share FSD (a first share 401 in FIG. 17).

(4) Fourth Storage Unit 153

Figure 18:
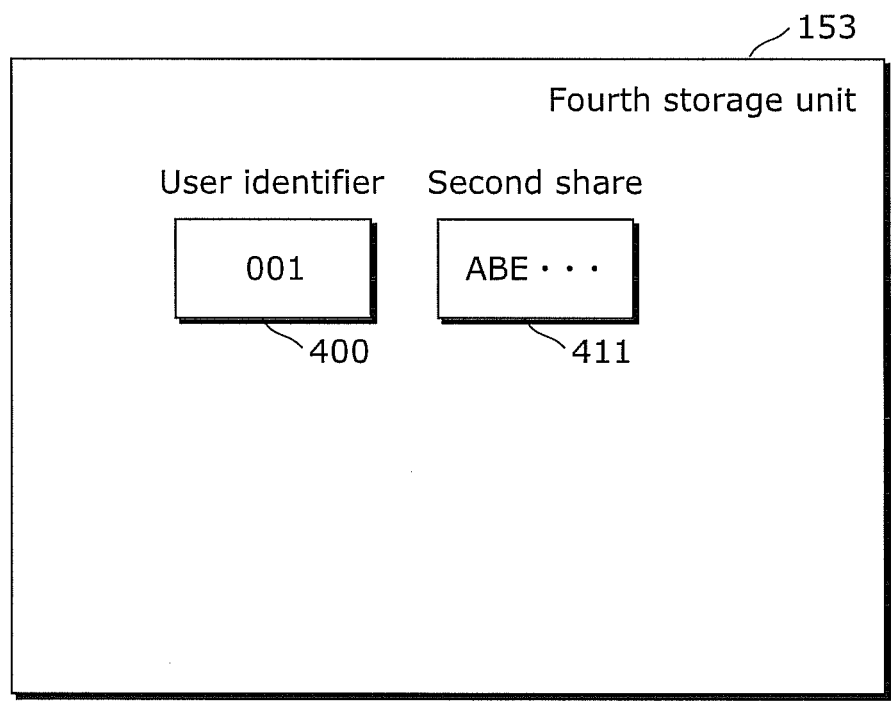
FIG. 18 is a diagram showing a structure of a fourth storage unit of the server device.

As shown in FIG. 18, the fourth storage unit 153 holds a user identifier ID (a user identifier 410 in FIG. 18) and a second share SSD (a second share 411 in FIG. 18).

(5) Fifth Storage Unit 154

Figure 19:
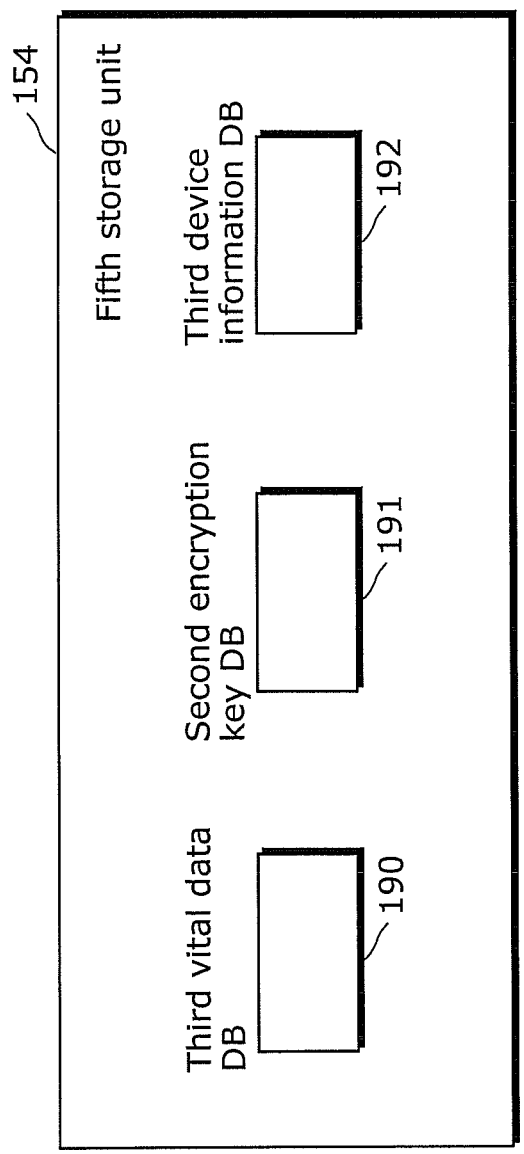
FIG. 19 is a diagram showing a structure of a fifth storage unit of the server device.

As shown in FIG. 19, the fifth storage unit 154 holds a third vital data DB 190, a second encryption key DB 191, and a third device information DB 192.

Figure 20:
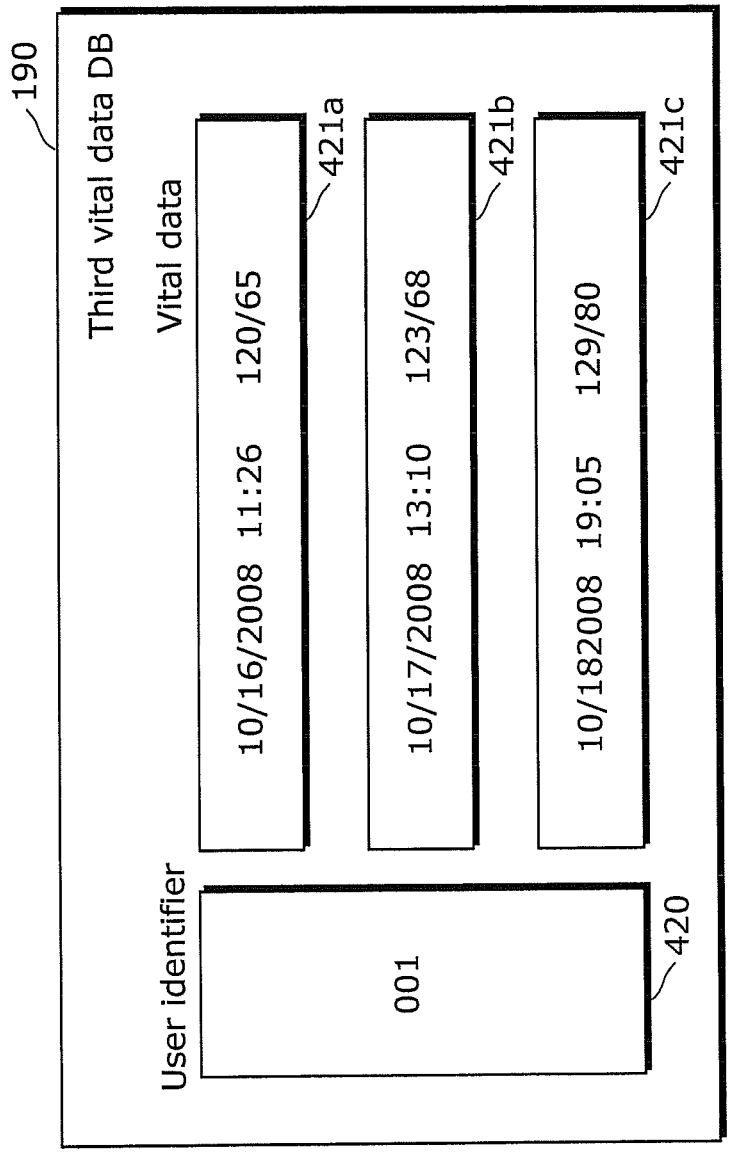
FIG. 20 is a diagram showing a structure of a third vital data DB in the fifth storage unit of the server device.

As shown in FIG. 20, the third vital data DB 190 includes a user identifier ID (a user identifier 420 in FIG. 20) and vital data VD (vital data 421a, 421b, and 421c in FIG. 20).

Figure 21:
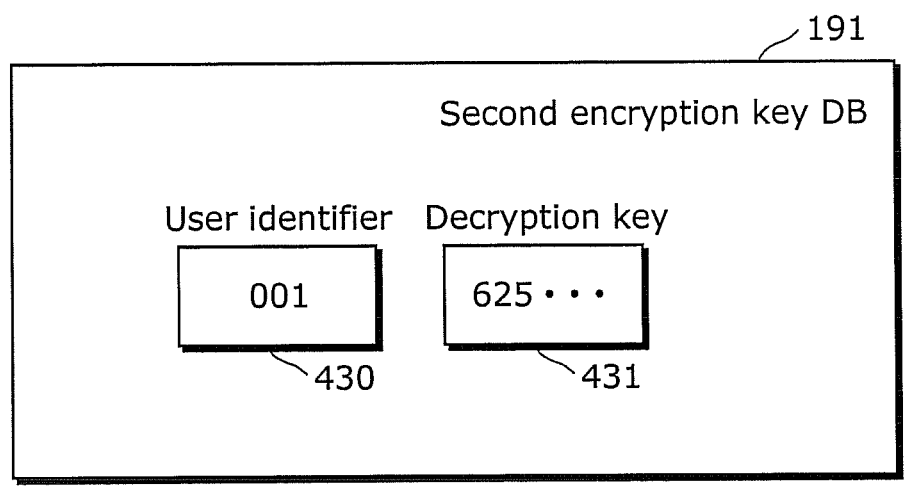
FIG. 21 is a diagram showing a structure of a second encryption key DB in the fifth storage unit of the server device.

As shown in FIG. 21, the second encryption key DB 191 includes a user identifier ID (a user identifier 430 in FIG. 21) and a decryption key SK (a decryption key 431 in FIG. 21).

Figure 22:
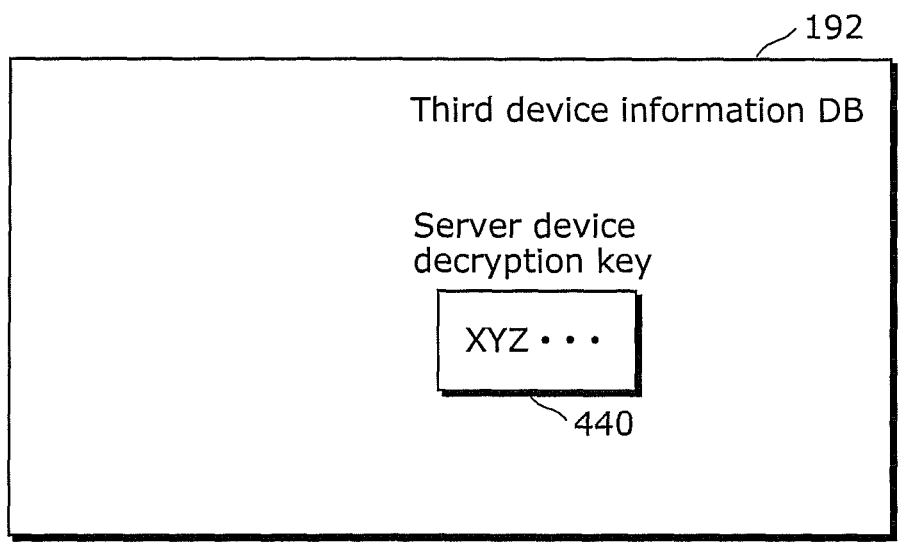
FIG. 22 is a diagram showing a structure of a third device information DB in the fifth storage unit of the server device.

As shown in FIG. 22, the third device information DB 192 includes the server device decryption key SSK (the server device decryption key 440 in FIG. 21).

(6) Third Encryption Unit 155

When the third encryption unit 155 receives, from the one of the functional blocks, the server device decryption key SSK, the second encrypted first share E2FSD, and the encrypted second share ESSD, the third encryption unit 155 decrypts both of the second encrypted first share E2FSD and the encrypted second share ESSD using the server device decryption key SSK to obtain the first share FSD and the second share SSD. Next, the third encryption unit 155 outputs the first share FSD and the second share SSD to the one of the functional blocks.

(7) Third Transmission and Reception Processing Unit 156

When the third transmission and reception processing unit 156 receives the second data SD from the intermediate device 13 via the fourth communication unit 150, the third transmission and reception processing unit 156 firstly checks whether or not the second encrypted first share E2FSD is included in the second data SD. When the second encrypted first share E2FSD is included therein, the third transmission and reception processing unit 156 obtains the server device decryption key SSK from the third device information DB 192 in the fifth storage unit 154. Next, the third transmission and reception processing unit 156 extracts, from the second data SD, the second encrypted first share E2FSD and the encrypted second share ESSD, outputs, to the third encryption unit 155, the server device decryption key SSK, the second encrypted first share E2FSD, and the encrypted second share ESSD, and obtains the first share FSD and the second share SSD from the third encryption unit 155. Next, the third transmission and reception processing unit 156 outputs the first share FSD and the second share SSD to the second decryption unit 151, and obtains the decryption key SK from the second decryption unit 151. The third transmission and reception processing unit 156 stores the decryption key SK into the second encryption key DB 191 in the fifth storage unit 154. The above-described operations are operations that are additionally performed when the second encrypted first share E2FSD is included in the second data SD. Next, the third transmission and reception processing unit 156 outputs, to the second decryption unit 151, the decryption key SK obtained from the second encryption key DB 191 in the fifth storage unit 154, and obtains the vital data VD from the second decryption unit 151. The third transmission and reception processing unit 156 stores the obtained vital data VD into the third vital data DB 190 in the fifth storage unit 154.

(8) Third Setting Processing Unit 157

The third setting processing unit 157 has a function for setting a server device decryption key SSK, into the third device information DB 192 in the fifth storage unit 154, based on the data that is input from the outside. For example, the third setting processing unit 157 is capable of setting the server device decryption key SSK based on the data that is input using a keyboard.

Furthermore, the third setting processing unit 157 has a function for setting the second share SSD into the measurement device 11, when the measurement device 11 is directly connected to the server device 15. Furthermore, the third setting processing unit 157 has a function for setting the first share FSD into the intermediate device 13 when the intermediate device 13 is directly connected to the server device 15.

The respective structural elements have been described above. Hereinafter, exemplary operations performed by the respective structural devices are described. First, the outline of the exemplary operations and the achievable functions are described.

Figure 23:
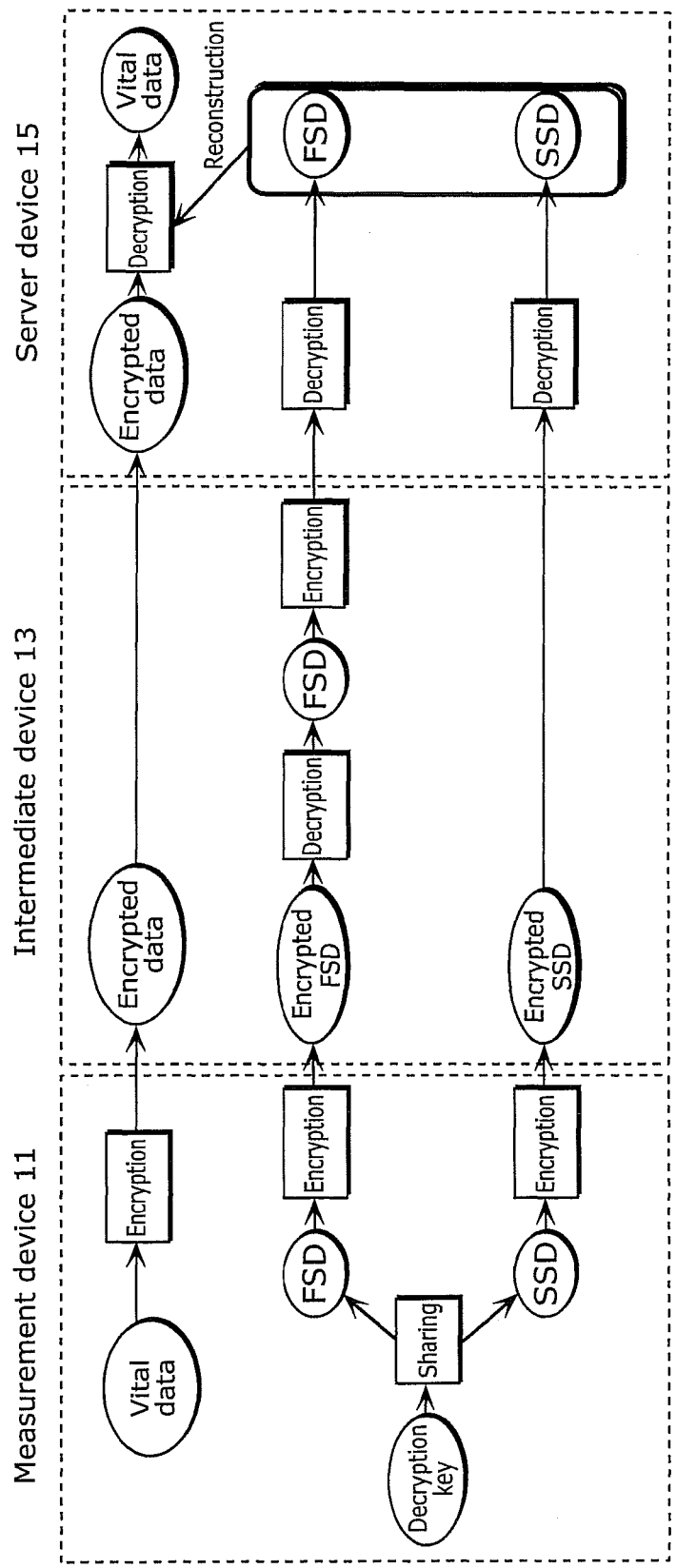
FIG. 23 is a diagram showing a concept of a health care system.

With reference to FIG. 23, when the measurement device 11 is firstly used by the patient, the measurement device 11 firstly generates an encryption key PK, a decryption key SK, and two shares (a first share FSD and a second share SSD) corresponding to the decryption key SK. Next, the measurement device 11 measures vital data VD when the patient presses the "measure button", and accumulates the vital data VD encrypted using the encryption key PK. When a nursing staff member visits the patient's home with certain timing and the nursing staff member presses the "transmission button" of the measurement device 11, the measurement device 11 encrypts the first share FSD in such a manner that only the intermediate device 13 can decrypt the first share FSD encrypted, and encrypts the second share SSD in such a manner that only the server device 15 can decrypt the second share SSD encrypted. The measurement device 11 transmits the first share FSD encrypted and the second share SSD to the intermediate device 13 brought by the nursing staff member, together with the vital data VD encrypted. Upon receiving the shares and data, the intermediate device 13 accumulates the vital data VD encrypted first. Next, the intermediate device 13 decrypts the first share FSD encrypted, and accumulates the first share FSD decrypted. Next, the intermediate device 13 encrypts the first share FSD in such a manner that only the sever device 15 can decrypt the first share FSD encrypted, and temporarily accumulates the first share FSD encrypted. After the nursing staff member returns to the hospital, the intermediate device 13 transmits, to the server device 15, the first share FSD, the second share SSD, and the vital data VD encrypted respectively. The sever device 15 decrypts the first share FSD encrypted and the second share SSD encrypted to obtain the first share FSD and the second share SSD, respectively, and obtains the decryption key SK from the first share FSD and the second share SSD. Next, the server device 15 decrypts the vital data VD encrypted using the decryption key SK to obtain the vital data VD. In this way, the server device 15 can obtain the vital data VD.

Figure 24:
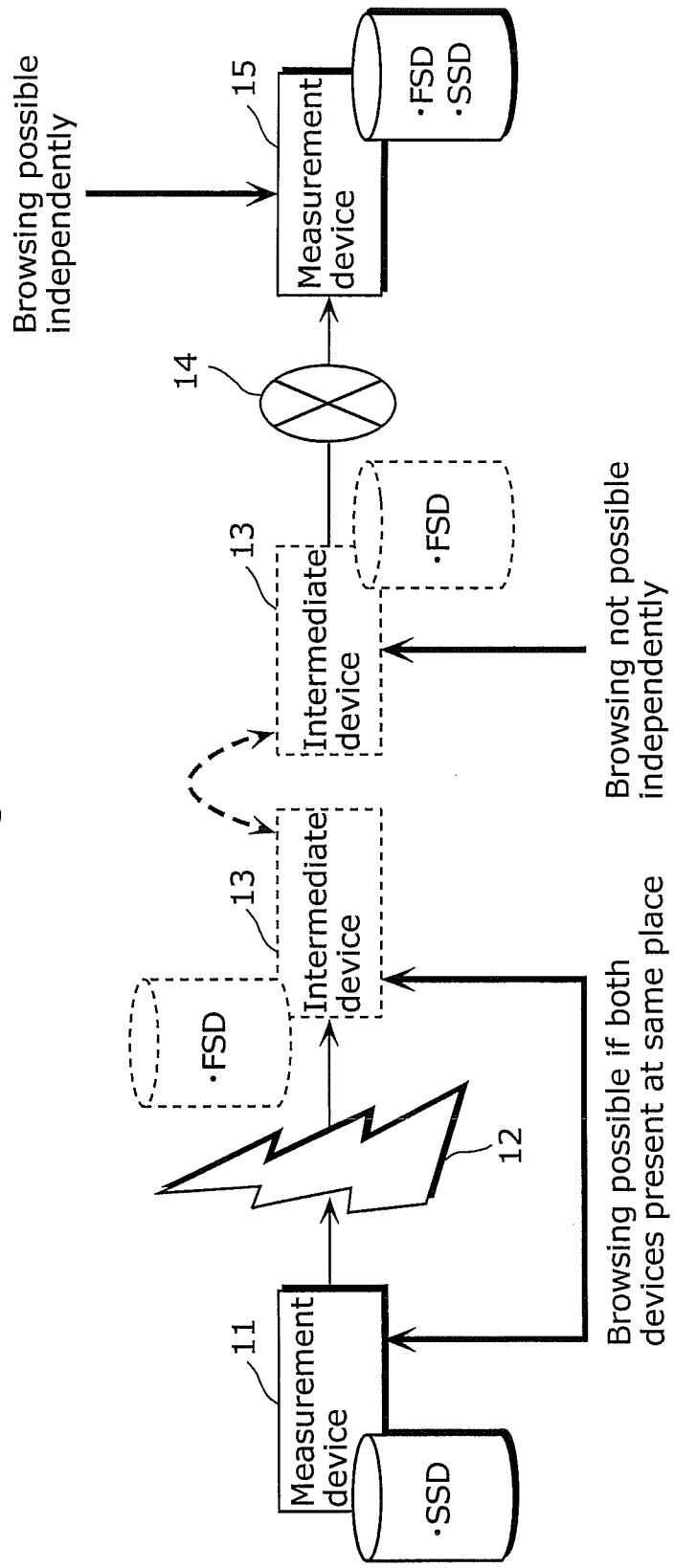
FIG. 24 is a diagram showing a concept of exemplary operations in the health care system.

Another example is given with reference to FIG. 24. It is assumed that, in this case, the nursing staff member visits the patient's home with timing after the aforementioned timing, and the nursing staff member wishes to browse the vital data VD measured before. At this time, when the nursing staff member presses the "browse button" of the intermediate device 13 held by the nursing staff member himself or herself and inputs the user identifier ID of the patient, the intermediate device 13 accesses the measurement device 11 and obtain the second share SSD. Next, the intermediate device 13 reconstructs the decryption key SK by combining the second share SSD obtained from the measurement device 11 and the first share FSD held by the intermediate device 13. The intermediate device 13 decrypts the held vital data VD encrypted, using the reconstructed decryption key SK to obtain the vital data VD. In this way, the intermediate device 13 also allows browsing of the vital data VD when it co-operates with the measurement device 11.

Another case is considered in which the measurement device 11 in use by the patient has a trouble with certain timing. In this case, a system manager firstly sets a user identifier ID etc. into a measurement device 11x having the same structure as that of the measurement device 11. Next, the server device 15 accesses the measurement device 11x, and outputs, to the measurement device 11x, the first share FSD and the second share SSD held by the server device 15. In this way, the server device 15 keeps holding the first share FSD and the second share SSD after the decryption key SK is reconstructed, and thus is capable of setting the same first share FSD and the same second share SSD into the measurement device 11x even when the measurement device 11 has a trouble. It is to be noted that the server device 15 may set only the second share SSD into the measurement device 11x. It is to be noted that the server device 15 may generate, from the decryption key SK, two shares that are different from the first share FSD and the second share SSD, and output the generated two shares to the measurement device 11x. At this time, uniquely associating the measurement device 11x with each of the shares makes it possible to identify the measurement device 11x that is the source of the share if the share leaks to the outside.

Lastly, another case is considered in which the intermediate device 13 in use by the nursing staff member has a trouble with certain timing. In this case, a system manager firstly sets a user identifier ID etc. into an intermediate device 13y having the same structure as that of the intermediate device 13. Next, the server device 15 accesses the intermediate device 13y, and outputs the first share FSD held by the server device 15. In this way, the server device 15 keeps holding the first share FSD even after the decryption key SK is reconstructed, and thus is capable of setting the same first share FSD into the other intermediate device 13y even when the intermediate device 13 has a trouble. It is to be noted that the server device 15 may generate, from the decryption key SK, a share that are different from the first share FSD and the second share SSD, and output the generated two shares to the intermediate device 13y. At this time, uniquely associating the intermediate device 13y with each of the shares makes it possible to identify the intermediate device 13y that is the source of the share if the share leaks to the outside.

The outline of the operations has been described above. Hereinafter, the operations are described in detail. Here, the descriptions are given separately for: (i) operations performed by the measurement device 11 when measuring vital data and transmitting the vital data; (ii) operations performed by the intermediate device 13 when displaying the vital data; (iii) operations for setting a share into a measurement device 11x when the measurement device 11 has a trouble; and (iv) operations performed for setting a share into an intermediate device 13y when the intermediate device 13 has a trouble.

[(i) Operations Performed by Measurement Device 11 to Measure and Transmit Vital Data]

Figure 25:
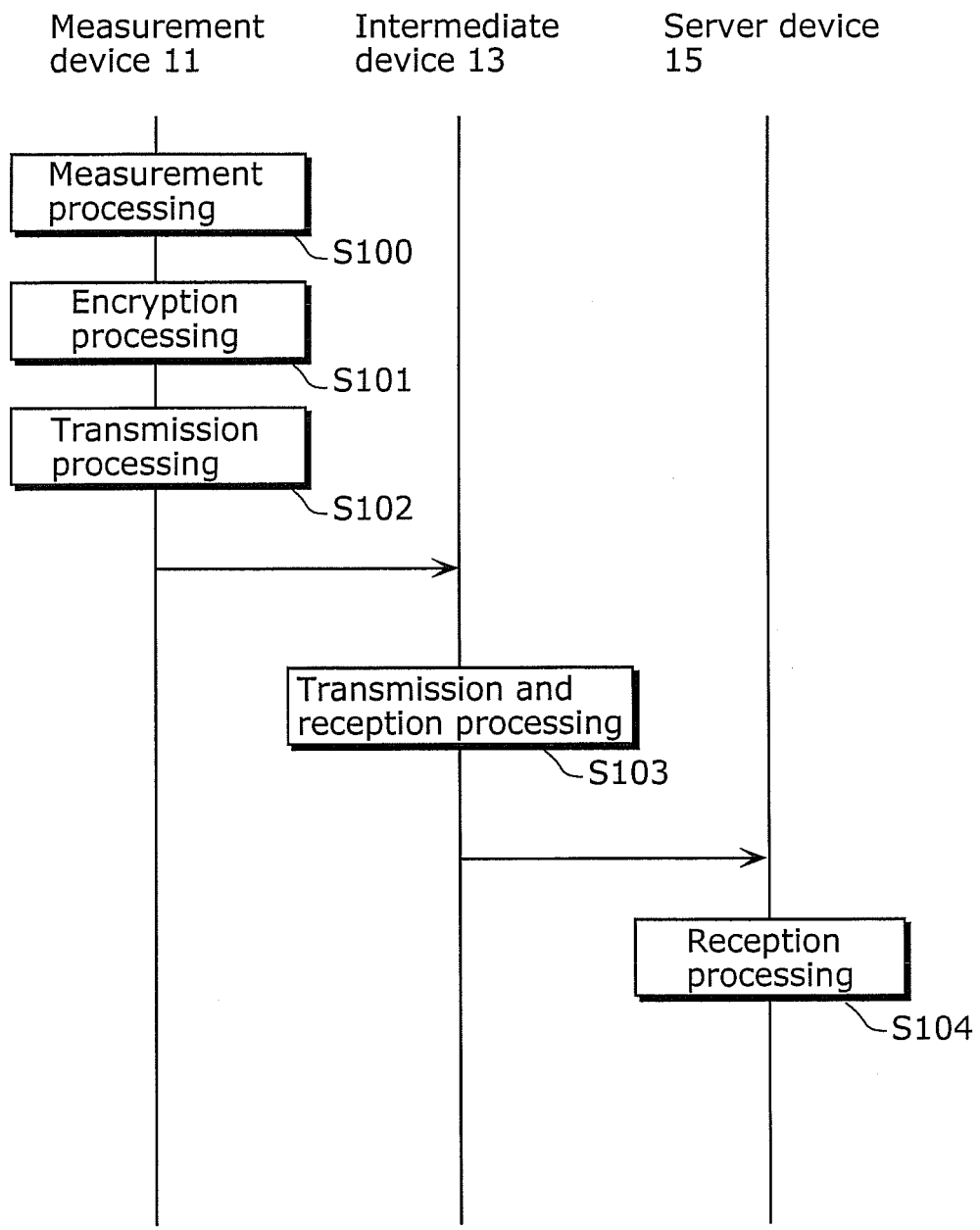
FIG. 25 is a flowchart of exemplary operations at the time of measurement in the health care system.

Hereinafter, with reference to a flowchart in FIG. 25, a description is given of the operations performed by the measurement device 11 when measuring and transmitting the vital data.

The measurement device 11 performs a "measurement process (Step S100)".

The measurement device 11 performs an "encryption process (Step S101)".

The measurement device 11 performs a "transmission process (Step S102)".

The intermediate device 13 performs a "transmission and reception process (Step S103)".

The server device 15 performs the "reception process (Step S104)" to complete the sequential processes.

Next, detailed descriptions are given for the respective operations performed by the measurement device 11.

Figure 26:
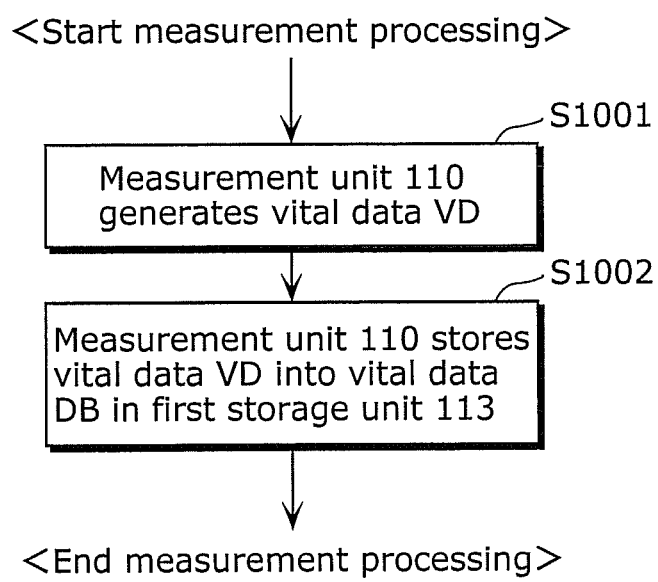
FIG. 26 is a flowchart showing details of "measurement processing" performed by the measurement device.

[Details of Measurement Process (Step S100): see FIG. 26]

The measurement unit 110 generates vital data VD (Step S1001).

The measurement unit 110 stores the vital data VD into the vital data DB 171 in the first storage unit 113 (Step S1002).

Figure 27:
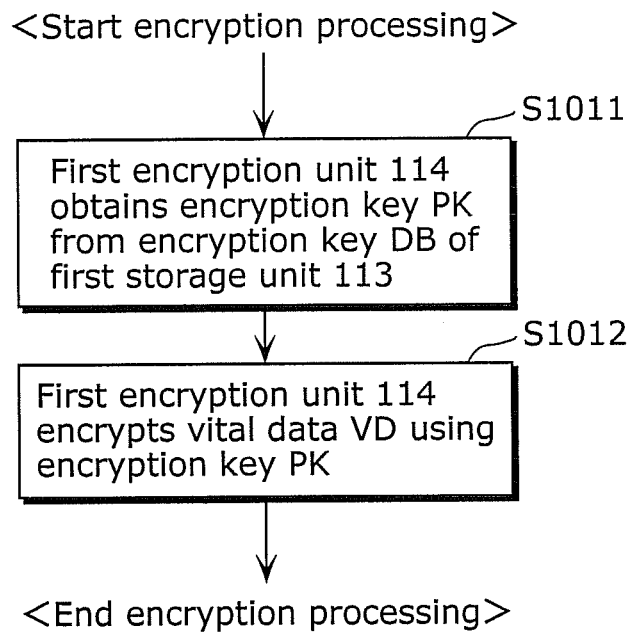
FIG. 27 is a flowchart showing details of "encryption processing" performed by the measurement device.

[Details of Encryption Process (Step S101): see FIG. 27]

The first encryption unit 114 obtains the encryption key PK from the encryption key DB 172 in the first storage unit 113 (Step S1011).

The first encryption unit 114 encrypts the vital data VD using the encryption key PK (Step S1012).

Figure 28:
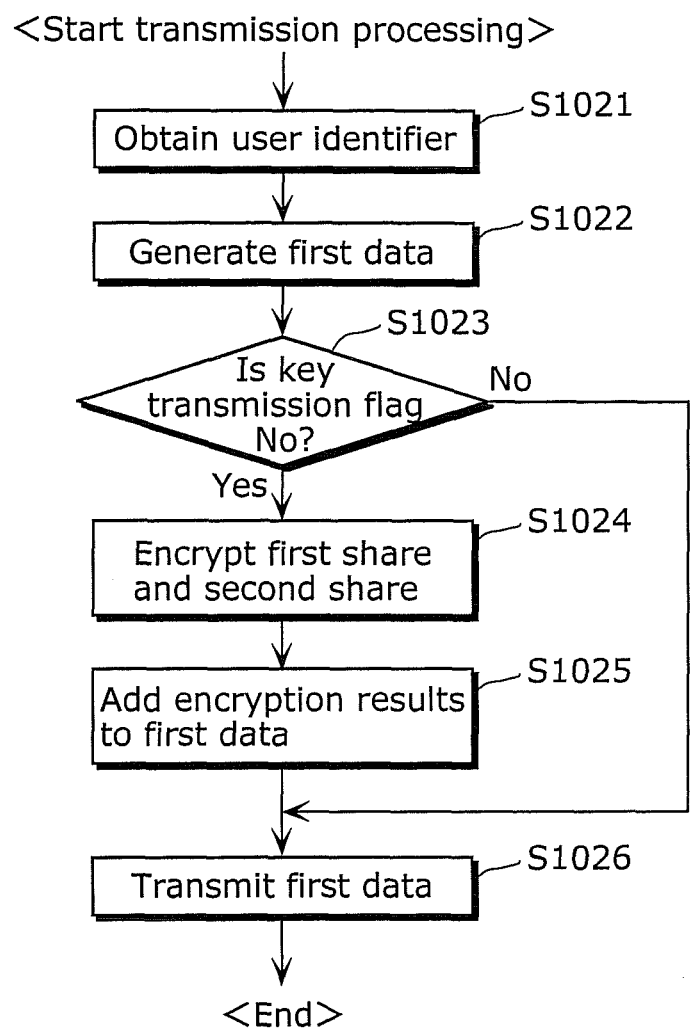
FIG. 28 is a flowchart showing details of "transmission processing" performed by the measurement device.

[Details of Transmission Process (Step S102): see FIG. 28]

The first transmission and reception processing unit 116 obtains the user identifier ID from the device information DB 173 in the first storage unit 113 (Step S1021).

The first transmission and reception processing unit 116 generates the first data FD (Step S1022).

When the key transmission flag SF indicates "No" (Yes in Step S1023), the first encryption unit 114 encrypts the first share FSD and the second share SSD (Step S1024).

The first transmission and reception processing unit 116 adds, to the first data FD, the encrypted first share EFSD and the encrypted second share ESSD (Step S1025).

When the key transmission flag SF indicates "Yes" ("No" in Step S1023) or after the processing in Step S1025, the first transmission and reception processing unit 116 transmits the first data FD to the intermediate device 13 (Step S1026).

Next, detailed descriptions are given for the respective operations performed by the intermediate device 13.

Figure 29:
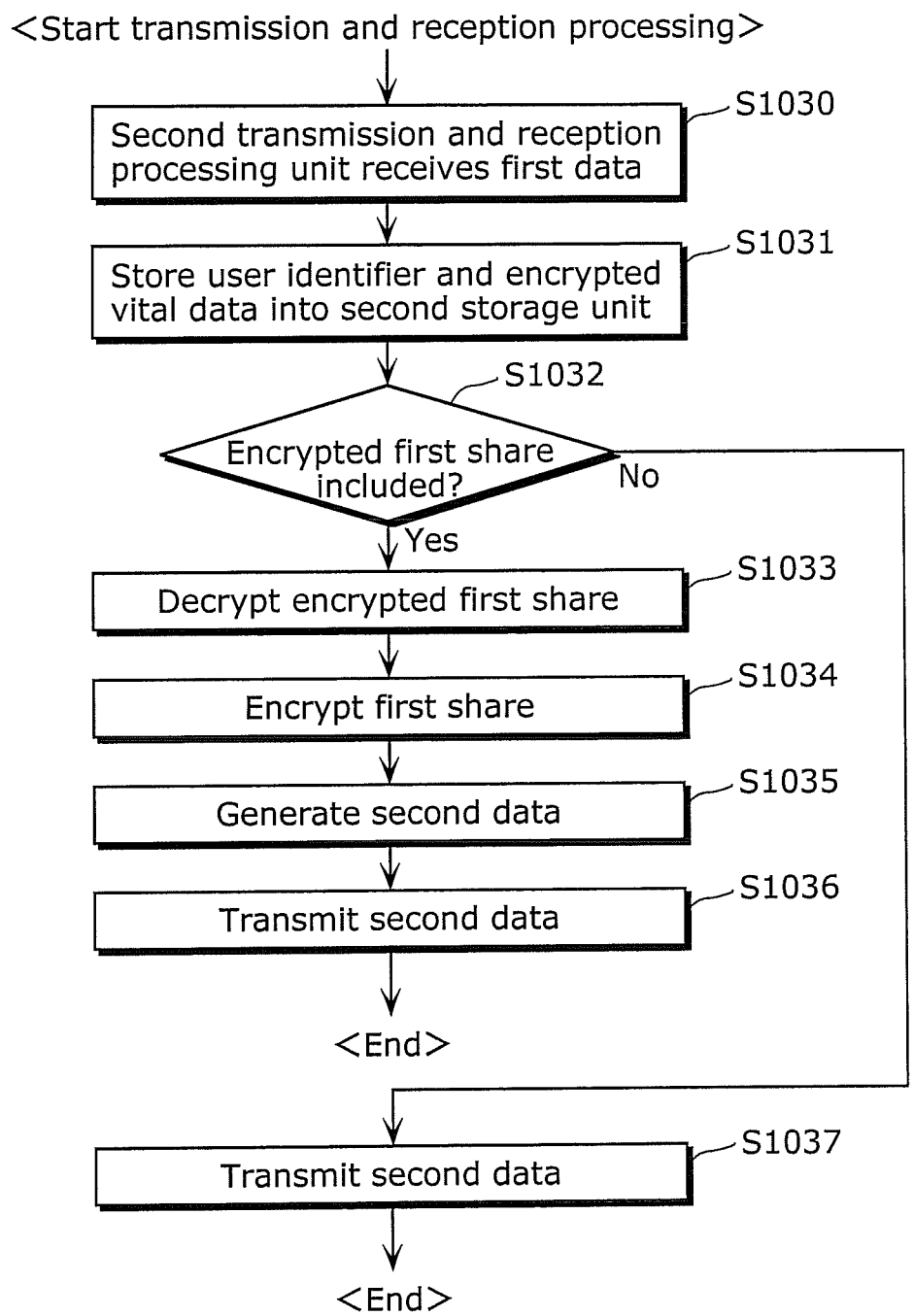
FIG. 29 is a flowchart showing details of "transmission and reception processing" performed by the intermediate device.

[Details of Transmission and Reception Process (Step S103): see FIG. 29]

The second transmission and reception processing unit 137 receives the first data FD from the measurement device 11 (Step S1030).

The second transmission and reception processing unit 137 stores the user identifier ID and the encrypted vital data EVD into the second vital data DB 181 in the second storage unit 131 (Step S1031).

When the encrypted first share EFSD is included in the first data FD (Yes in Step S1032), the second encryption unit 135 decrypts the encrypted first share EFSD (Step S1033).

The second encryption unit 135 encrypts the first share FSD (Step S1034).

The second transmission and reception processing unit 137 replaces the encrypted first share EFSD included in the first data FD with the second encrypted first share E2FSD to generate the second data SD (Step S1035).

The second transmission and reception processing unit 137 transmits (Step S1036) the second data SD to the server device 15 to complete the sequential processes.

When the encrypted first share EFSD is not included in the first data FD (No in Step S1032), the second transmission and reception processing unit 137 transmits (Step S1037) the first data FD as the second data SD to the server device 15 to complete the sequential processes.

Lastly, detailed descriptions are given for the respective operations performed by the server device 15.

Figure 30:
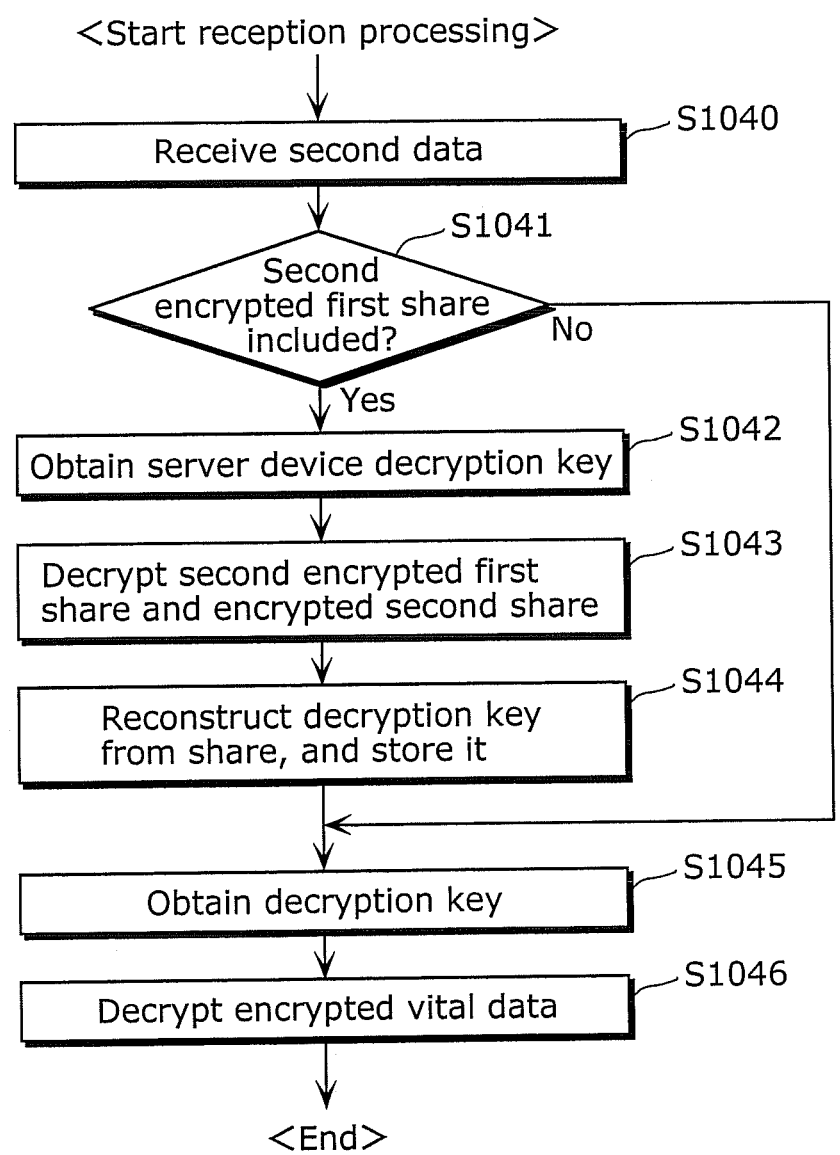
FIG. 30 is a flowchart showing details of "reception processing" performed by the server device.

[Details of Reception Process (Step S104): see FIG. 30]

The third transmission and reception processing unit 156 receives the second data SD from the intermediate device 13 (Step S1040).

The third transmission and reception processing unit 156 checks whether or not the second encrypted first share E2FSD is included in the second data SD (Step S1041).

When the second encrypted first share E2FSD is included in the second data SD (Yes in Step S1041), the third transmission and reception processing unit 156 obtains the server device decryption key SSK from the third device information DB 192 in the fifth storage unit 154 (Step S1042).

The third encryption unit 155 decrypts the second encrypted first share E2FSD and the encrypted second share ESSD using the server device decryption key SSK (Step S1043).

The second decryption unit 151 obtains the decryption key SK using the first share FSD and the second share SSD. The second decryption unit 151 stores the obtained decryption key SK into the second encryption key DB 191 in the fifth storage unit 154 (Step S1044).

After the processing in Step S1044, or when the second encrypted first share E2FSD is not included in the second data SD (No in Step S1041), in order to obtain vital data VD, the second decryption unit 151 decrypts the encrypted vital data EVD using the decryption key SK obtained (Step S1045) from the second encryption key DB 191 in the fifth storage unit 154. The second decryption unit 151 stores the vital data VD into the third vital data DB 190 in the fifth storage unit 154 to complete the sequential processes (Step S1046).

[(ii) Operations that Intermediate Device 13 Performs when Displaying Vital Data]

Figure 31:
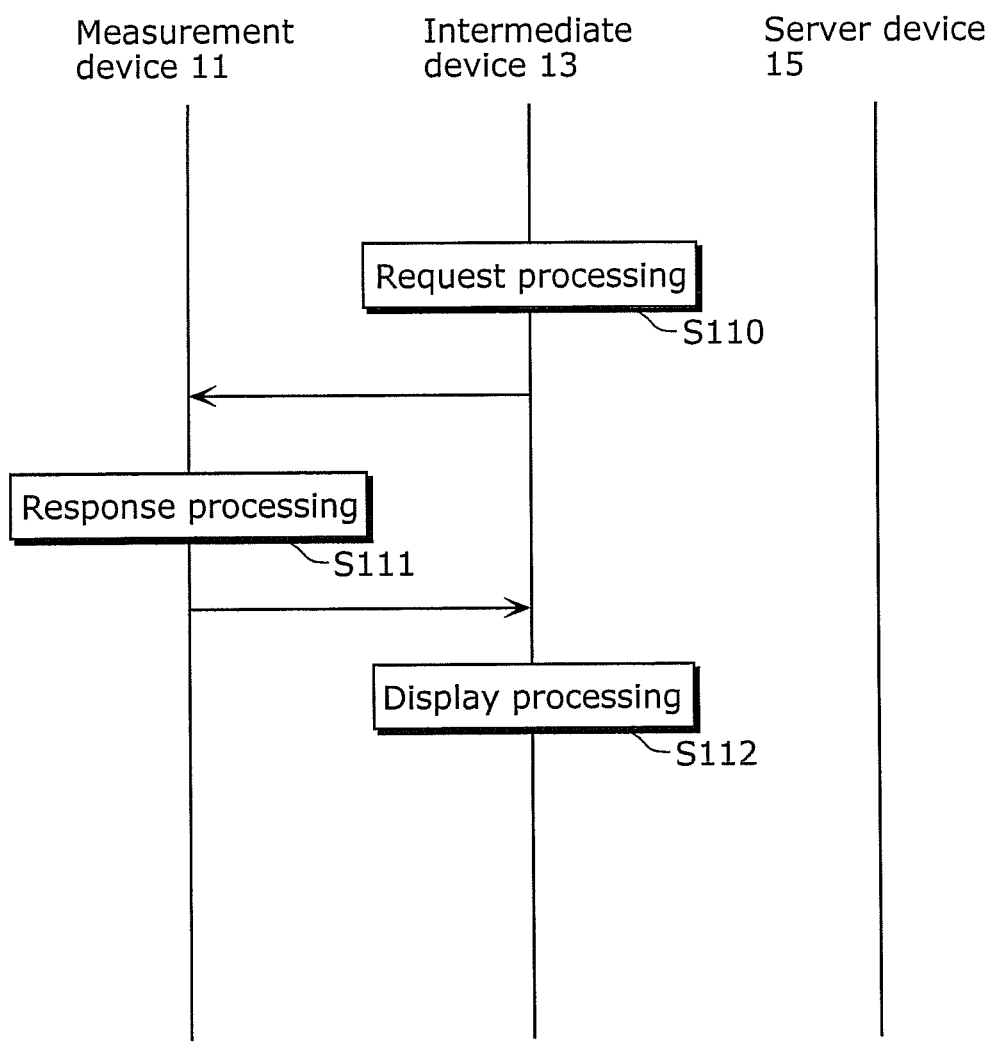
FIG. 31 is a flowchart of exemplary operations at the time of display of vital data in the health care system.

Hereinafter, with reference to a flowchart in FIG. 31, descriptions are given of operations performed by the intermediate device 13 to display the vital data.

The intermediate device 13 performs a "request process (Step S110)".

The measurement device 11 performs a "response process (Step S111)".

The intermediate device 13 performs a "display process (Step S112)" to complete the sequential processes.

Next, descriptions are given of operations performed by the respective structural elements of the intermediate device 13 to display the vital data.

Figure 32A:
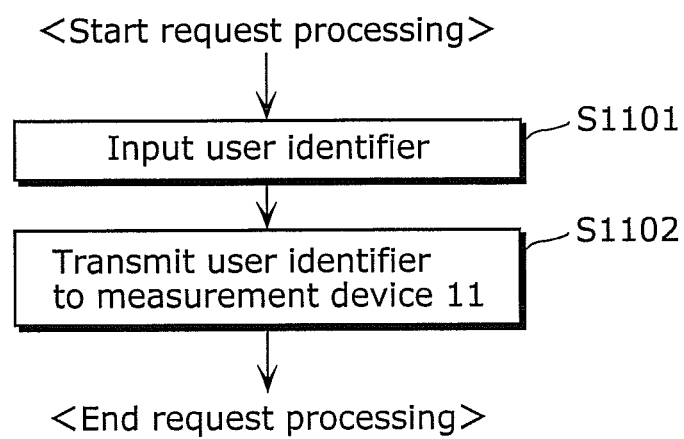
FIG. 32A is a flowchart showing details of "request processing" performed by the intermediate device.

[Details of Response Process (Step S110): FIG. 32A]

The control unit 134 receives an input of a user identifier ID from the outside (Step S1101).

The reconstructed request processing unit 138 transmits the user identifier ID to the measurement device 11 (Step S1102).

Figure 32B:
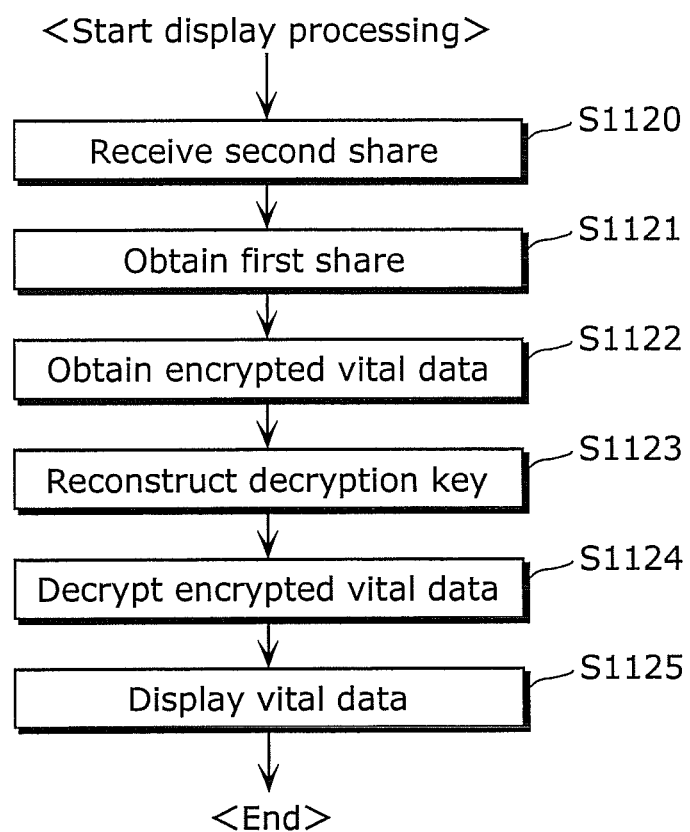
FIG. 32B is a flowchart showing details of "display processing" performed by the intermediate device.

[Details of Display Process (Step S112): see FIG. 32B]

The control unit 134 receives the second share SSD (Step S1120).

The control unit 134 obtains the first share FSD corresponding to the user identifier ID from the second share DB 180 in the second storage unit 131 (Step S1121).

The control unit 134 obtains the encrypted vital data EVD corresponding to the user identifier ID from the second vital data DB 181 in the second storage unit 131 (Step S1122).

The first decryption unit 133 reconstructs the decryption key SK from the first share FSD and the second share SSD (Step S1123).

The first decryption unit 133 decrypts the encrypted vital data EVD using the decryption key SK to obtain the vital data VD (Step S1124).

The display unit 132 displays vital data VD (Step S1125).

Figure 33:
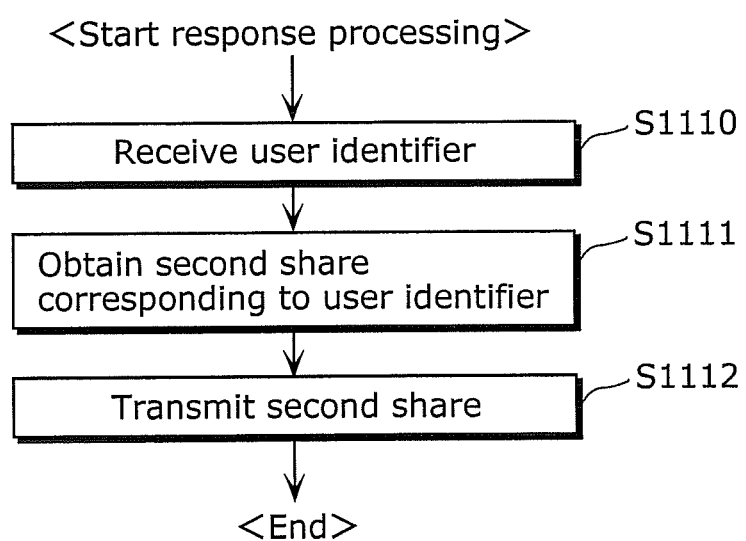
FIG. 33 is a flowchart showing details of the "response processing" performed by the measurement device.

[Details of Response Process (Step S111): FIG. 33]

The reconstructed response processing unit 117 receives a user identifier ID from the intermediate device 13 (Step S1110).

The reconstructed response processing unit 117 obtains the second share SSD from the share DB 170 in the first storage unit 113 (Step S1111).

The reconstructed response processing unit 117 transmits the second share SSD to the intermediate device 13 (Step S1112).

[(iii) Operations Performed to Set Share into Measurement Device 11x when Measurement Device in Use has Trouble]

Figure 34:
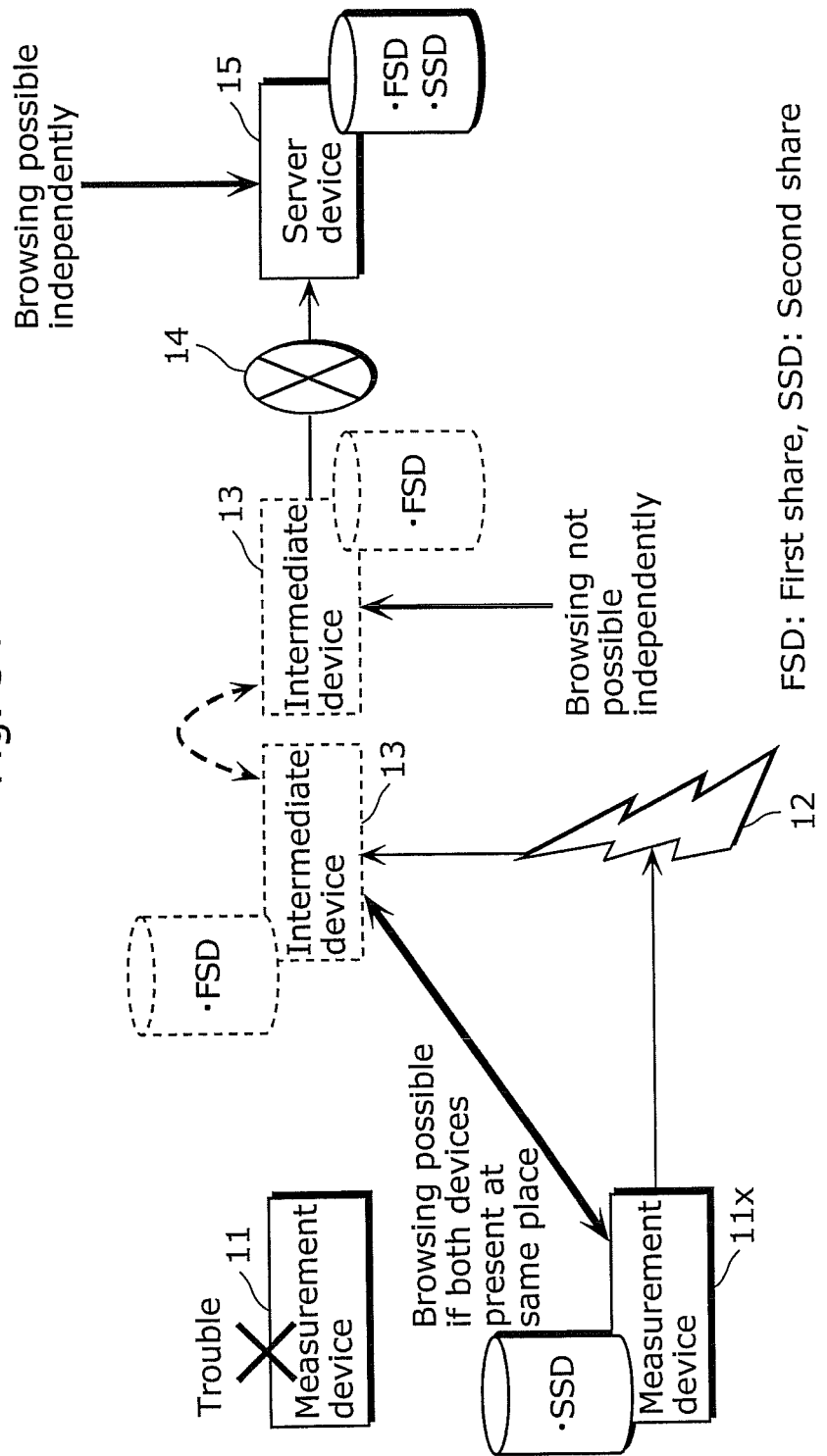
FIG. 34 is another diagram showing a concept of operations in the health care system.

Hereinafter, a description is given of operations for setting a substitute measurement device. First, with reference to FIG. 34, backgrounds of the operations are described in detail again. Here, it is assumed that the measurement device 11 has a trouble. It is assumed here that the patient obtains the substitute measurement device 11x, and the nursing staff member holding the intermediate device 13 wishes to keep browsing the vital data VD measured before. This embodiment is implemented by making a copy of the data held by the server device 15 and transmitting the copy of the data to the measurement device 11x.

Figure 35:
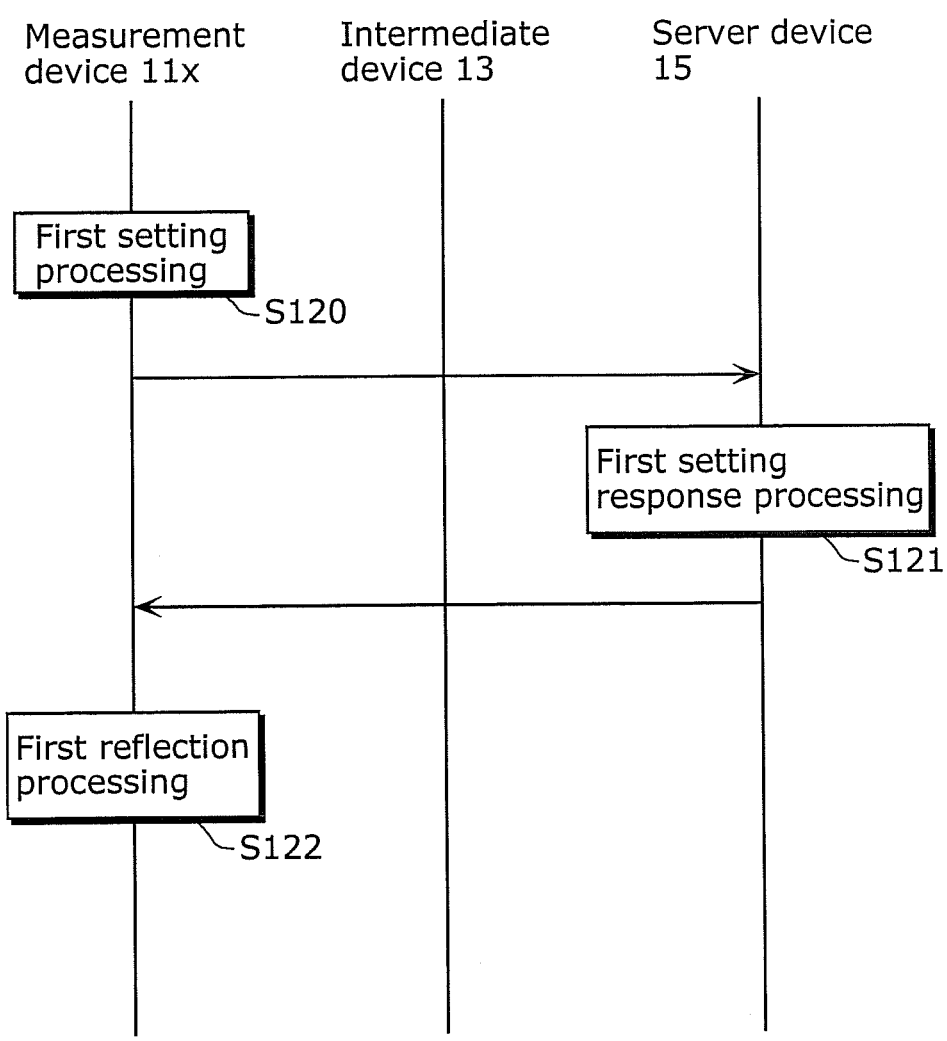
FIG. 35 is a flowchart of exemplary operations at the time of setting a substitute measurement device in the health care system.

Next, with reference to the flowchart in FIG. 35, a description is given of operations for setting the substitute measurement device.

The measurement device 11x performs a "first setting process (Step S120)".

The server device 15 performs a "first setting response process (Step S121)".

The measurement device 11x performs a "first reflection process (Step S122)" to complete the sequential processes.

Next, a description is given of detailed operations performed by the respective structural elements.

Figure 36A:
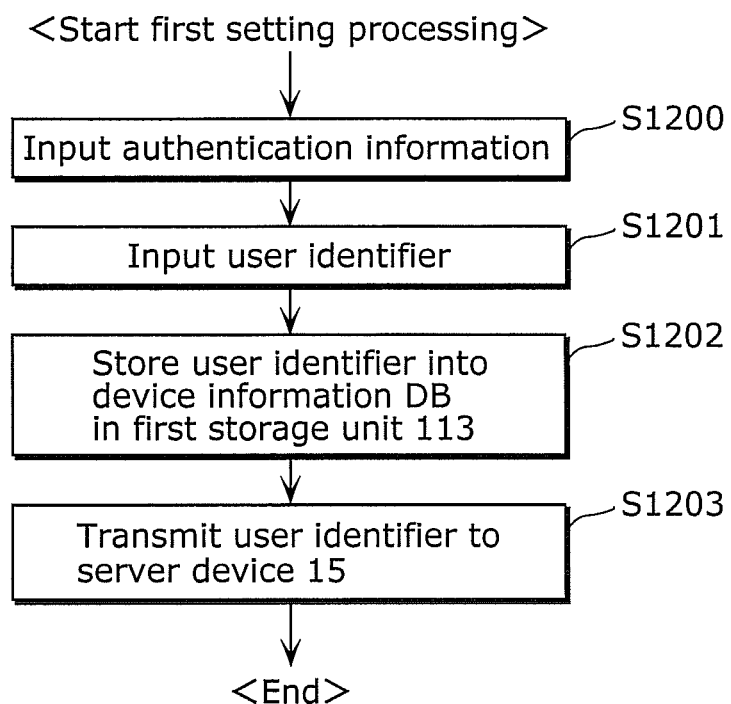
FIG. 36A is a flowchart showing details of the "first setting processing" performed by the measurement device.

[Details of First Setting Process (Step S120): see FIG. 36A]

The first setting processing unit 118 receives an input of authentication information (Step S1200).

When the authentication information is correct, the first setting processing unit 118 receives an input of a user identifier ID (Step S1201).

The first setting processing unit 118 stores the user identifier ID into the device information DB 173 in the first storage unit 113 (Step S1202).

The first setting processing unit 118 transmits the user identifier ID to the server device 15 (Step S1203).

Figure 36B:
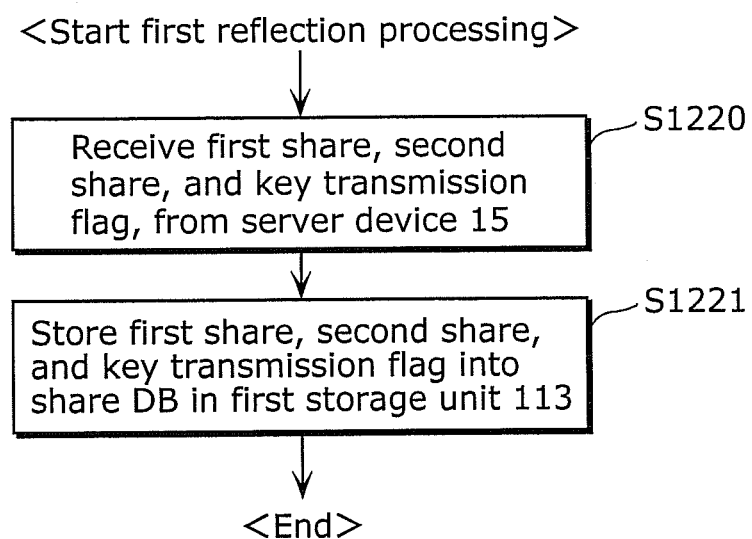
FIG. 36B is a flowchart showing details of the "first reflection processing" performed by the measurement device.

[Details of First Reflection Process (Step S122): see FIG. 36B]

The first setting processing unit 118 receives, from the server device 15, the first share FSD, the second share SSD, and the key transmission flag SF (Step S1220).

The first setting processing unit 118 stores the first share FSD, the second share SSD, and the key transmission flag SF into the share DB 170 in the first storage unit 113 (Step S1221).

Figure 37:
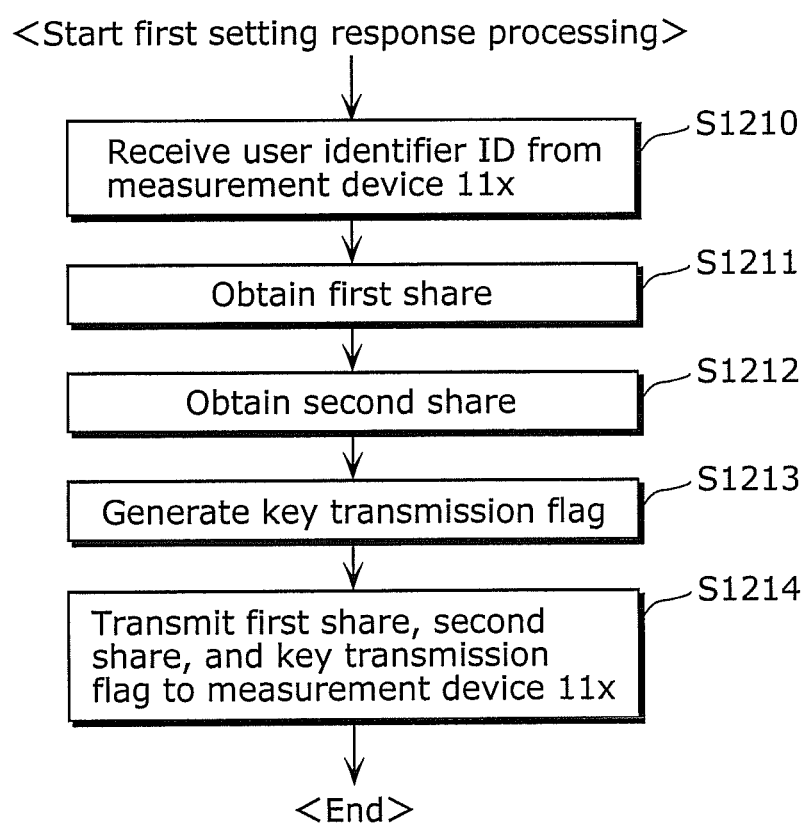
FIG. 37 is a flowchart showing details of "first setting response processing" performed by the server device.

[Details of First Setting Response Process (Step S121): see FIG. 37]

The third setting processing unit 157 receives the user identifier ID from the measurement device 11x(Step S1210).

The third setting processing unit 157 obtains the first share FSD corresponding to the user identifier ID from the third storage unit 152 (Step S1211).

The third setting processing unit 157 obtains the second share SSD corresponding to the user identifier ID from the fourth storage unit 153 (Step S1212).

The third setting processing unit 157 generates the key transmission flag SF having a value indicating Yes (Step S1213).

The third setting processing unit 157 transmits the first share FSD, the second share SSD, and the key transmission flag SF to the measurement device 11x(Step S1214).

[(iv) Operations Performed to Set Share into Intermediate Device 13y when Intermediate Device in Use has Trouble]

Figure 38:
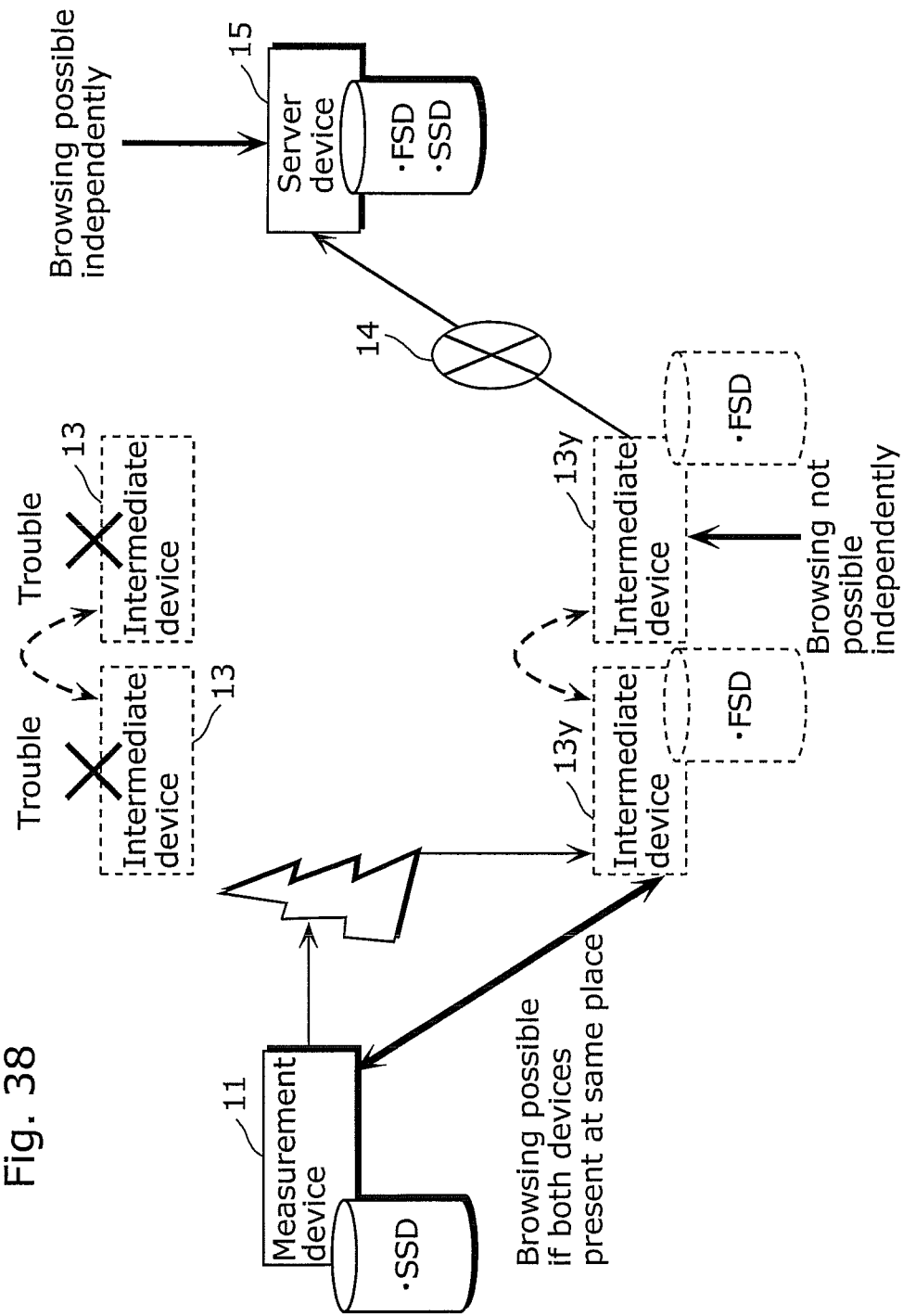
FIG. 38 is another diagram showing a concept of operations in the health care system.

Hereinafter, a description is given of operations for setting a substitute measurement device. First, with reference to FIG. 38, backgrounds of the operations are described in detail again. Here, it is assumed that the intermediate device 13 has a trouble. It is assumed here that the nursing staff member obtains the intermediate device 13y that is a substitute, and wishes to keep browsing the vital data measured before, when establishing communication with the same measurement device 11. Here, such browsing of the previous vital data is possible by copying the data held by the server device 15 and transmitting the data to the intermediate device 13y.

Figure 39:
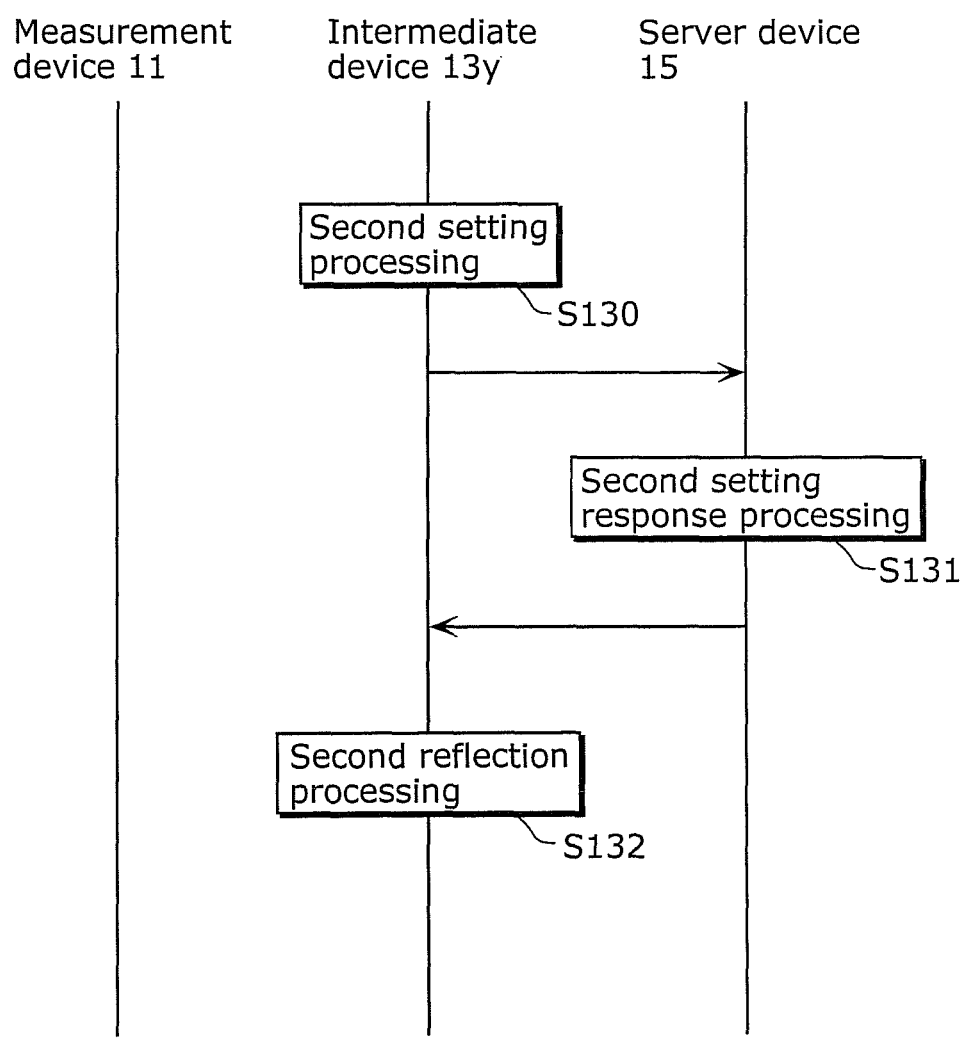
FIG. 39 is a flowchart of exemplary operations at the time of setting a substitute intermediate device in the health care system.

Hereinafter, with reference to a flowchart in FIG. 39, descriptions are given of operations for setting the substitute intermediate device.

The intermediate device 13y performs a "second setting process (Step S130)".

The server device 15 performs a "second setting response process (Step S131)".

The intermediate device 13y performs a "second reflection process (Step S132)" to complete the sequential processes.

Next, a description is given of operations performed by the respective structural elements to set the substitute intermediate device.

Figure 40A:
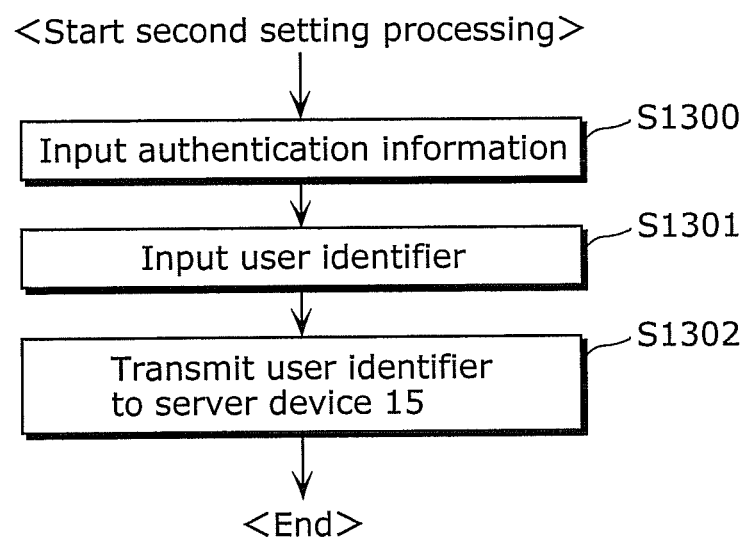
FIG. 40A is a flowchart showing details of "second setting processing" performed by the intermediate device.

[Details of Second Setting Process (Step S130): see FIG. 40A]

The second setting processing unit 139 receives an input of authentication information (Step S1300).

When the authentication information is correct, the second setting processing unit 139 receives an input of a user identifier ID (Step S1301).

The second setting processing unit 139 transmits the user identifier ID to the server device 15 (Step S1302).

Figure 40B:
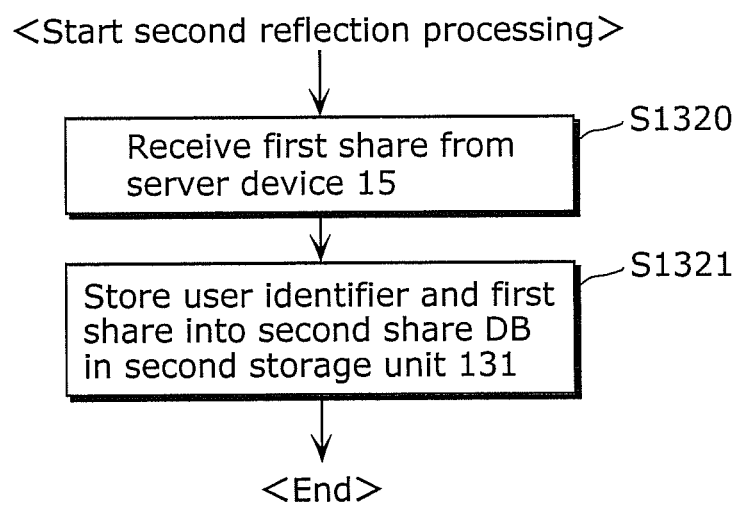
FIG. 40B is a flowchart showing details of "second reflection processing" performed by the intermediate device.

[Details of Second Reflection Process (Step S132): see FIG. 40B]

The second setting processing unit 139 receives, from the server device 15, the first share FSD and the second share SSD (Step S1320).

The second setting processing unit 139 stores the user identifier ID and the first share FSD into the second share DB 180 in the second storage unit 131 (Step S1321).

Figure 41:
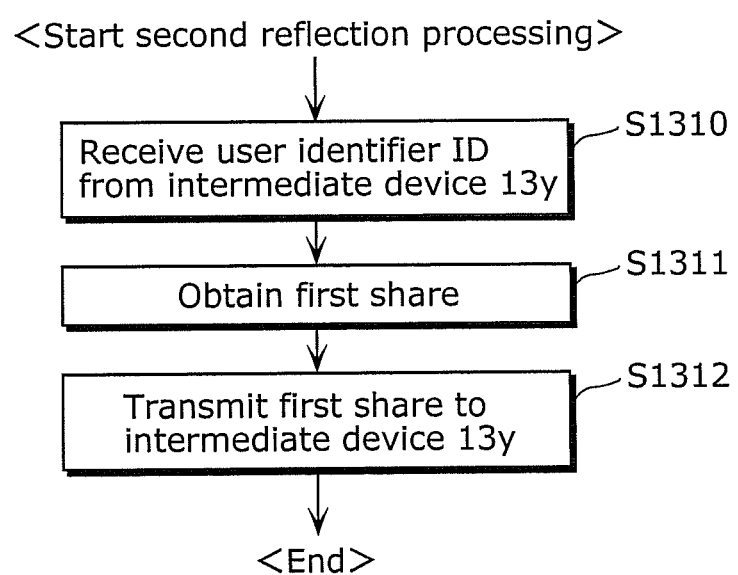
FIG. 41 is a flowchart showing details of "second setting response processing" performed by the server device.

[Details of Second Setting Response Process (Step S131): see FIG. 41A]

The third setting processing unit 157 receives the user identifier ID from the intermediate device 13y (Step S1310).

The third setting processing unit 157 obtains the first share FSD corresponding to the user identifier ID from the third storage unit 152 (Step S1311).

The third setting processing unit 157 transmits the first share FSD to the intermediate device 13y (Step S1312).

The above descriptions have been given of the exemplary operations performed by the measurement device 11, the intermediate device 13, and the sever device 15 which are structural elements of the health care system according to an aspect of the present invention.

(Advantageous Effect of Embodiment 1)

The measurement device 11 holds the first share FSD, the intermediate device 13 stores the second share SSD, and the server device 15 stores the first share FSD and the second share SSD. In this way, the server device 15 can reproduce the decryption key SK from the first share FSD and the second share SSD, and thus can reproduce the vital data VD encrypted using the encryption key PK. On the other hand, the intermediate device 13 cannot reproduce the decryption key SK because the intermediate device 13 holds only the second share SSD. At the time of obtainment of the first share FSD from the measurement device 11, the intermediate device 13 has both the first share FSD and the second share SSD, and thus the intermediate device 13 can reproduce the decryption key SK, and reproduce and display the vital data VD encrypted using the encryption key PK. In other words, only the second share SSD among the shares is stored in the intermediate device 13, and thus the intermediate device 13 can reproduce the vital data VD only when the intermediate device 13 obtains the first share FSD from the measurement device 11. For this reason, it is impossible to display the vital data VD on the display unit 132 of the intermediate device 13 when the measurement device 11 and the intermediate device 13 are not present at a same place. Since it is impossible for a third party to see the vital data VD using only the intermediate device 13, it is possible to prevent the vital data VD from being seen by the third party at a place unknown by the patient. Accordingly, it is possible to securely distribute the share even when it is impossible to directly transmit the share from the measurement device 11 to the server device 15. In addition, it is possible to prevent leakage of the vital data VD to the outside even when the intermediate device 13 is lost because it is impossible to display the vital data VD on the display unit of the intermediate device 13 when the measurement device 11 and the intermediate device 13 are not present at a same place. Furthermore, the use of the technique of the secret sharing scheme makes it possible to completely prevent the risk of leakage of the secret.

The server device 15 holds the first share FSD and the second share SSD even after the decryption key SK is reproduced. This makes it possible to set the first share FSD to a suitable measurement device 11x, and further to set the second share SSD to a suitable intermediate device 13y. In this way, even when either the measurement device 11 or the intermediate device 13 has a trouble, it is possible to set the same second share SSD into the intermediate device 13y. In this way, according to a method similar to the above-described method, it is possible to control the browsing of the vital data VD even when either the measurement device 11 in use by the patient or the intermediate device 13 in use by the nursing staff member has a trouble.

Embodiment 2

Hereinafter, Embodiment 2 of the present invention will be described with reference to the drawings.

Figure 42:
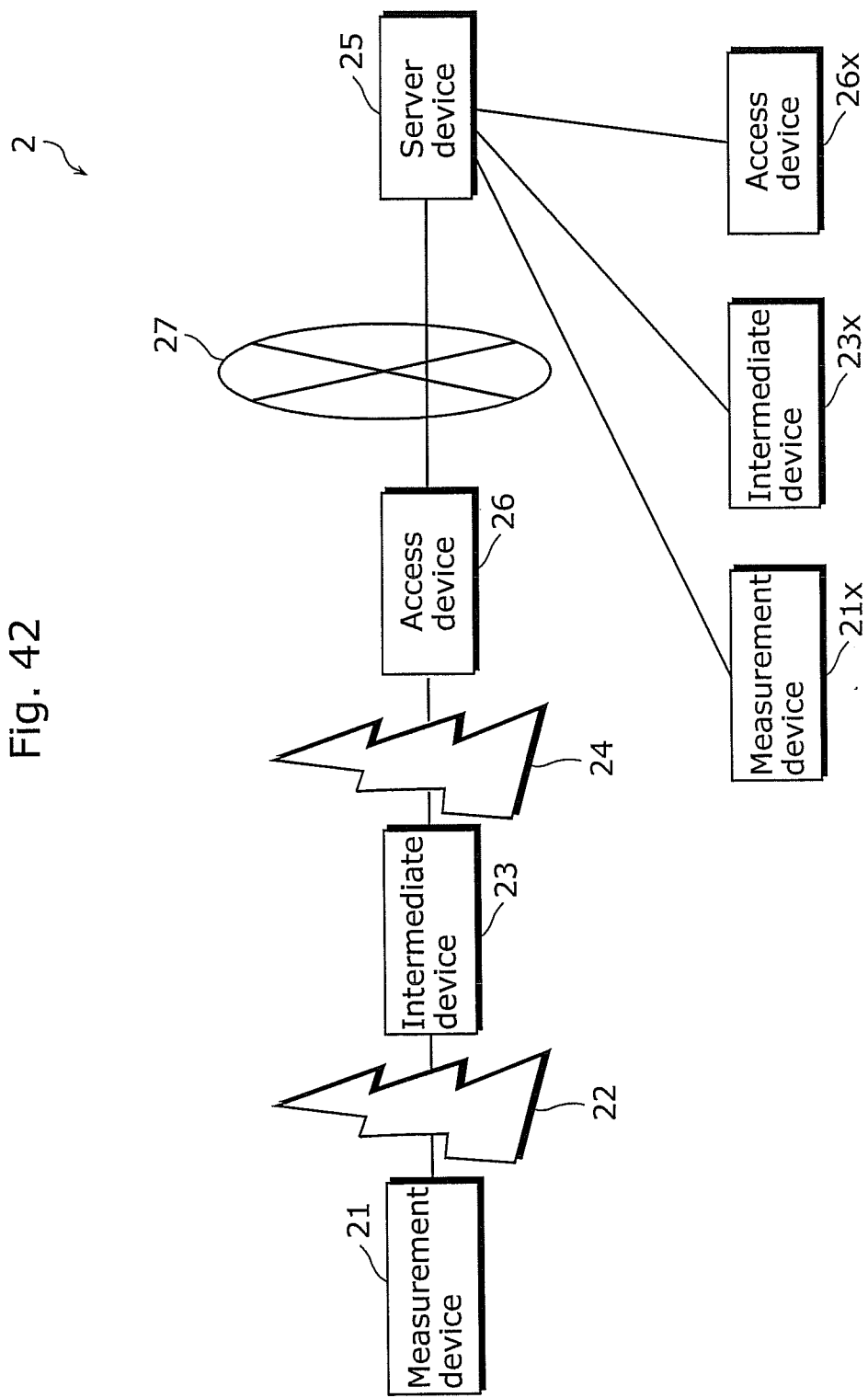
FIG. 42 is a block diagram showing a structure of a health care system according to Embodiment 2 of the present invention.

FIG. 42 is a diagram showing a structure of a health care system 2.

The health care system 2 includes a measurement device 21, an intermediate device 23, a server device 25, and an access device 26. The measurement device 21 and the intermediate device 23 are connected via a first computer network 22. The intermediate device 23 and the access device 26 are connected via a second computer network 24. The access device 26 and the server device 25 are connected via a third computer network 27. The large difference from Embodiment 1 is that the access device 26 is added. This access device 26 is, for example, a device that is placed in either an employment agency (nursing station) to which a nursing staff member belongs or the home of the nursing staff member. This access device 26 has two major functions of: passing, to the server device 25, data passed from the measurement device 21 to the intermediate device 23; and allowing the browsing of patient's vital data when the intermediate device 23 and the access device 26 establish a communication with each other.

The first computer network 22, the second computer network 24, and the third computer network 27 are described first, and then the structures of the measurement device 21, the intermediate device 23, the server device 25, and the access device 26 are described with reference to the drawings.

[Structure of First Computer Network 22]

The first computer network 22 is a computer network for transmission and reception of various kinds of data between the measurement device 21 and the intermediate device 23. Examples of the first computer network 22 include a computer network for wireless connection that is established by Bluetooth (trademark), and a computer network for wired connection that is established using a Universal Serial Bus (USB).

[Structure of Second Computer Network 24]

The second computer network 24 is a computer network for transmission and reception of various kinds of data between the intermediate device 23 and the access device 26. Examples of the second computer network 24 include a computer network for wireless connection that is established by Bluetooth (trademark), and a computer network for wired connection that is established using a Universal Serial Bus (USB).

[Structure of Third Computer Network 27]

The third computer network 27 is a computer network for transmission and reception of various kinds of data between the access device 26 and the server device 25. For example, the third computer network 27 is implemented in the form of either the Asymmetric Digital Subscriber Line (ADSL), a telephone line, a dedicated line, or the like.

[Structure of Measurement Device 21]

Next, the structure of the measurement device 21 is described.

Figure 43:
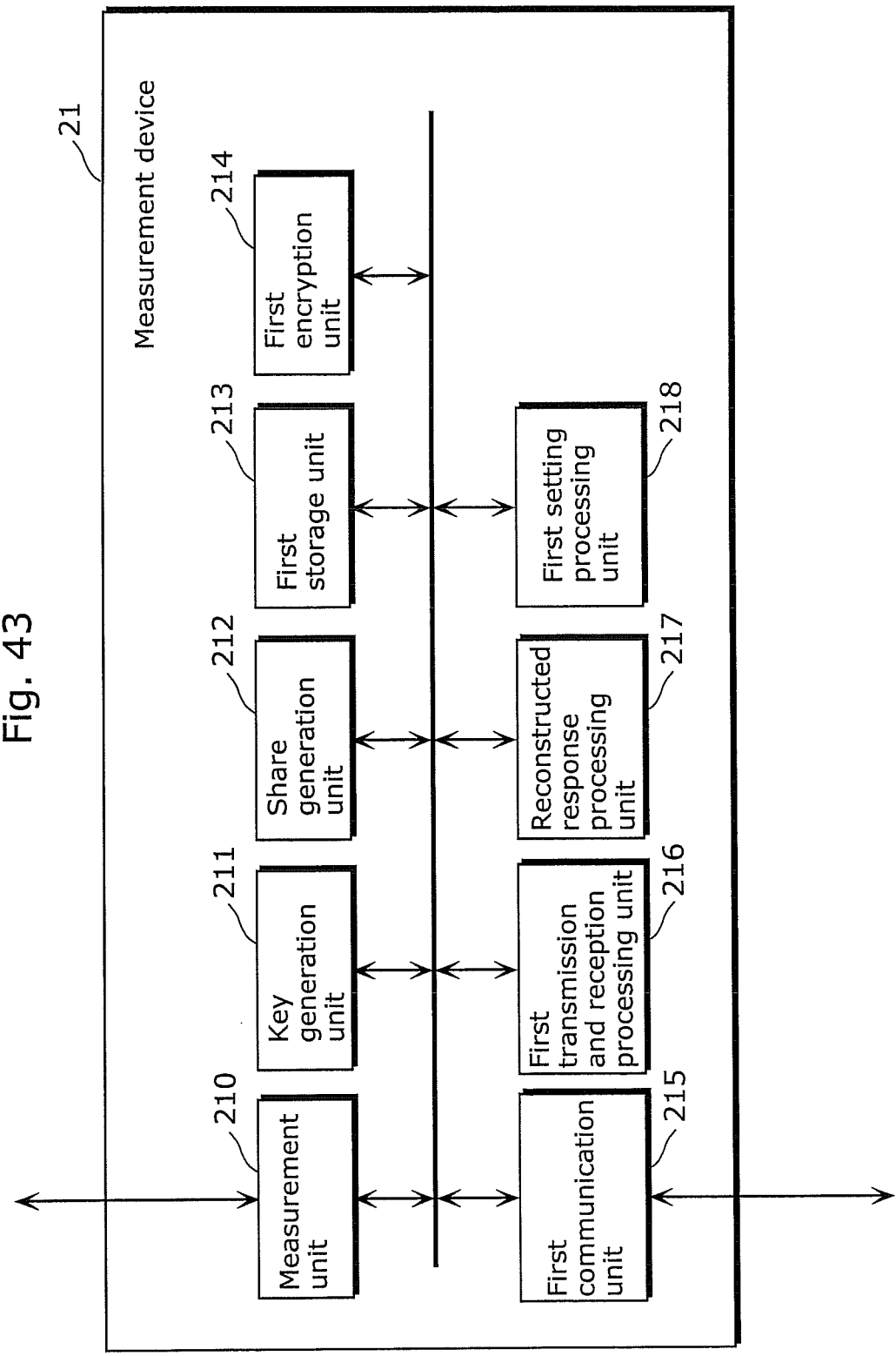
FIG. 43 is a block diagram showing a structure of a measurement device.

FIG. 43 is a block diagram showing a structure of the measurement device 21. As shown in FIG. 43, the measurement device 21 includes a measurement unit 210, a key generation unit 211, a share generation unit 212, a first storage unit 213, a first encryption unit 214, a first communication unit 215, a first transmission and reception processing unit 216, a reconstructed response processing unit 217, and a first setting processing unit 218. Among these structural elements, the essential structural elements are the measurement unit 210, the share generation unit 212, the first encryption unit 214, and the first communication unit 215.

It is to be noted that the measurement unit 210, the share generation unit 212, and the first communication unit 215 respectively correspond to a measurement unit, a share generation unit, and a first communication unit in the CLAIMS of the present application. In addition, the first encryption unit 214 corresponds to a vital data encryption unit, a first share encryption unit, a second share encryption unit, and a third share encryption unit in the CLAIMS of the present application.

(1) Measurement Unit 210

The measurement unit 210 measures vital data VD of a patient. Examples of vital data VD include weight, body fat, body temperature, blood pressure, blood sugar level, pulse, heart beat, the number of steps taken, and activities quantity. In the case where the vital data VD is the body temperature, the data size of the vital data VD is 3 bytes (1 byte for each of the tens place, ones place, and tenths place). The measurement device 21 includes a "measure button", and the measurement unit 210 has a function for measuring vital data VD when the button is pressed. It is to be noted that the measurement unit 210 has a clock function, and may add the measurement time to the vital data VD. As an example, when the body temperature measured at 11:26 on Oct. 16, 2008 is 36.5 degrees Celsius, the vital data VD is "10/16/2008 11:26 365". The measurement unit 210 outputs the generated vital data VD to another one of the functional blocks.

(2) Key Generation Unit 211

The key generation unit 211 generates an encryption key PK and a decryption key SK that are a pair of keys in public key encryption, when the encryption key PK and the decryption key SK are not set in the encryption key DB in the first storage unit 213. The public key encryption is, for example, Rivest Shamir Adleman (RSA) scheme, the elliptic curve cryptography scheme, or the like. The RSA scheme, the elliptic curve cryptography scheme, and the key generation methods according to the schemes are publicly known, thus no detailed descriptions are given here. The key generation unit 111 stores the encryption key PK and the decryption key SK into the encryption key DB in the first storage unit 213. For example, the key generation unit 211 may generate the encryption key PK and the decryption key SK when the measurement device 21 is firstly activated, or may generate these keys when the vital data VD is firstly measured by the measurement unit 210. It is to be noted that the key generation unit 211 may not always be included in the measurement device 21. In other words, the measurement device 21 may receive the encryption key PK and the decryption key SK from a device outside the measurement device 11.

(3) Share Generation Unit 212

After the key generation unit 211 generates the pair of keys, the share generation unit 212 generates three mutually different shares from the decryption key SK that is set in the encryption key DB in the first storage unit 213 according to the secret sharing scheme. Here, the original information can be reconstructed when two of the three shares are obtained.

(4) First Storage Unit 213

Figure 44:
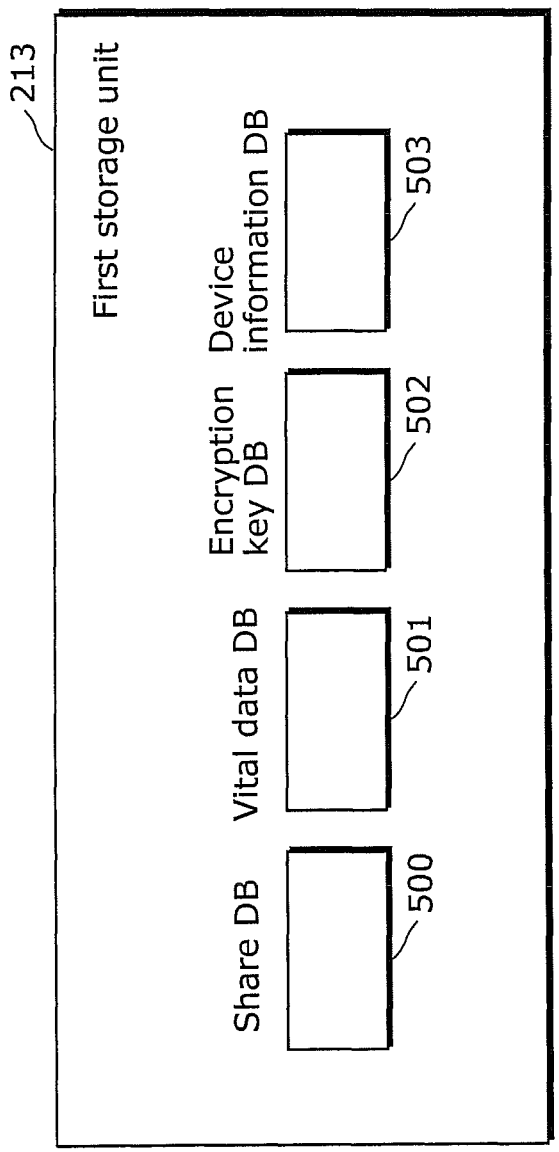
FIG. 44 is a block diagram showing a structure of a first storage unit of the measurement device.

As shown in FIG. 44, the first storage unit 213 holds a share DB 500, a vital data DB 501, an encryption key DB 502, and a device information DB 503.

Figure 45:
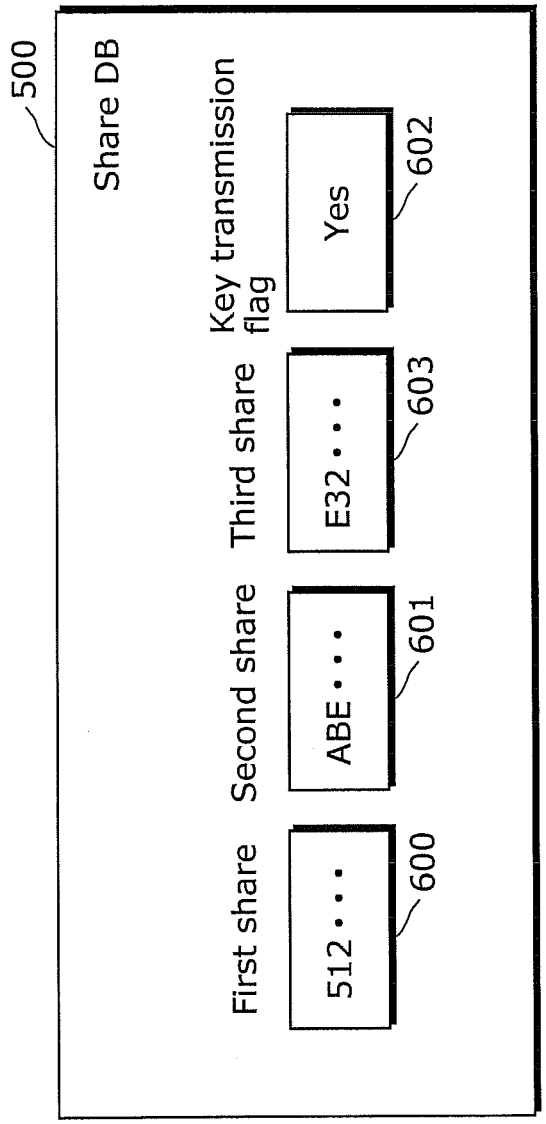
FIG. 45 is a diagram showing a structure of the share DB in the first storage unit of the measurement device.

As shown in FIG. 45, the share DB 500 includes a first share FSD (a first share 600 in FIG. 45), a second share SSD (a second share 601 in FIG. 45), a third share TSD (a third share 603 in FIG. 45), and a key transmission flag SF (a key transmission flag 602 in FIG. 45). Each of the first share FSD, the second share SSD, and the third share TSD is a value generated when the share generation unit 212 performs sharing on the decryption key SK generated by the key generation unit 211. The key transmission flag SF is a value indicating whether or not each of the first share FSD, the second share SSD, and the third share TSD is already passed to the intermediate device 23. Here, "Yes" represents "Already transmitted", and "No" represents "Not yet transmitted". The key transmission flag SF is used when the measurement device 21 judges whether or not to transmit the first share FSD, the second share SSD, and the third share TSD to the intermediate device 23.

Figure 46:
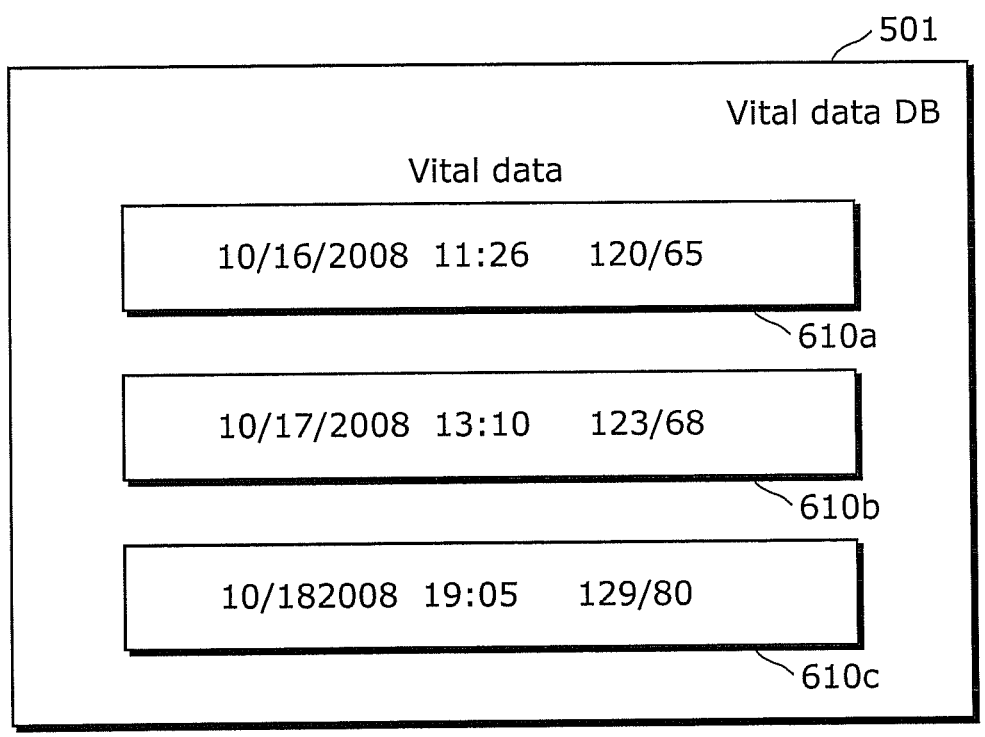
FIG. 46 is a diagram showing a structure of a vital data DB in the first storage unit of the measurement device.

As shown in FIG. 46, the vital data DB 501 includes one or more vital data VD (vital data 610*a*, 610*b*, and 610*c* in FIG. 46). Each of the vital data VD is vital data measured by the measurement unit 210.

Figure 47:
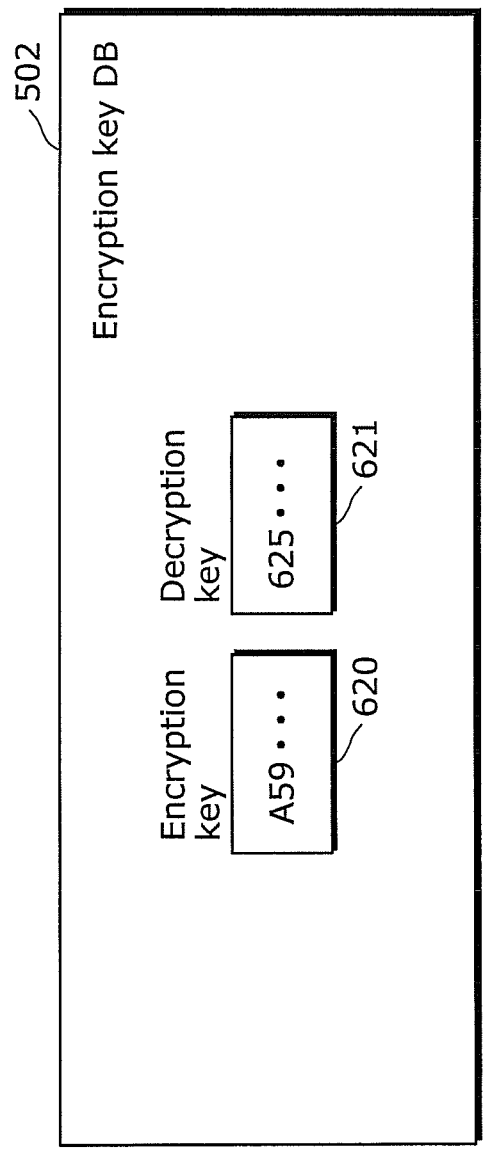
FIG. 47 is a diagram showing a structure of an encryption key DB in the first storage unit of the measurement device.

As shown in FIG. 47, the encryption key DB 502 includes the encryption key PK (an encryption key 620 in FIG. 47) and the decryption key SK (a decryption key 621 in FIG. 47). The encryption key PK and the decryption key SK are generated by the key generation unit 211.

Figure 48:
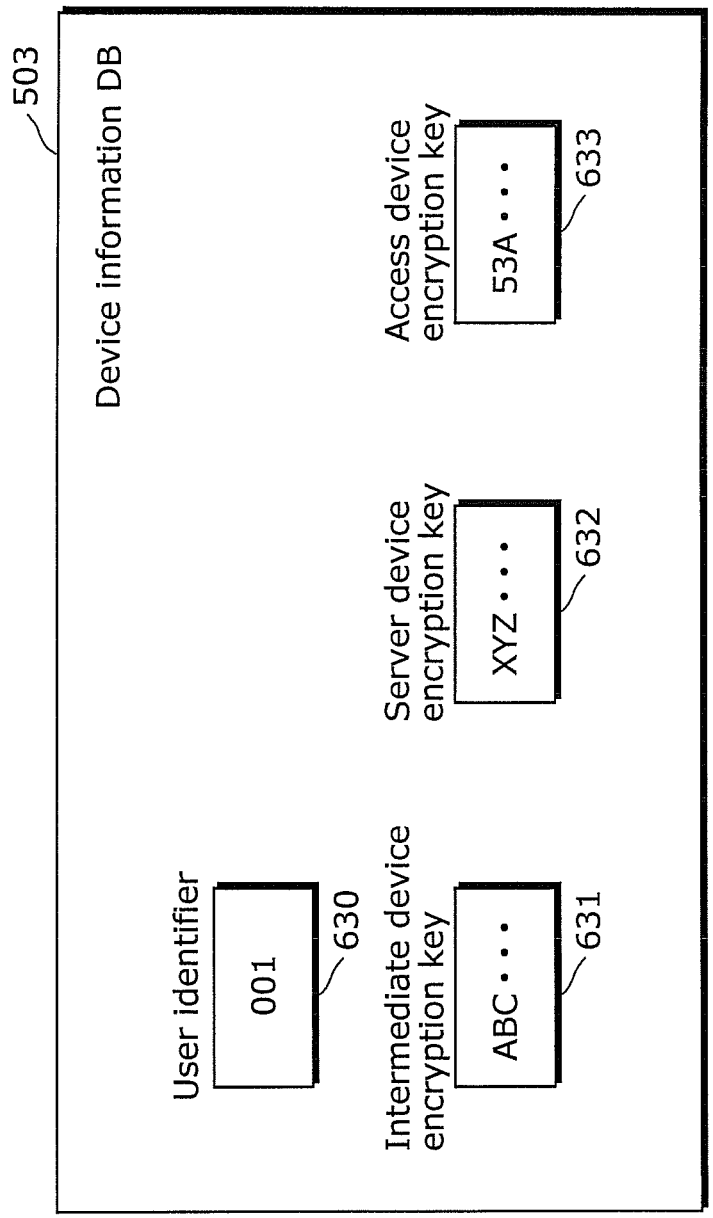
FIG. 48 is a block diagram showing a structure of a device information DB of the first storage unit of the measurement device.

As shown in FIG. 48, the device information DB 503 includes a user identifier ID (a user identifier 630 in FIG. 48), an intermediate device encryption key CPK (an intermediate device encryption key 631 in FIG. 48), a server device encryption key (a server device encryption key 632 in FIG. 48), and an access device key encryption key (an access device encryption key 633 in FIG. 48). The user identifier ID is a number identifying the patient who holds the measurement device 21. The intermediate device encryption key CPK is a key corresponding to the intermediate device decryption key CSK held by the intermediate device 23, and the server device encryption key SPK is a key corresponding to the server device decryption key SSK held by the server device 25. The access device encryption key APK is a key corresponding to an access device decryption key ASK held by the access device 26.

(5) First Encryption Unit 214

The first encryption unit 214 has the following two functions.

A. Encryption of Vital Data VD

Upon receiving the vital data VD from the one of the functional blocks, the first encryption unit 214 accesses the encryption key DB 502 in the first storage unit 213, and obtains the encryption key PK. Next, the first encryption unit 214 encrypts the vital data VD using the encryption key PK. The vital data VD encrypted is referred to as vital data EVD encrypted. The same encryption scheme as the scheme used by the key generation unit 211 to generate the pair of keys is employed here. For example, the encryption scheme is the RSA scheme or the elliptic curve cryptography scheme. Next, the first encryption unit 214 outputs the vital data EVD encrypted to the one of the functional blocks.

B. Encryption of Shares

Upon receiving the first share FSD, the second share SSD, and the third share TSD from the one of the functional blocks, the first encryption unit 214 accesses the device information DB 503 in the first storage unit 213, and obtains the intermediate device encryption key CPK. Next, the first encryption unit 214 encrypts the first share FSD using the intermediate device encryption key CPK. Subsequently, the first encryption unit 214 accesses the device information DB 503 in the first storage unit 213, and obtains the server device encryption key SPK. Next, the first encryption unit 214 encrypts the second share SSD using the server device encryption key SPK. Lastly, the first encryption unit 214 accesses the device information DB 503 in the first storage unit 213 again, and obtains the access device encryption key APK. Next, the first encryption unit 214 encrypts the third share TSD using the access device encryption key APK. The first share FSD encrypted, the second share SSD encrypted, and the third share TSD encrypted are also referred to as an encrypted first share EFSD, an encrypted second share ESSD, and an encrypted third share ETSD, respectively. For example, the encryption scheme is the RSA scheme or the elliptic curve cryptography scheme. Next, the first encryption unit 214 outputs the encrypted first share EFSD, the encrypted second share ESSD, and the encrypted third share ETSD to the one of the functional blocks.

(6) First Communication Unit 215

The first communication unit 215 has a function for transmitting and receiving various kinds of data to and from the intermediate device 23 via the first computer network 22, in response to the request from the one of the functional blocks.

(7) First Transmission and Reception Processing Unit 216

Figure 49:
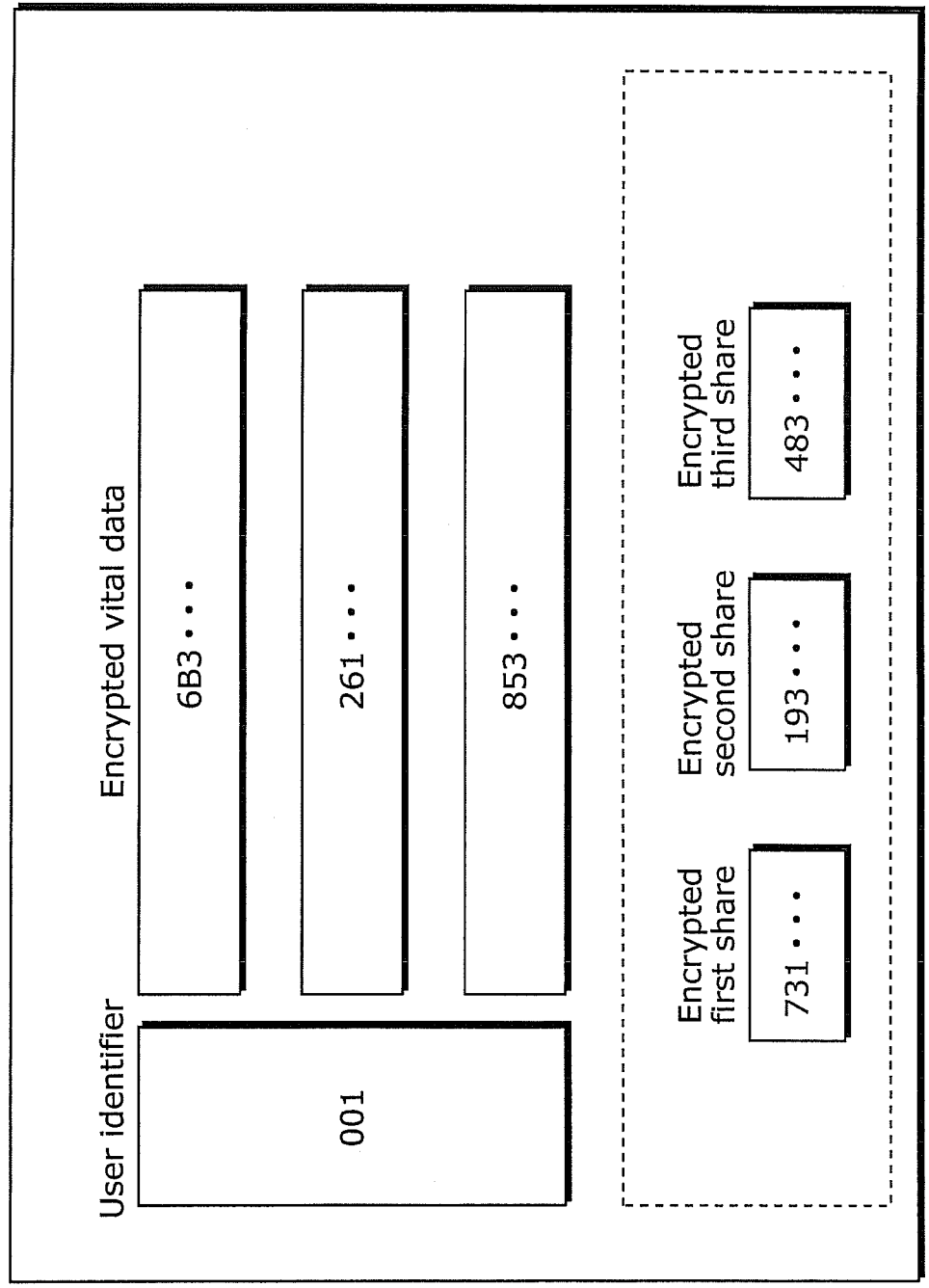
FIG. 49 is a diagram showing a structure of a first data FD.

The first transmission and reception processing unit 216 generates first data FD including a user identifier ID and one or more encrypted vital data EVD as shown in FIG. 49, in response to the request from the outside. For example, the measurement device 21 includes a "transmission button", and the first transmission and reception processing unit 216 generates the first data FD when the button is pressed. The first transmission and reception processing unit 216 obtains the user identifier ID from the device information DB 503 in the first storage unit 213. The encrypted vital data EVD is data that is obtained when the first encryption unit 214 encrypts the vital data VD. In the encryption, when the key transmission flag SF stored in the share DB 500 in the first storage unit 213 indicates "No", the first transmission and reception processing unit 216 makes an additional request to the first encryption unit 214 to generate the encrypted first share EFSD, the encrypted second share ESSD, and the encrypted third share ETSD. Next, the first transmission and reception processing unit 216 includes, in the first data FD, the encrypted first share EFSD, the encrypted second share ESSD, and the encrypted third share ETSD. Next, the first transmission and reception processing unit 216 transmits the generated first data FD to the intermediate device 23 via the first communication unit 215.

(8) Reconstructed Response Processing Unit 217

When the reconstructed response processing unit 217 receives the user identifier ID from the intermediate device 23 via the first communication unit 215, the reconstructed response processing unit 217 accesses the device information DB 503 in the first storage unit 213 first, and checks whether or not the received user identifier ID is the same as the user identifier ID stored in the device information DB 503. When the both are the same, the reconstructed response processing unit 217 obtains the second share SSD from the share DB 500 in the first storage unit 213, and transmits the second share SSD to the intermediate device 23 via the first communication unit 215.

(9) First Setting Processing Unit 218

The first setting processing unit 218 has a function for setting the user identifier ID, the intermediate device encryption key CPK, and the server device encryption key SPK, to the device information DB 503 in the first storage unit 213, based on the data that is input from the outside. For example, the first setting processing unit 218 may set the pieces of information based on the data that is input using a keyboard, or may be set based on data stored in a memory card such as a Secure Digital (SD) card. In addition, the first setting processing unit 218 includes a predetermined authentication function (such as password authentication), and performs authentication when the measurement device 21 establishes a connection with the server device 25. When the predetermined authentication is successfully performed, the server device 25 is capable of setting the first share FSD, the second share SSD, the third share TSD, and the key transmission flag SF, into the share DB 500 in the first storage unit 213 via the first setting processing unit 218.

[Structure of Intermediate Device 23]

Figure 50:
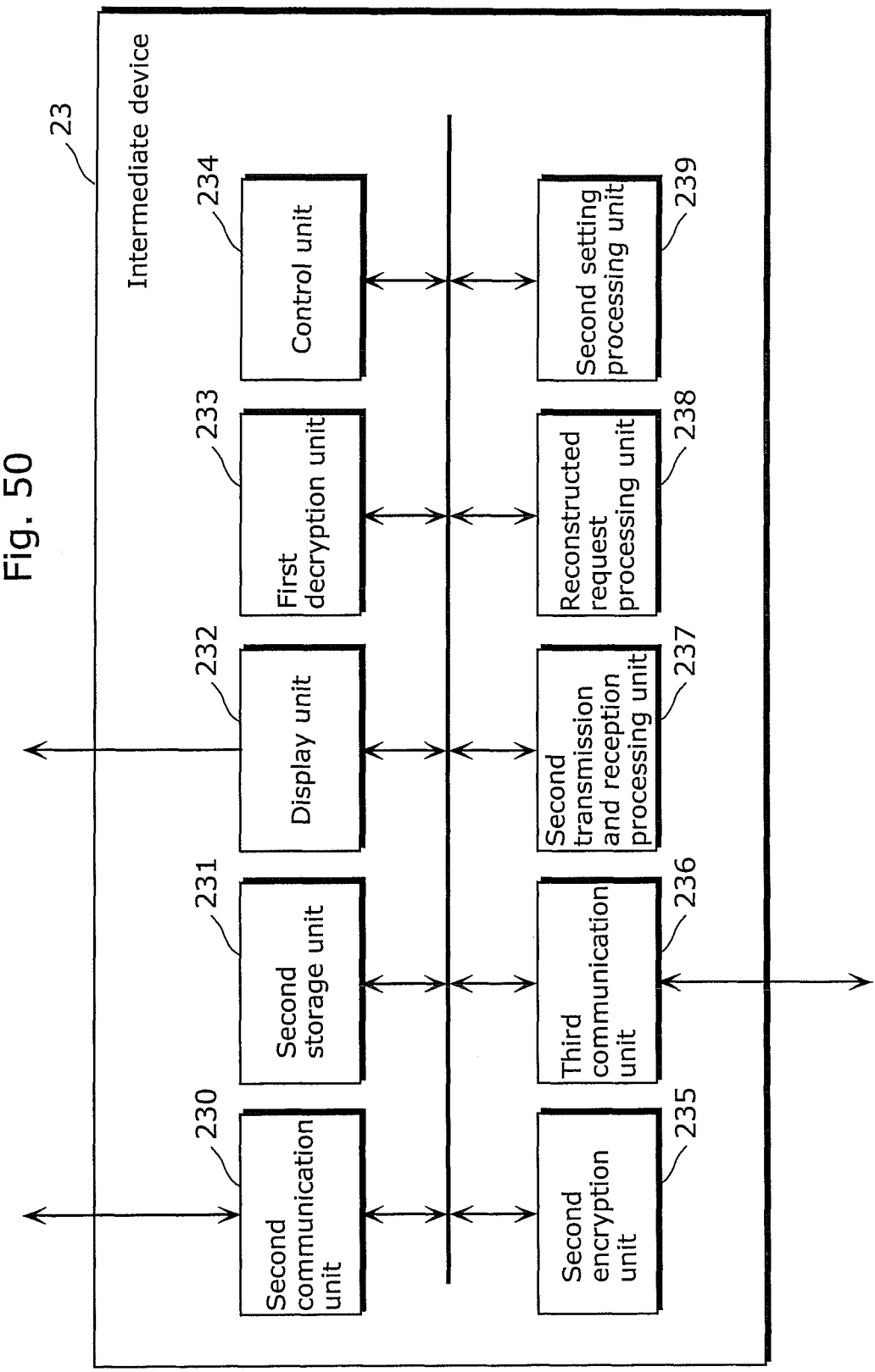
FIG. 50 is a block diagram showing a structure of an intermediate device.

Next, the structure of the intermediate device 23 is described. FIG. 50 is a block diagram showing the structure of the intermediate device 23. As shown in FIG. 50, the intermediate device 23 includes a second communication unit 230, a second storage unit 231, a display unit 232, a first decryption unit 233, a control unit 234, a second encryption unit 235, a third communication unit 236, a second transmission and reception processing unit 237, a reconstructed request processing unit 238, and a second setting processing unit 239. Among the structural elements, the essential elements are the second communication unit 230 and the third communication unit 236.

It is to be noted that the second communication unit 230, the display unit 232, and the third communication unit 236 respectively correspond to a second communication unit, a display unit, and a third communication unit in the CLAIMS of the present application. In addition, the second storage unit 231 corresponds to a storage unit in the CLAIMS of the present application. Furthermore, the first decryption unit 233 corresponds to a vital data decryption unit at the intermediate device side in the CLAIMS of the present application. Furthermore, the second encryption unit 235 corresponds to a first share decryption unit in the CLAIMS of the present application.

(1) Second Communication Unit 230

The second communication unit 230 has a function for transmitting and receiving various kinds of data to and from the measurement device 21 via the first computer network 22.

(2) Second Storage Unit 231

Figure 51:
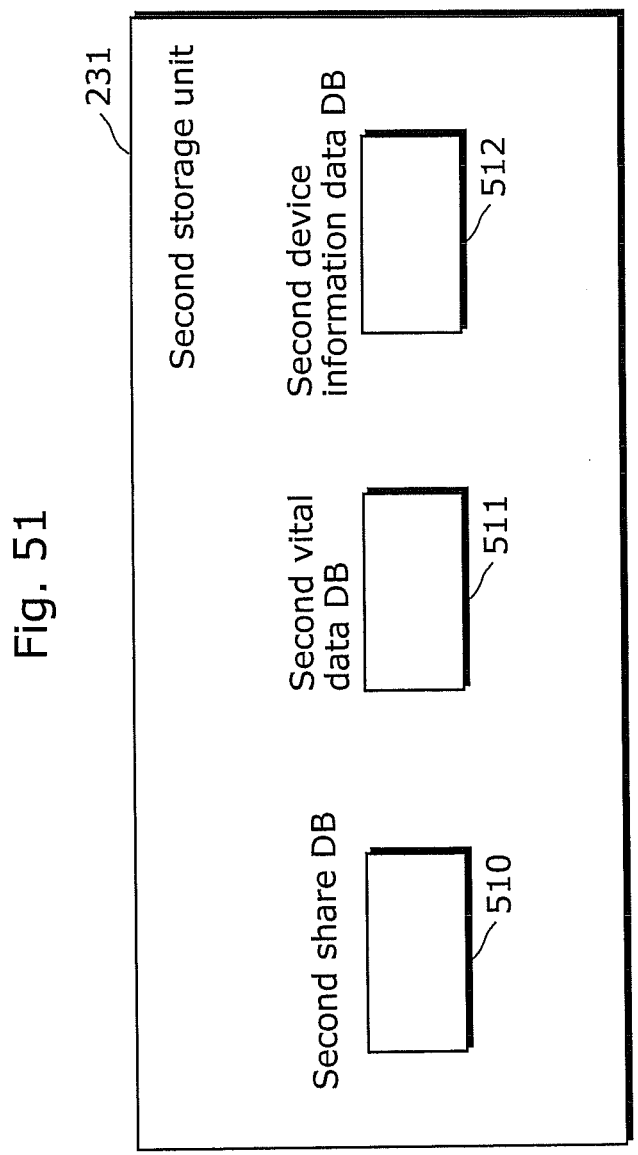
FIG. 51 is a diagram showing a structure of a second storage unit of the intermediate device.

As shown in FIG. 51, the second storage unit 231 holds a second share DB 510, a second vital data DB 511, and a second device information DB 512.

Figure 52:
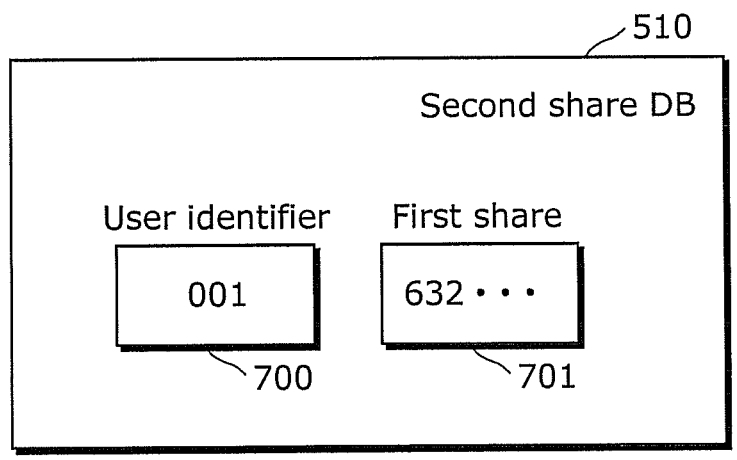
FIG. 52 is a diagram showing a structure of the second share DB in a second storage unit of the intermediate device.

As shown in FIG. 52, the second share DB 510 includes a user identifier ID (a user identifier 700 in FIG. 52) and a first share FSD (a first share 701 in FIG. 52).

Figure 53:
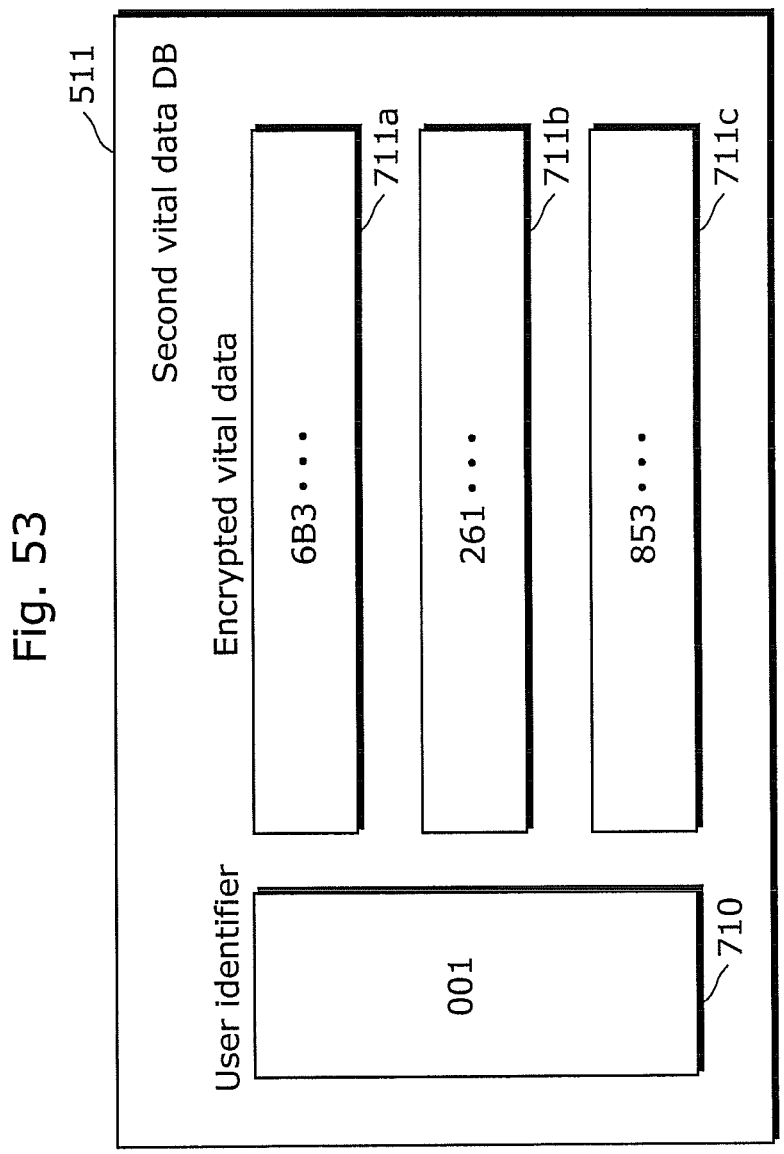
FIG. 53 is a diagram showing a structure of a second vital data DB in the second storage unit of the intermediate device.

As shown in FIG. 53, the second vital data DB 511 includes a user identifier ID (a user identifier 710 in FIG. 53) and one or more encrypted vital data EVD (encrypted vital data 711a, 711b, and 711c).

Figure 54:
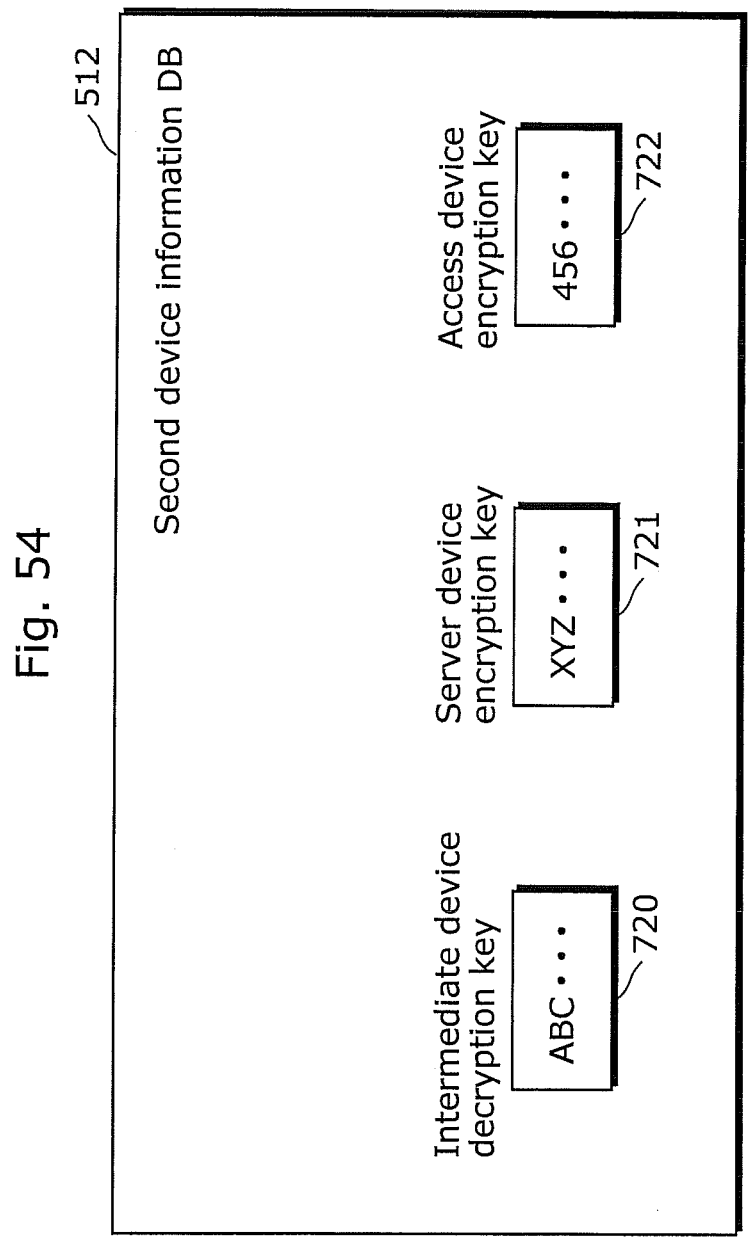
FIG. 54 is a diagram showing a structure of a second device information DB in the second storage unit of the intermediate device.

As shown in FIG. 54, the second device information DB 512 includes an intermediate device decryption key CSK (an intermediate device decryption key 720 in FIG. 54), a server device encryption key SPK (a server device encryption key 721 in FIG. 54), and an access device encryption key APK (an access device encryption key 722 in FIG. 54).

(3) Display Unit 232

The display unit 232 has a function for displaying vital data VD. For example, the display unit 232 displays a plurality of vital data VD in the form of a graph or a table.

(4) First Decryption Unit 233

When the first decryption unit 233 receives the encrypted vital data EVD and two of the first share FSD, the second share SSD, and the third share TSD, the first decryption unit 233 reconstructs the decryption key SK from the two of the shares first according to the secret sharing scheme. Next, the first decryption unit 233 decrypts the encrypted vital data EVD using the decryption key SK to obtain the vital data VD. The first decryption unit 233 has a function for outputting the vital data VD.

(5) Control Unit 234

When the control unit 234 receives a user identifier ID from the outside, the control unit 134 outputs the user identifier ID to the reconstructed request processing unit 138. For example, the intermediate device 23 has a "browse button" and a "keyboard", and the user identifier ID is input using the button and the keyboard. In response, the control unit 234 obtains either the second share SSD or the third share TSD from the reconstructed request processing unit 238. Furthermore, the control unit 234 obtains the first share FSD corresponding to the user identifier ID from the second share DB 510 in the second storage unit 231. Furthermore, the control unit 234 obtains the encrypted vital data EVD corresponding to the user identifier ID from the second vital data DB 511 in the second storage unit 231. Next, the control unit 234 outputs the first share FSD, the encrypted vital data EVD, and either the second share SSD or the third share TSD, to the first decryption unit 233, and obtains the vital data VD from the first decryption unit 233. The control unit 134 has a function for causing the display unit 232 to display the vital data VD.

(6) Second Encryption Unit 235

When the second encryption unit 235 receives the user identifier ID and the encrypted first share EFSD, the second encryption unit 235 obtains the intermediate device decryption key CSK from the second device information DB 512 in the second storage unit 231. Next, the second encryption unit 235 decrypts the encrypted first share EFSD using the intermediate device decryption key CSK. The second encryption unit 235 stores the first share FSD that is a decryption result into the second share DB 510 in the second storage unit 231 in such a manner that the first share FSD is associated with the user identifier ID. Subsequently, the second encryption unit 235 obtains the server device encryption key SPK from the second device information DB 512 in the second storage unit 231. Next, the second encryption unit 235 encrypts the first share FSD using the server device encryption key SPK. The result is referred to as the second encrypted first share E2FSD. Lastly, the second encryption unit 235 outputs the second encrypted first share E2FSD to the one of the functional blocks.

(7) Third Communication Unit 236

The third communication unit 236 has a function for transmitting and receiving various kinds of data to and from the access device 26 via the second computer network 24.

(8) Second Transmission and Reception Processing Unit 237

Figure 55:
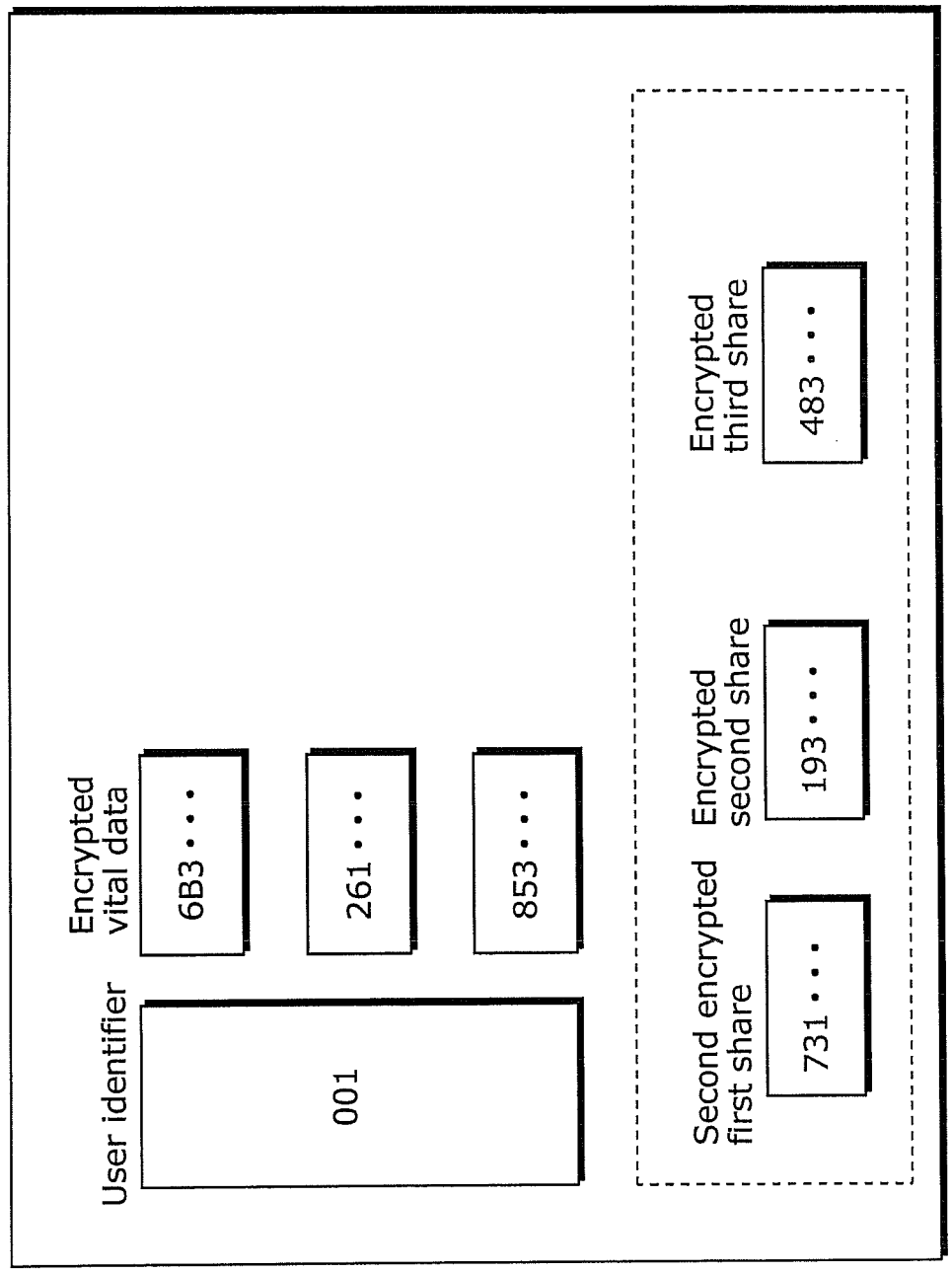
FIG. 55 is a diagram showing a structure of second data SD.

When the second transmission and reception processing unit 237 receives the first data FD from the measurement device 21, the second transmission and reception processing unit 137 firstly stores the user identifier ID and the encrypted vital data EVD included in the first data FD into the second vital data DB 511 in the second storage unit 231. Subsequently, when the encrypted first share EFSD and the second encrypted first share E2FSD are included in the first data FD, the second transmission and reception processing unit 237 outputs the user identifier ID and the encrypted first share EFSD to the second encryption unit 235, and obtains the second encrypted first share E2FSD. As shown in FIG. 55, among the data in the first data FD, the second transmission and reception processing unit 237 generates the second data SD obtained by replacing the encrypted first share EFSD with the second encrypted first share E2FSD. Next, the second transmission and reception processing unit 237 transmits the second data SD to the access device 26 via the third communication unit 236. When the encrypted first share EFSD and the second encrypted first share E2FSD are not included in the first data FD, the second transmission and reception processing unit 237 transmits the first data FD as the second data SD to the access device 26 via the third communication unit 236.

(9) Reconstructed Request Processing Unit 238

The reconstructed request processing unit 238 has the following two functions.

1. When the intermediate device 23 and the measurement device 21 can communicate with each other via the first computer network 22, the reconstructed request processing unit 238 receives the user identifier ID from the one of the functional blocks, and transmits the user identifier ID to the measurement device 21 via the second communication unit 230. Next, the reconstructed request processing unit 238 receives the encrypted second share ESSD from the measurement device 21 via the second communication unit 230. The reconstructed request processing unit 238 outputs the encrypted second share ESSD to the first decryption unit 233.

2. When the intermediate device 23 and the access device 26 can communicate with each other via the second computer network 24, the reconstructed request processing unit 238 receives the user identifier ID from the one of the functional blocks, and transmits the user identifier ID to the access device 26 via the third computer network 236. Next, the reconstructed request processing unit 238 receives the encrypted third share ETSD from the access device 26 via the third communication unit 236. The reconstructed request processing unit 238 outputs the encrypted third share ETSD to the first decryption unit 233.

(10) Second Setting Processing Unit 239

The second setting processing unit 239 is capable of setting the intermediate device decryption key CSK, the server device encryption key SPK, and the access device encryption key APK, into the second device information DB 512 in the second storage unit 231, based on the data that is input from the outside. For example, the intermediate device 23 includes a keyboard, and the second setting processing unit 239 is capable of setting these pieces of information based on the data that is input using the keyboard. In addition, the second setting processing unit 239 includes a predetermined authentication function (such as password authentication), and performs authentication when the intermediate device 23 establishes a connection with the server device 25. When the predetermined authentication is successfully performed, the server device 25 is capable of setting the user identifier ID and the first share FSD into the second share DB 510 in the second storage unit 231 via the second setting processing 239.

[Structure of Access Device 26]

Next, the structure of the access device 26 is described.

Figure 56:
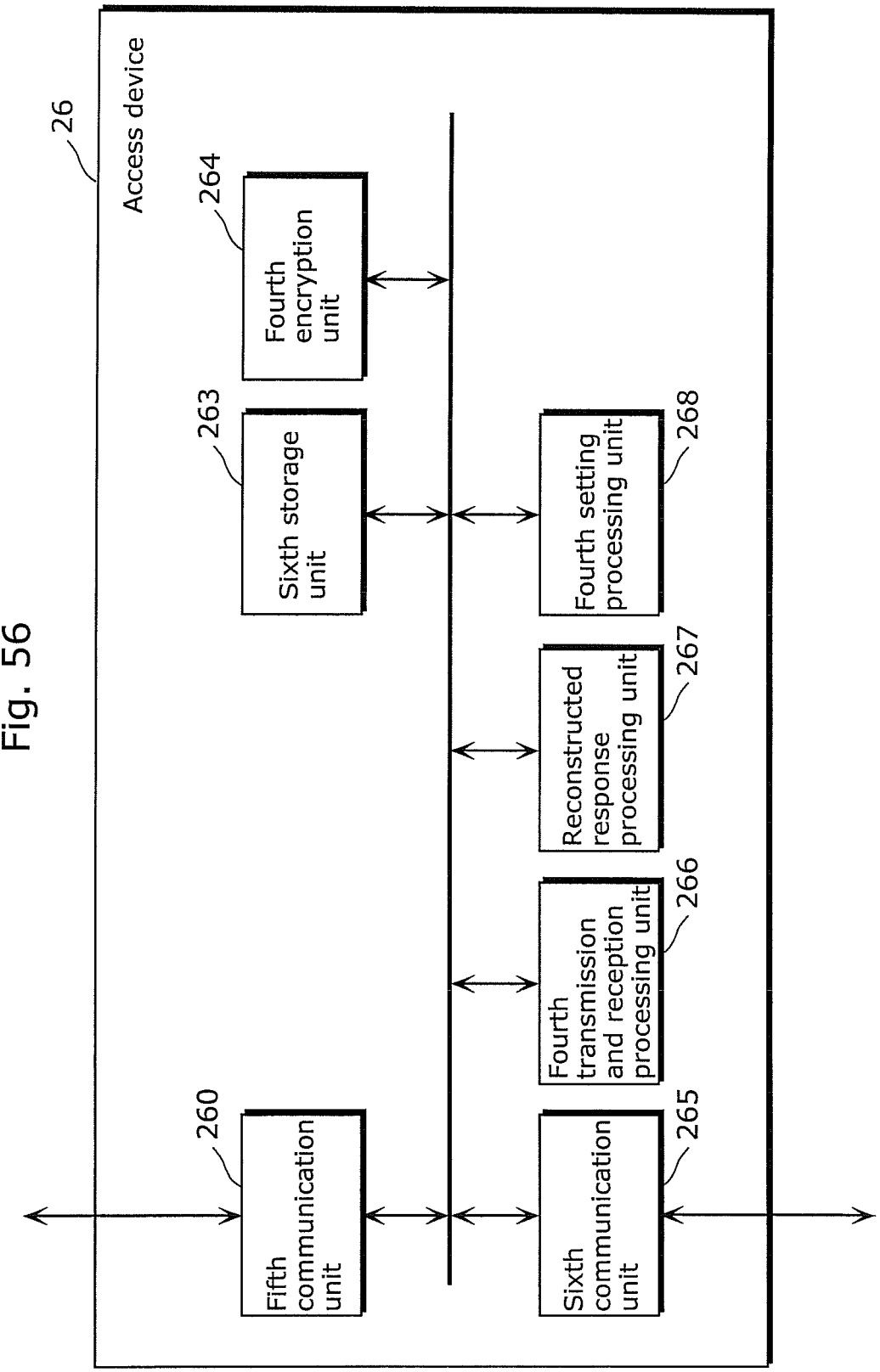
FIG. 56 is a block diagram showing a structure of an access device.

FIG. 56 is a block diagram showing a structure of the access device 26. As shown in FIG. 56, the access device 26 includes a fifth communication unit 260, a sixth storage unit 263, a fourth encryption unit 264, a sixth communication unit 265, a fourth transmission and reception processing unit 266, a reconstructed response processing unit 267, and a fourth setting processing unit 268. Among the structural elements, the essential structural elements are the fifth communication unit 260, the fourth encryption unit 264, and the sixth communication unit 265.

It is to be noted that the fifth communication unit 260 and the sixth communication unit 265 correspond to the fifth communication unit and the sixth communication unit in the CLAIMS of the present application. In addition, the fourth encryption unit 264 correspond to a third share decryption unit in the CLAIMS of the present application.

(1) Fifth Communication Unit 260

The fifth computer network 260 has a function for transmitting and receiving various kinds of data to and from the intermediate device 23 via the second computer network 24, in response to the request from the one of the functional blocks.

(2) Sixth Storage Unit 263

Figure 57:
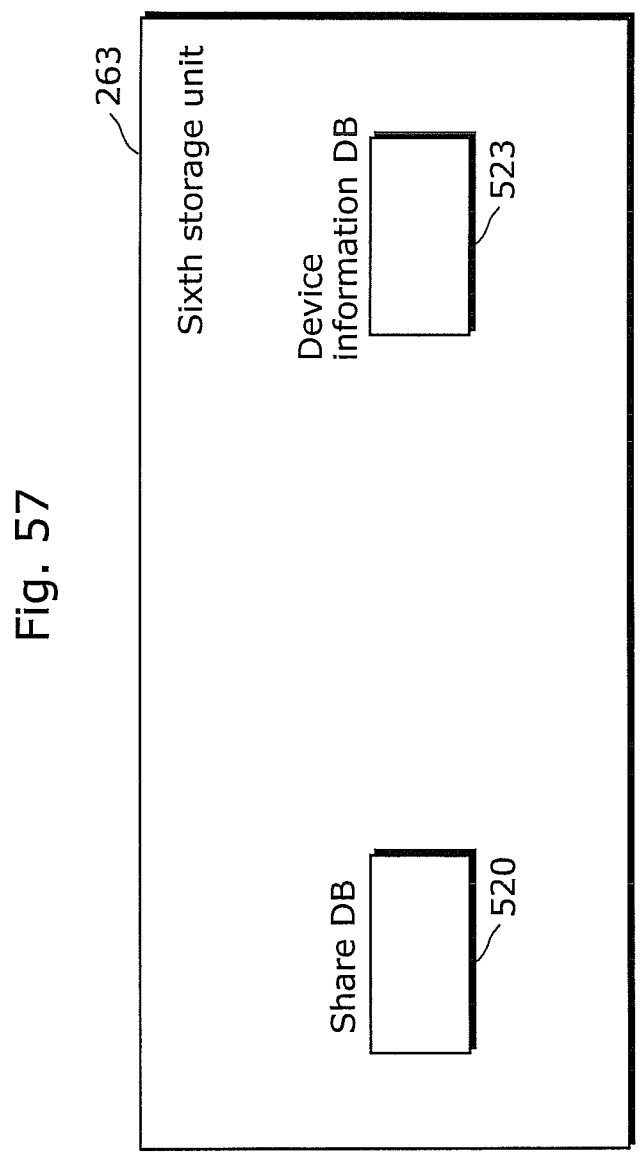
FIG. 57 is a diagram showing a structure of a sixth storage unit.

As shown in FIG. 57, the sixth storage unit 263 holds a share DB 520 and a device information DB 523.

Figure 58:
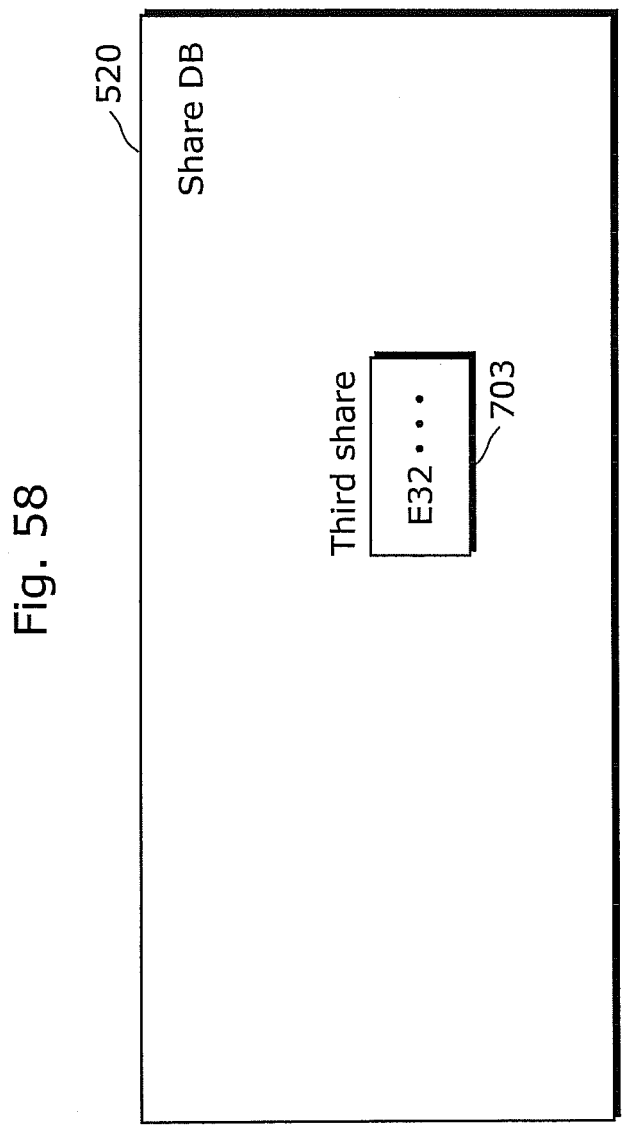
FIG. 58 is a diagram showing a structure of a share DB in the sixth storage unit.

As shown in FIG. 58, the share DB 520 includes a third share TSD (a third share 703 in FIG. 58).

Figure 59:
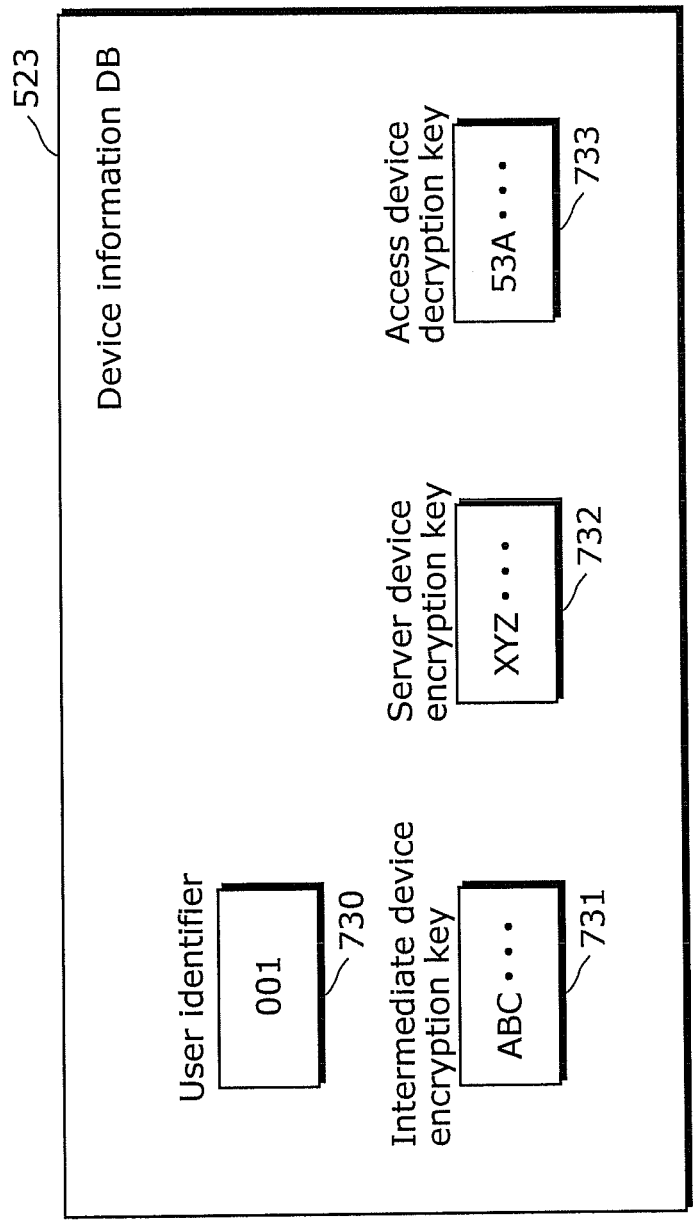
FIG. 59 is a diagram showing a structure of a device information DB in the sixth storage unit.

As shown in FIG. 59, the device information DB 523 includes a user identifier ID (a user identifier 730 in FIG. 59), an intermediate device encryption key CPK (an intermediate device encryption key 731 in FIG. 59), a server device encryption key SPK (a server device encryption key 732 in FIG. 59), and an access device decryption key ASK (an access device decryption key 733 in FIG. 59). The user identifier ID is a number identifying the access device 26. The intermediate device encryption key CPK is a key corresponding to the intermediate device decryption key CSK held by the intermediate device 23, and the server device encryption key SPK is a key corresponding to the server device decryption key SSK held by the server device 25. The access device encryption key APK is a decryption key held by the access device 26.

(3) Fourth Encryption Unit 264

When the fourth encryption unit 264 receives the user identifier ID and the encrypted third share ETSD, the fourth encryption unit 264 obtains the access device decryption key ASK from the device information DB 523 of the sixth storage unit 263. Next, the fourth encryption unit 264 obtains the encrypted third share ETSD using the access device decryption key ASK. The fourth encryption unit 264 stores the third share TSD that is a decoding result into the share DB 520 in the sixth storage unit 263 in association with the user identifier ID. Subsequently, the fourth encryption unit 264 obtains the server device encryption key SPK from the device information DB 523 in the sixth storage unit 263. Next, the fourth encryption unit 264 encrypts the third share TSD using the server device encryption key SPK. The result is referred to as the second encrypted third share E2TSD. Lastly, the fourth encryption unit 264 outputs the second encrypted third share E2TSD to the one of the functional blocks.

(4) Sixth Communication Unit 265

The sixth computer network 265 has a function for transmitting and receiving various kinds of data to and from the server device 25 via the third computer network 27, in response to the request from the one of the functional blocks.

(5) Fourth Transmission and Reception Processing Unit 266

Figure 60:
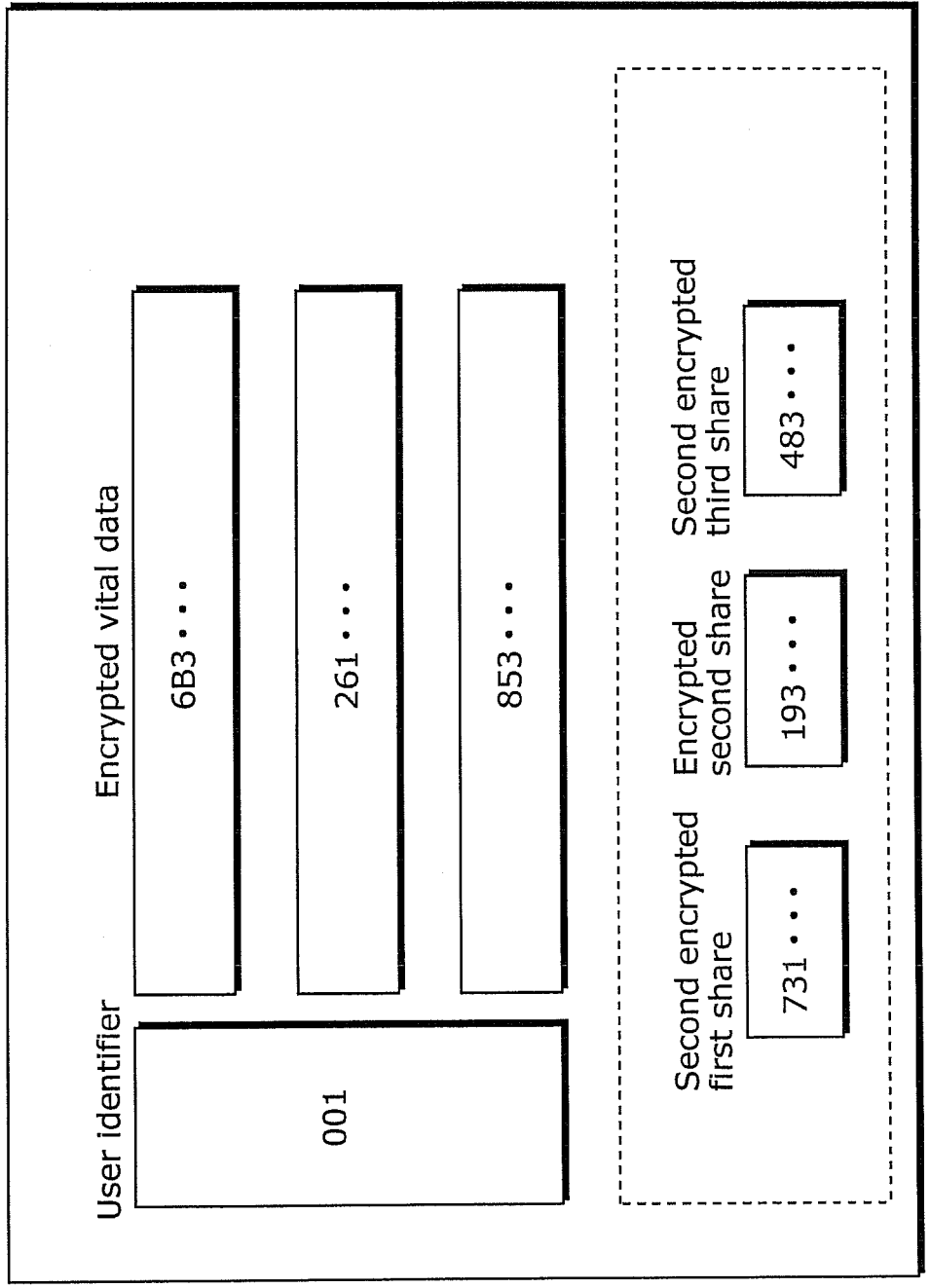
FIG. 60 is a diagram showing a structure of third data TD.

When the fourth transmission and reception processing unit 266 receives the second data SD from the intermediate device 23 and finds that the second data SD includes the encrypted first share EFSD, the second encrypted first share E2FSD, and the encrypted third share ETSD, the fourth transmission and reception processing unit 266 outputs the user identifier ID and the encrypted third share ETSD to the fourth encryption unit 264, and obtains the second encrypted third share E2TSD from the fourth encryption unit 264. Next, as shown in FIG. 60, the fourth transmission and reception processing unit 266 generates third data TD among the second data SD by replacing the encrypted third share ETSD with the second encrypted third share E2TSD. Next, the fourth transmission and reception processing unit 266 transmits the third data TD to the server device 25 via the sixth communication unit 265. When the fourth transmission and reception processing unit 266 receives the second data SD from the intermediate device 23 and finds that the second data SD does not include the encrypted first share EFSD, the second encrypted first share E2FSD, and the encrypted third share ETSD, the fourth transmission and reception processing unit 266 transmits the second data SD as the third data TD to the server device 25 via the sixth communication unit 265.

(6) Reconstructed Response Processing Unit 267

When the reconstructed response processing unit 267 receives the user identifier ID from the intermediate device 23 via the fifth communication unit 260, the reconstructed response processing unit 267 accesses the device information DB 523 in the sixth storage unit 263 first, and checks whether or not the received user identifier ID is the same as the user identifier ID stored in the device information DB 523. When the both are the same, the reconstructed response processing unit 267 obtains the third share TSD from the share DB 520 in the sixth storage unit 263, and transmits the third share TSD to the intermediate device 23 via the fifth communication unit 260.

(7) Fourth Setting Processing Unit 268

The fourth setting processing unit 268 has a function for setting the user identifier ID, the intermediate device encryption key CPK, the server device encryption key SPK, and the access device decryption key ASK, into the device information DB 523 in the first storage unit 213, based on the data that is input from the outside. For example, the fourth setting processing unit 268 may set the pieces of information based on the data that is input using a keyboard, or may be set based on data stored in a memory card such as a Secure Digital (SD) card. In addition, the fourth setting processing unit 268 includes a predetermined authentication function (such as password authentication), and performs authentication when the access device 26 establishes a connection with the server device 25. When the predetermined authentication is successfully completed, the server device 25 is capable of setting the third share TSD into the share DB 520 in the sixth storage unit 263 via the fourth setting processing unit 268.

[Structure of Server Device 25]

Lastly, a structure of the server device 25 is described.

Figure 61:
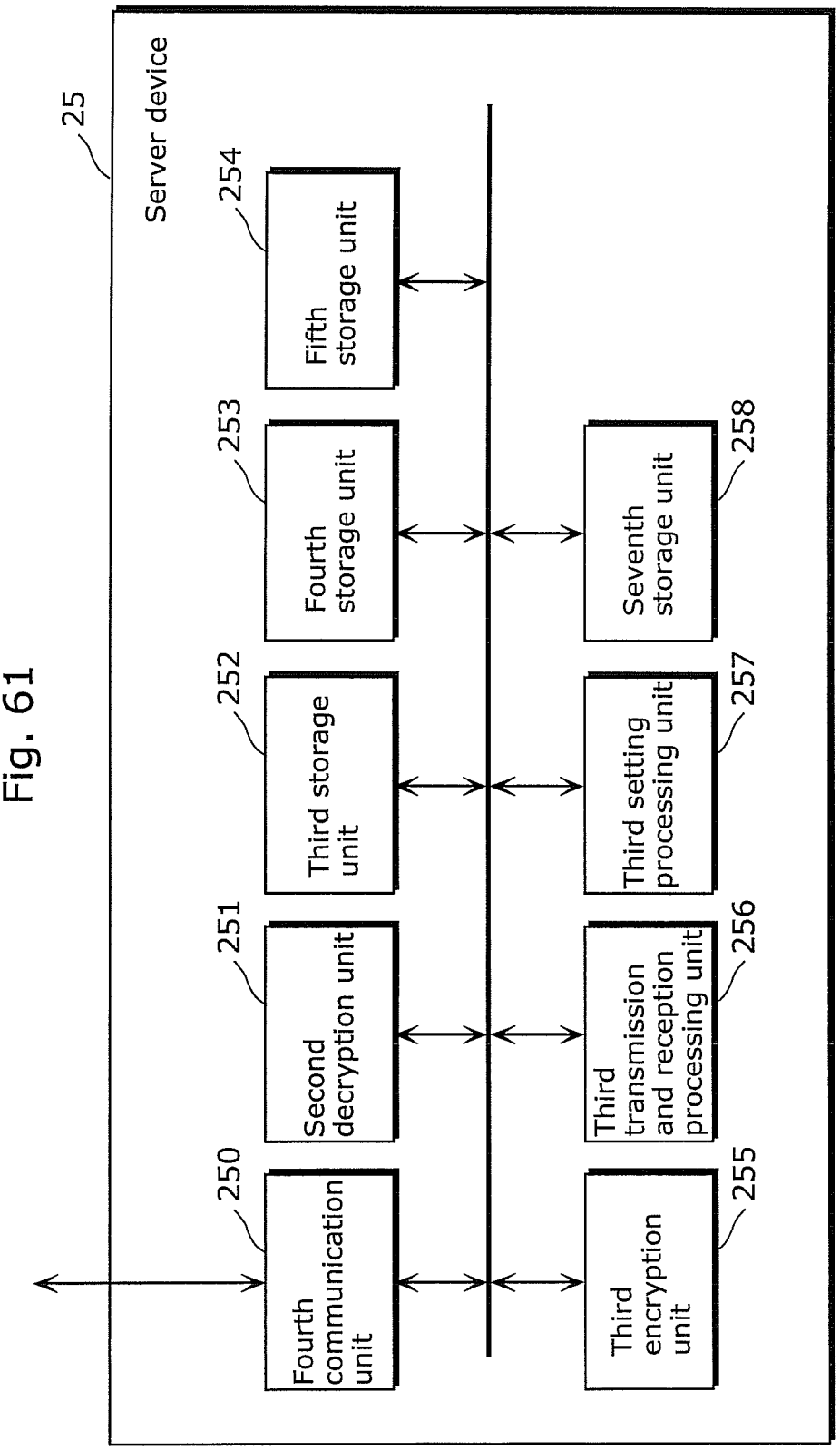
FIG. 61 is a block diagram showing a structure of a server device.

FIG. 61 is a block diagram showing the structure of the server device 25. As shown in FIG. 61, the server device 25 includes a fourth communication unit 250, a second decryption unit 251, a third storage unit 252, a fourth storage unit 253, a fifth storage unit 254, a third encryption unit 255, a third transmission and reception processing unit 256, a third setting processing unit 257, and a seventh storage unit 258. Among the structural elements, the essential structural elements are the fourth communication unit 250, the second decryption unit 251, and the third encryption unit 255.

It is to be noted that the fourth communication unit 250 corresponds to a fourth communication unit in the CLAIMS of the present application. In addition, the second decryption unit 251 corresponds to a reconstruction unit and a vital data decryption unit in the CLAIMS of the present application. In addition, the third storage unit 252 corresponds to a holding unit in the CLAIMS of the present application. In addition, the third encryption unit 255 corresponds to a share decryption unit in the CLAIMS of the present application. In addition, the third setting processing unit 257 corresponds to a supply unit in the CLAIMS of the present application.

(1) Fourth Communication Unit 250

The fourth communication unit 250 has a function for transmitting and receiving various kinds of data to and from the access device 26 via the third computer network 27.

(2) Second Decryption Unit 251

The second decryption unit 251 has the following two functions.

A. Reconstruction of Decryption Key from Shares

The second decryption unit 251 has a function for a case of receiving the first share FSD, the second share SSD, and the third share TSD from the one of the functional blocks; the function is for decrypting a decryption key SK from two of the shares according to the secret sharing scheme and outputting the decryption key SK to the one of the functional blocks.

B. Decryption of Encrypted Vital Data

The second decryption unit 251 has a function for a case of receiving encrypted vital data EVD and the decryption key SK from the one of the functional blocks; the function is for decrypting the encrypted vital data EVD using the decryption key SK and outputting the vital data VD as the decryption result to the one of the functional blocks.

(3) Third Storage Unit 252

Figure 62:
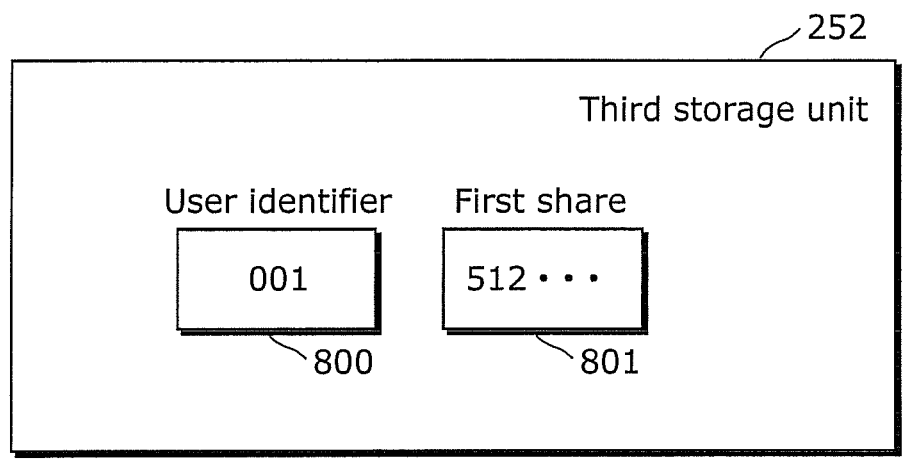
FIG. 62 is a diagram showing a structure of a third storage unit of the server device.

As shown in FIG. 62, the third storage unit 252 holds a user identifier ID (a user identifier 800 in FIG. 62) and a first share FSD (a first share 801 in FIG. 62).

(4) Fourth Storage Unit 253

Figure 63:
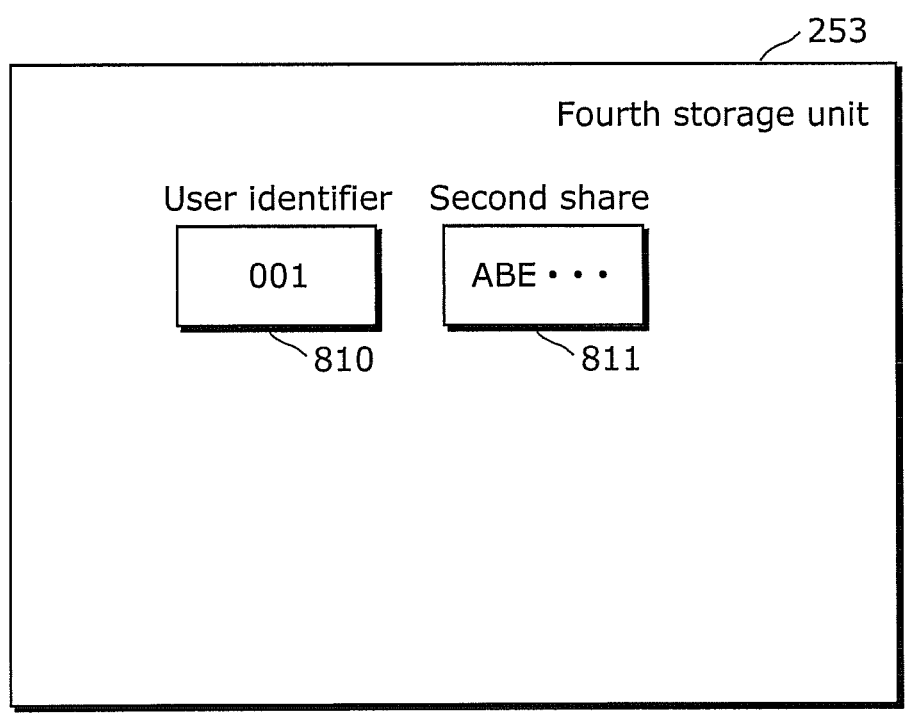
FIG. 63 is a diagram showing a structure of a fourth storage unit of the server device.

As shown in FIG. 63, the fourth storage unit 253 holds a user identifier ID (a user identifier 810 in FIG. 62) and a second share SSD (a second share 811 in FIG. 62).

(5) Fifth Storage Unit 254

Figure 64:
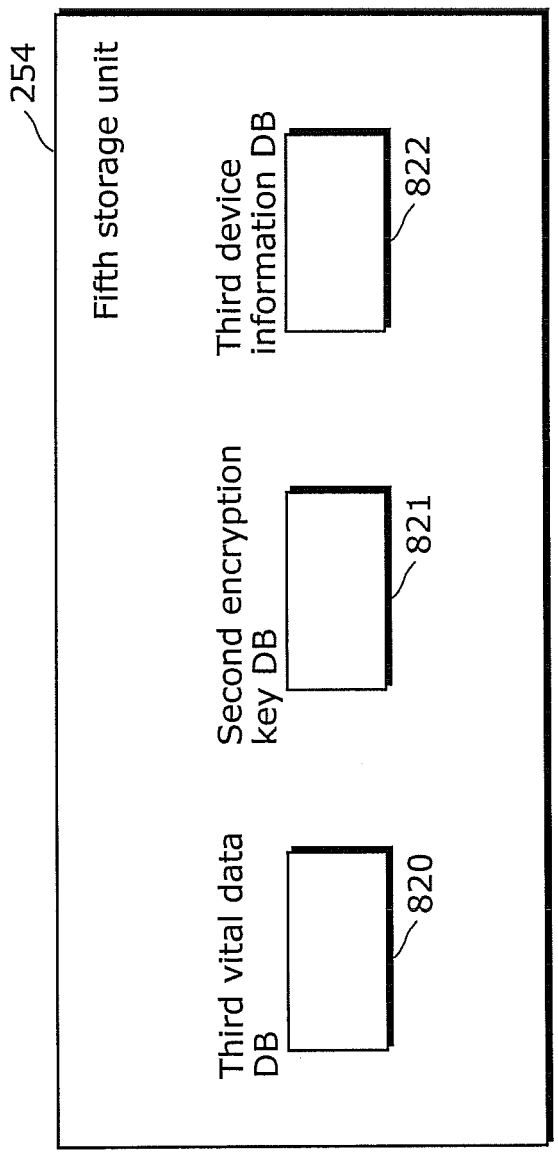
FIG. 64 is a diagram showing a structure of a fifth storage unit of the server device.

As shown in FIG. 64, the fifth storage unit 254 holds a third vital data DB 820, a second encryption key DB 821, and a third device information DB 822.

Figure 65:
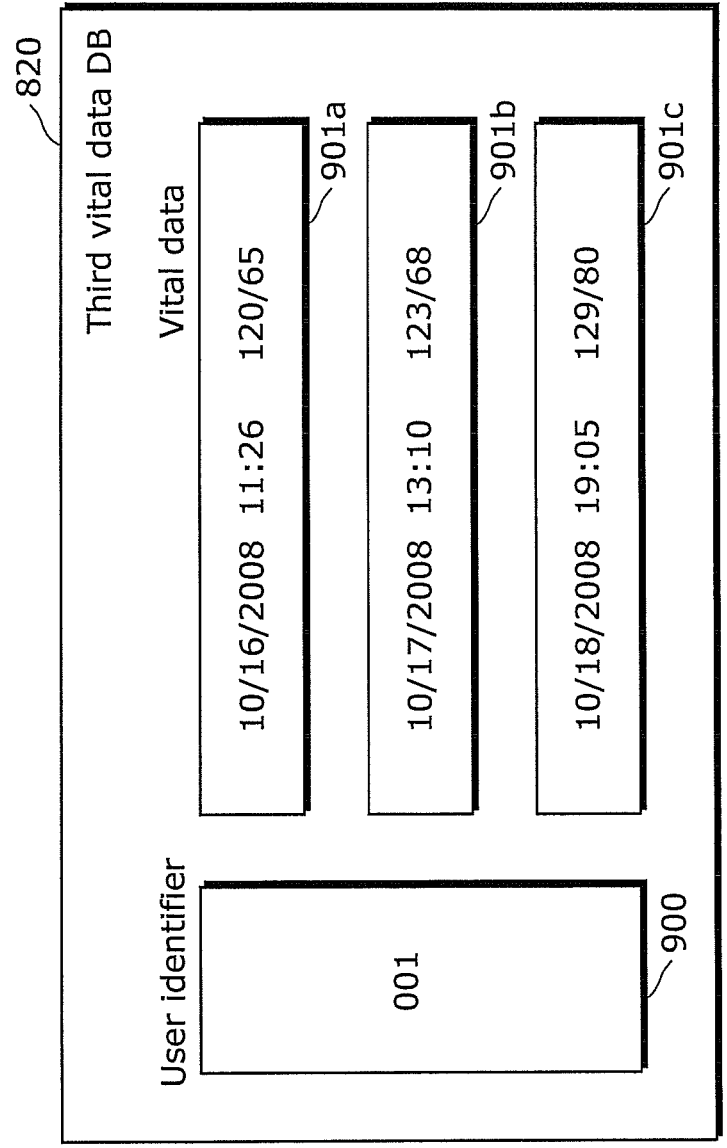
FIG. 65 is a diagram showing a structure of a third vital data DB in the fifth storage unit of the server device.

As shown in FIG. 65, the third vital data DB 820 includes a user identifier ID (a user identifier 900 in FIG. 65) and vital data VD (vital data 901$a$, 901$b$, and 901$c$ in FIG. 65).

Figure 66:
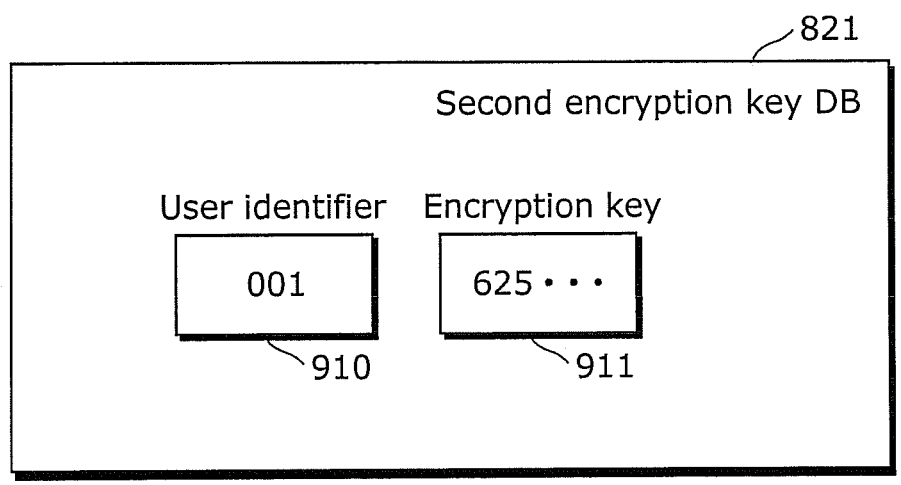
FIG. 66 is a diagram showing a structure of a second encryption key DB in the fifth storage unit of the server device.

As shown in FIG. 66, the second encryption key DB 821 includes a user identifier ID (a user identifier 910 in FIG. 66) and a decryption key SK (a decryption key 911 in FIG. 66).

Figure 67:
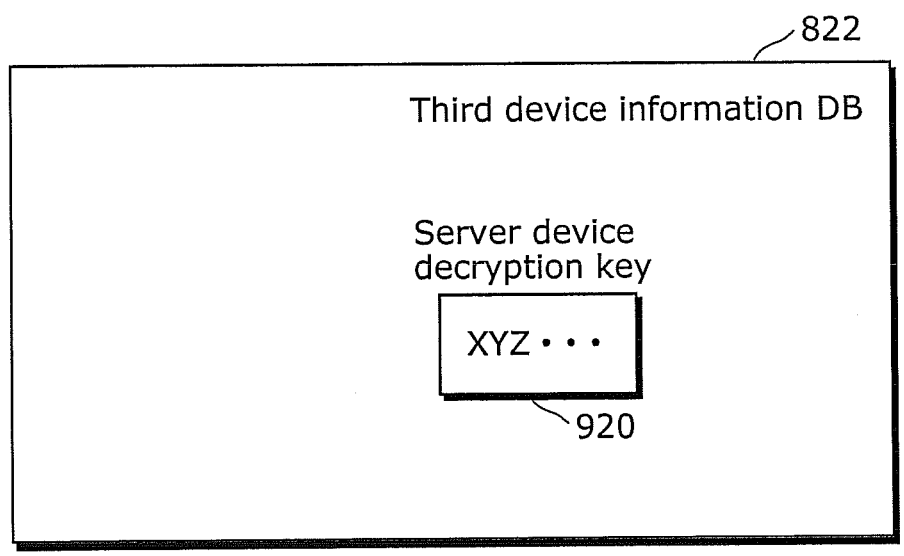
FIG. 67 is a diagram showing a structure of a third device information DB in the fifth storage unit of the server device.

As shown in FIG. 67, the third device information DB 822 includes a server device decryption key SSK (a server device decryption key 920 in FIG. 67).

(6) Third Encryption Unit 255

When the third encryption unit 255 receives, from the one of the functional blocks, the server device decryption key SSK, the second encrypted first share E2FSD, the encrypted second share ESSD, and the second encrypted third share E2TSD, the third encryption unit 255 decrypts all of the second encrypted first share E2FSD, the encrypted second share ESSD, and the second encrypted third share E2TSD, using the sever device decryption key SSK to obtain the first share FSD, the second share SSD, and the third share TSD. Next, the third encryption unit 255 outputs the first share FSD, the second share SSD, and the third share TSD to the one of the functional blocks.

(7) Third Transmission and Reception Processing Unit 256

When the third transmission and reception processing unit 256 receives the third data TD from the access device 26 via the fourth communication unit 250, the third transmission and reception processing unit 256 firstly checks whether or not the third data TD includes the second encrypted first share E2FSD. When the second encrypted first share E2FSD is included therein, the third transmission and reception processing unit 256 obtains the server device decryption key SSK from the third device information DB 822 in the fifth storage unit 254. Next, the third transmission and reception processing unit 256 extracts, from the third data TD, the second encrypted first share E2FSD, the encrypted second share ESSD, and the second encrypted third share E2TSD, outputs, to the third encryption unit 255, the sever device decryption key SSK, the second encrypted first share E2FSD, the encrypted second share ESSD, and the second encrypted third share E2TSD, and obtains, from the third encryption unit 255, the first share FSD, the second share SSD, and the third share TSD. Next, the third transmission and reception processing unit 256 outputs the first share FSD, the second share SSD, and the third share TSD to the second decryption unit 251, and obtains the decryption key SK from the second decryption unit 251. The third transmission and reception processing unit 256 stores the decryption key SK into the second encryption key DB 821 in the fifth storage unit 254. The above-described operations are operations that are additionally performed when the second encrypted first share E2FSD is included in the third data TD. Next, the third transmission and reception processing unit 256 outputs, to the second decryption unit 251, the decryption key SK obtained from the second encryption key DB 821 in the fifth storage unit 254, and obtains the vital data VD from the second decryption unit 251. The third transmission and reception processing unit 256 stores the obtained vital data VD into the third vital data DB 820 in the fifth storage unit 254.

(8) Third Setting Processing Unit 257

The third setting processing unit 257 has a function for setting a server device decryption key SSK into the third device information DB 822 in the fifth storage unit 254, based on the data that is input from the outside. For example, the third setting processing unit 257 is capable of setting the server device decryption key SSK based on the data that is input using a keyboard.

Furthermore, the third setting processing unit 257 has a function for setting the second share SSD into the measurement device 21, when the measurement device 21 is directly connected to the server device 25. Furthermore, the third setting processing unit 257 has a function for setting the first share FSD into the intermediate device 23 when the intermediate device 23 is directly connected to the server device 25. Furthermore, the third setting processing unit 257 has a function for setting the third share TSD into the access device 26 when the access device 26 is directly connected to the server device 25.

(9) Seventh Storage Unit 258

Figure 68:
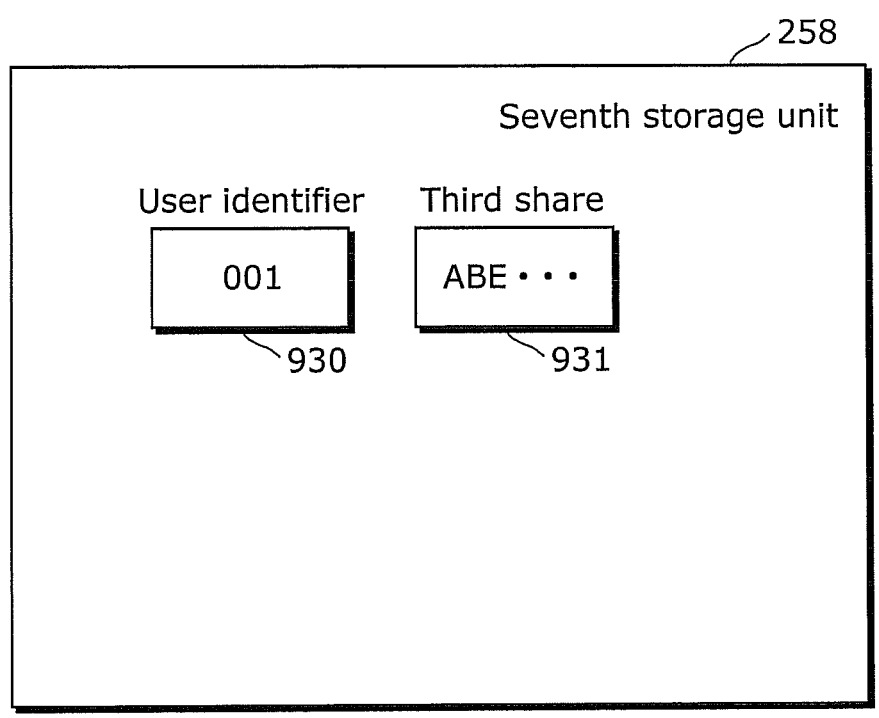
FIG. 68 is a diagram showing a structure of a seventh storage unit of the server device.

As shown in FIG. 68, the seventh storage unit 258 holds a user identifier ID (a user identifier 930 in FIG. 68) and a third share TSD (a third share 931 in FIG. 68).

The respective structural elements have been described above. Hereinafter, exemplary operations performed by the respective structural devices are described. First, the outline of the exemplary operations and the achievable functions are described.

Figure 69:
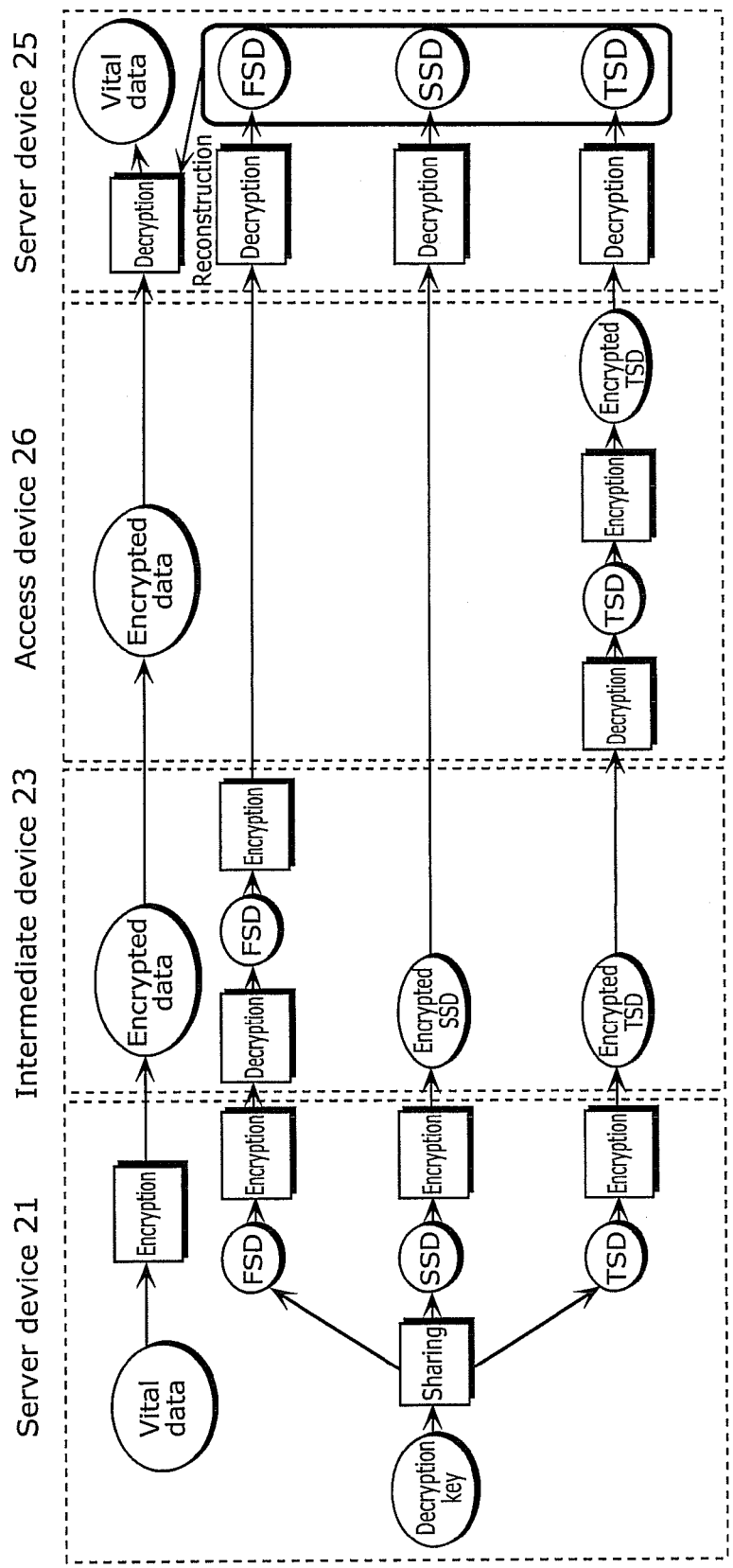
FIG. 69 is a diagram showing a concept of operations in the health care system.

With reference to FIG. 69, when the measurement device 21 is firstly used by the patient, the measurement device 21 firstly generates an encryption key PK, a decryption key SK, and three shares (a first share FSD, a second share SSD, and a third share TSD) corresponding to the decryption key SK. Here, it is assumed that the original decryption key SK can be obtained when two of the three shares are available. Next, the measurement device 21 measures vital data VD when the patient presses the "measure button", and accumulates the vital data VD encrypted using the encryption key PK. When a nursing staff member visits the patient's home with certain timing and the nursing staff member presses the "transmission button" of the measurement device 21, the measurement device 21 encrypts the first share FSD in such a manner that only the intermediate device 23 can decrypt the first share FSD encrypted, the second share SSD encrypts in such a manner that only the server device 25 can decrypt the second share SSD encrypted, and encrypts the third share TSD in such a manner that only the access device 26 can decrypt the third share TSD encrypted. The measurement device 21 transmits the first share FSD encrypted, the second share SSD encrypted, and the third share TSD encrypted to the intermediate device 23 brought by the nursing staff member, together with the vital data VD encrypted. Upon receiving the share and data, the intermediate device 23 first accumulates the vital data VD encrypted. Next, the intermediate device 23 decrypts the first share FSD encrypted, and accumulates the first share FSD decrypted. Next, the intermediate device 23 encrypts the first share FSD in such a manner that only the sever device 25 can decrypt the first share FSD, and temporarily accumulates the first share FSD. After the nursing staff member returns to the nursing station or his or her home, the intermediate device 23 transmits, to the access device 26, the first share FSD encrypted, the second share SSD, the third share TSD encrypted, and the vital data VD. The access device 26 decrypts the third share TSD encrypted, and accumulates the third share TSD. Next, the access device 26 encrypts the third share TSD in such a manner that only the server device 25 decrypts the third share TSD, and transmits, to the server device 25, the first share FSD encrypted, the second share SSD encrypted, the third share TSD encrypted, and the vital data VD encrypted. The server device 25 decrypts the first share FSD encrypted, the second share SSD encrypted, and the third share TSD encrypted, to obtain the first share FSD, the second share SSD, and the third share TSD, respectively, and obtains the decryption key SK from two of the shares. Next, the server device 25 decrypts the vital data VD encrypted using the decryption key SK to obtain the vital data VD. In this way, the server device 25 can obtain the vital data VD.

Figure 70:
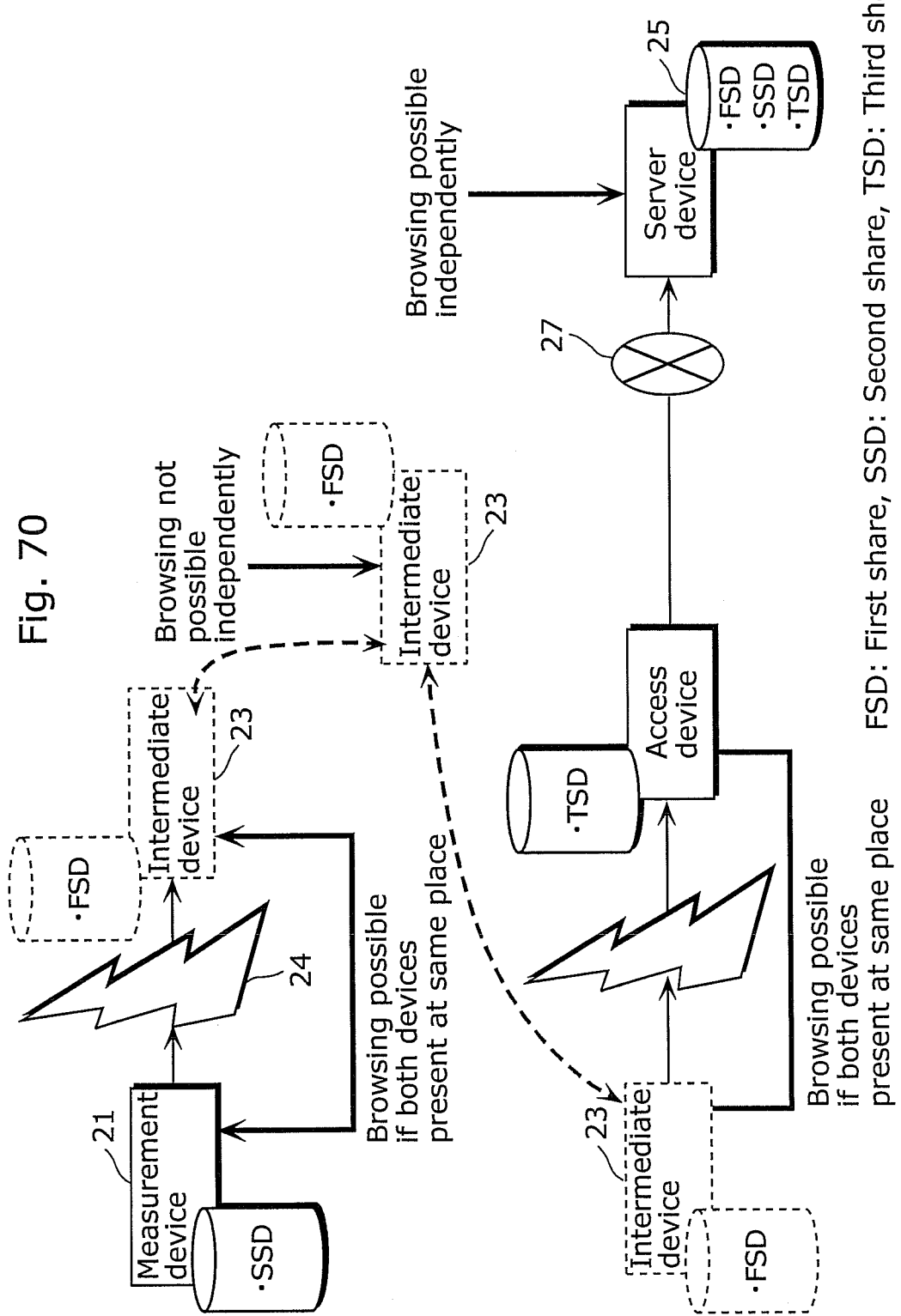
FIG. 70 is a diagram showing a concept of exemplary operations in the health care system.

Another example is given with reference to FIG. 70. It is assumed that, in this case, the nursing staff member visits the patient's home with timing after the aforementioned timing, and the nursing staff member wishes to browse the vital data VD measured before. At this time, when the nursing staff member presses the "browse button" of the intermediate device 23 held by the nursing staff member himself or herself and inputs the user identifier ID of the patient, the intermediate device 23 accesses the measurement device 21 and obtains the second share SSD. Next, the intermediate device 23 reconstructs the decryption key SK by combining the second share SSD obtained from the measurement device 21 and the first share FSD held by the intermediate device 23. The intermediate device 23 decrypts the held vital data VD encrypted, using the reconstructed decryption key SK to obtain the vital data VD. In this way, the intermediate device 23 also allows browsing of the vital data VD when it co-operates with the measurement device 21.

Alternatively, it is assumed that the nursing staff member is in the nursing station or his or her home with other timing after the aforementioned timing, and the nursing staff member wishes to browse the vital data VD measured before. At this time, when the nursing staff member presses the "browse button" of the intermediate device 23 held by the nursing staff member himself or herself and inputs the user identifier ID of the patient, the intermediate device 23 accesses the access device 26 and obtain the third share TSD. Next, the intermediate device 23 reconstructs the decryption key SK by combining the third share TSD and the first share FSD held by the intermediate device 23. The intermediate device 23 decrypts the held vital data VD encrypted, using the reconstructed decryption key SK to obtain the vital data VD. In this way, the intermediate device 23 also allows browsing of the vital data VD when it co-operates with the access device 26.

Another case is considered in which the measurement device 21 in use by the patient has a trouble with certain timing. In this case, a system manager firstly sets a user identifier ID etc. into a measurement device 21x having the same structure as that of the measurement device 21. Next, the server device 25 accesses the measurement device 21x, and outputs the second share SSD held by the server device 25 to the measurement device 21x. In this way, the server device 25 keeps holding the second share SSD after the decryption key SK is reconstructed, and thus is capable of setting the same second share SSD into the measurement device 21x even when the measurement device 21 has a trouble. It is to be noted that the server device 25 may generate, from the decryption key SK, a share that is different from the first share FSD, the second share SSD, and the third share TSD, and output the generated share to the measurement device 21x. At this time, uniquely associating the measurement device 21x with the share makes it possible to identify, if the share leaks to the outside, the measurement device 21x that is the source of the share.

In addition, another case is considered in which the intermediate device 23 in use by the nursing staff member has a trouble with certain timing. In this case, a system manager firstly sets a user identifier ID etc. into an intermediate device 23y having the same structure as that of the intermediate device 23. Next, the server device 25 accesses the intermediate device 23y, and outputs the first share FSD held by the server device 25. In this way, the server device 25 keeps holding the first share FSD even after the decryption key SK is reconstructed, and thus is capable of setting the same first share FSD into the intermediate device 23y even when the intermediate device 23 has a trouble. It is to be noted that the server device 25 may generate, from the decryption key SK, share that is different from the first share FSD, the second share SSD, and the third share TSD, and output the generated share to the intermediate device 23y. At this time, uniquely associating the intermediate device 23y with each of the shares makes it possible to identify, if the share leaks to the outside, the intermediate device 23y that is the source of the share.

Lastly, another case is considered in which the access device 26 that is located at the nursing station or the home of the nursing staff member has a trouble with certain timing. In this case, a system manager firstly sets a user identifier ID etc. into an access device 26z having the same structure as that of the access device 26. Next, the server device 25 accesses the access device 26z, and outputs the third share TSD held by the server device 25. In this way, the server device 25 keeps holding the third share TSD even after the decryption key SK is reconstructed, and thus is capable of setting the same third share TSD into the access device 26z even when the access device 26 has a trouble. It is to be noted that the server device 25 may generate, from the decryption key SK, a share that is different from the first share FSD, the second share SSD, and the third share TSD, and output the generated share to the access device 26z. At this time, uniquely associating the access device 26z with the share makes it possible to identify, if the share leaks to the outside, the access device 26z that is the source of the share.

The outline of the operations has been described above. Hereinafter, the operations are described in detail. For convenience, the descriptions are given separately for: (i) operations that the measurement device 21 performs when measuring and transmitting the vital data; (ii) operations that the intermediate device 23 performs when displaying the vital data using the measurement device 21; (iii) operations for setting a share into the intermediate device 23y when the intermediate device 23 has a trouble; (iv) operations for setting a share into the measurement device 21x when the measurement device 21 has a trouble; (v) operations that the intermediate device 23 performs when displaying the vital data using the access device 26; and (vi) operations for setting a share into the access device 26z when the access device 26 has a trouble.

[(i) Operations Performed by Measurement Device 21 to Measure and Transmit Vital Data]

Figure 71:
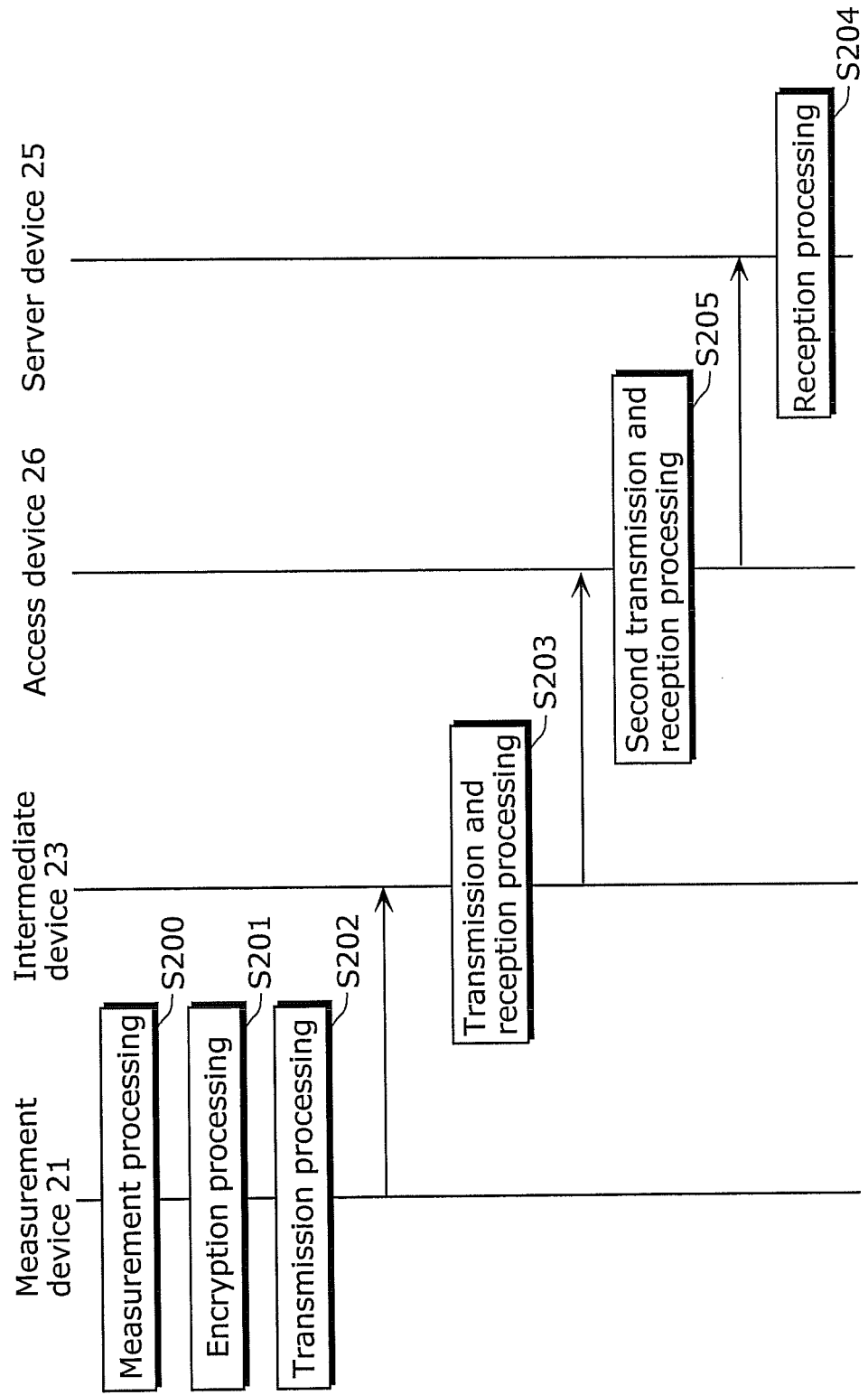
FIG. 71 is a flowchart of exemplary operations at the time of measurement in the health care system.

Hereinafter, with reference to a flowchart in FIG. 71, a description is given of the operations performed by the measurement device 21 when measuring and transmitting the vital data.

The measurement device 21 performs a "measurement process (Step S200)".

The measurement device 21 performs an "encryption process (Step S201)".

The measurement device 21 performs a "transmission process (Step S202)".

The intermediate device 23 performs a "transmission and reception process (Step S203)".

The access device 26 performs a "second transmission and reception process (Step S205)".

The server device 25 performs the "reception process (Step S204)" to complete the sequential processes.

Next, detailed descriptions are given for the respective operations performed by the measurement device 21.

Figure 72:
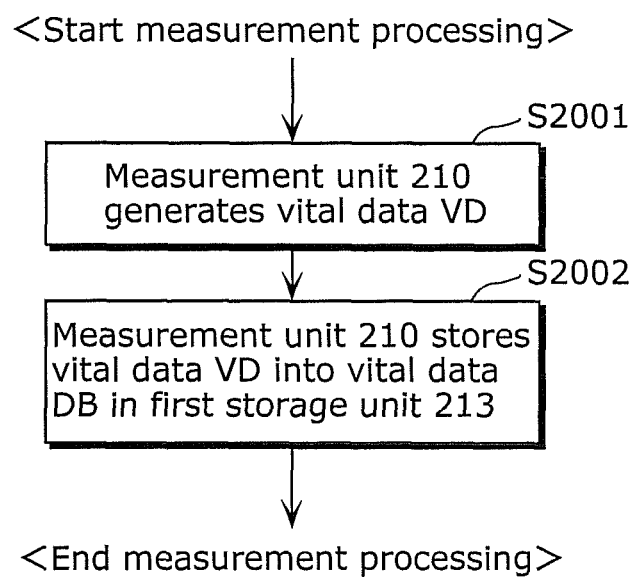
FIG. 72 is a flowchart showing details of "measurement processing" performed by the measurement device.

[Details of Measurement Process (Step S200): see FIG. 72]

The measurement unit 210 generates vital data VD (Step S2001).

The measurement unit 210 stores the vital data VD into the vital data DB 501 in the first storage unit 213 (Step S2002).

Figure 73:
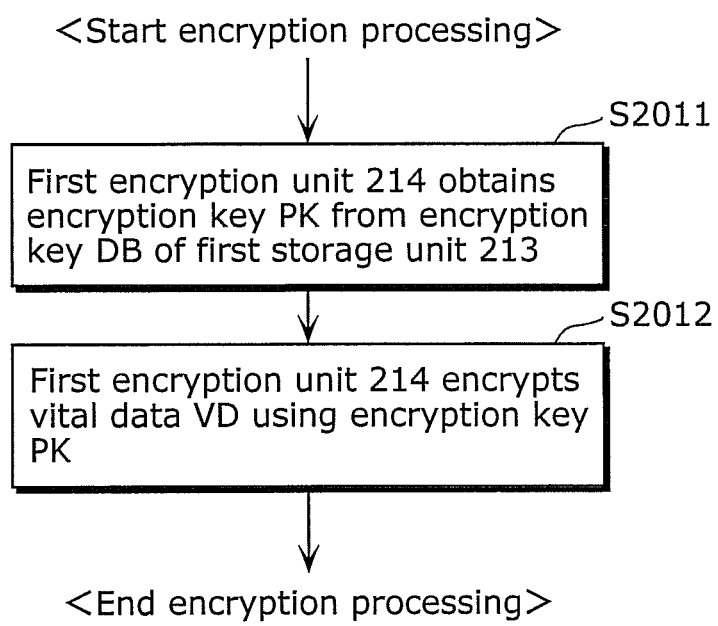
FIG. 73 is a flowchart showing details of "encryption processing" performed by the measurement device.

[Details of encryption process (Step S201): see FIG. 73]

The first encryption unit 214 obtains the encryption key PK from the encryption key DB 502 in the first storage unit 213 (Step S2011).

The first encryption unit 214 encrypts the vital data VD using the encryption key PK (Step S2012).

Figure 74:
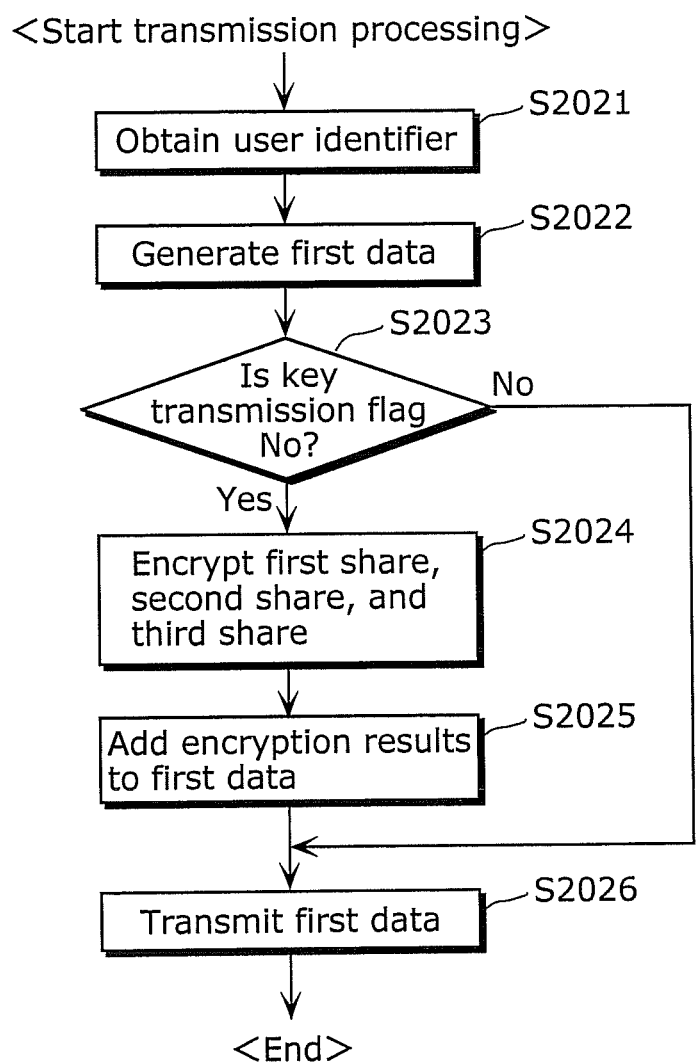
FIG. 74 is a flowchart showing details of "transmission processing" performed by the measurement device.

[Details of Transmission Process (Step S202): see FIG. 74]

The first transmission and reception processing unit 216 obtains the user identifier ID from the device information DB 503 in the first storage unit 213 (Step S2021).

The first transmission and reception processing unit 216 generates the first data FD (Step S2022).

When the key transmission flag SF indicates "No" (Yes in Step S2023), the first encryption unit 214 encrypts the first share FSD, the second share SSD, and the third share TSD (Step S2024).

The first transmission and reception processing unit 216 adds, to the first data FD, the encrypted first share EFSD, the encrypted second share ESSD, and the encrypted third share ETSD (Step S2025).

When the key transmission flag SF indicates "Yes" ("No" in Step S2023) or after the processing in Step S205, the first transmission and reception processing unit 216 transmits the first data FD to the intermediate device 23 (Step S2026).

Next, detailed descriptions are given for the respective operations performed by the intermediate device 23.

Figure 75:
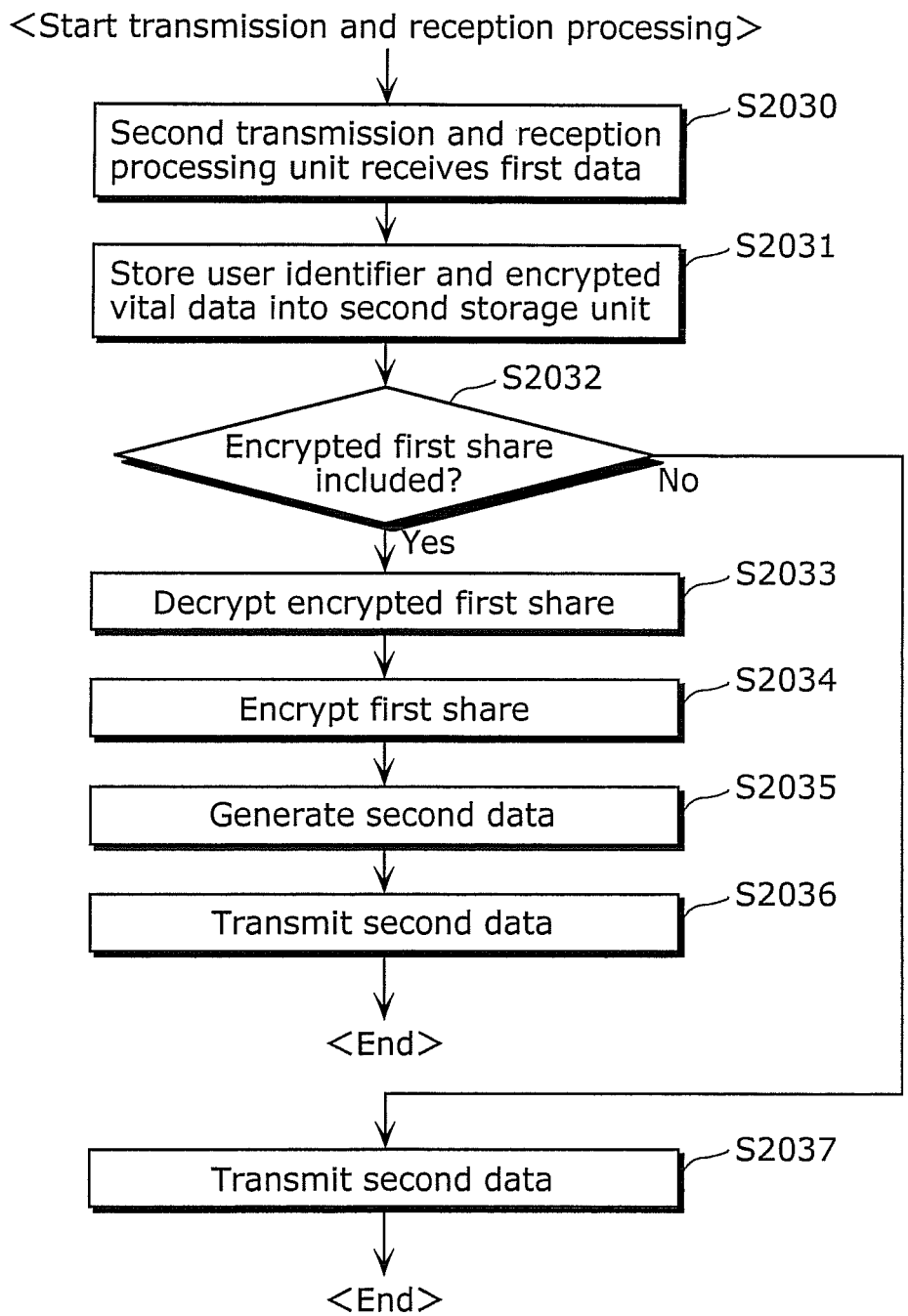
FIG. 75 is a flowchart showing details of "transmission and reception processing" performed by the intermediate device.

[Details of Transmission and Reception Process (Step S203): see FIG. 75]

The second transmission and reception processing unit 237 receives the first data FD from the measurement device 21 (Step S2030).

The second transmission and reception processing unit 237 stores the user identifier ID and the encrypted vital data EVD into the second vital data DB 511 in the second storage unit 231 (Step S2031).

When the encrypted first share EFSD is included in the first data FD (Yes in Step S2032), the second encryption unit 235 decrypts the encrypted first share EFSD (Step S2033).

The second encryption unit 235 encrypts the first share FSD (Step S2034).

The second transmission and reception processing unit 237 replaces the encrypted first share EFSD included in the first data FD with the second encrypted first share E2FSD to generate the second data SD (Step S2035).

The second transmission and reception processing unit 237 transmits (Step S2036) the second data SD to the access device 26 to complete the sequential processes.

When the encrypted first share EFSD is not included in the first data FD (No in Step S2032), the second transmission and reception processing unit 237 transmits (Step S2037) the first data FD as the second data SD to the access device 26 to complete the sequential processes.

Next, detailed descriptions are given for the respective operations performed by the access device 26.

Figure 76:
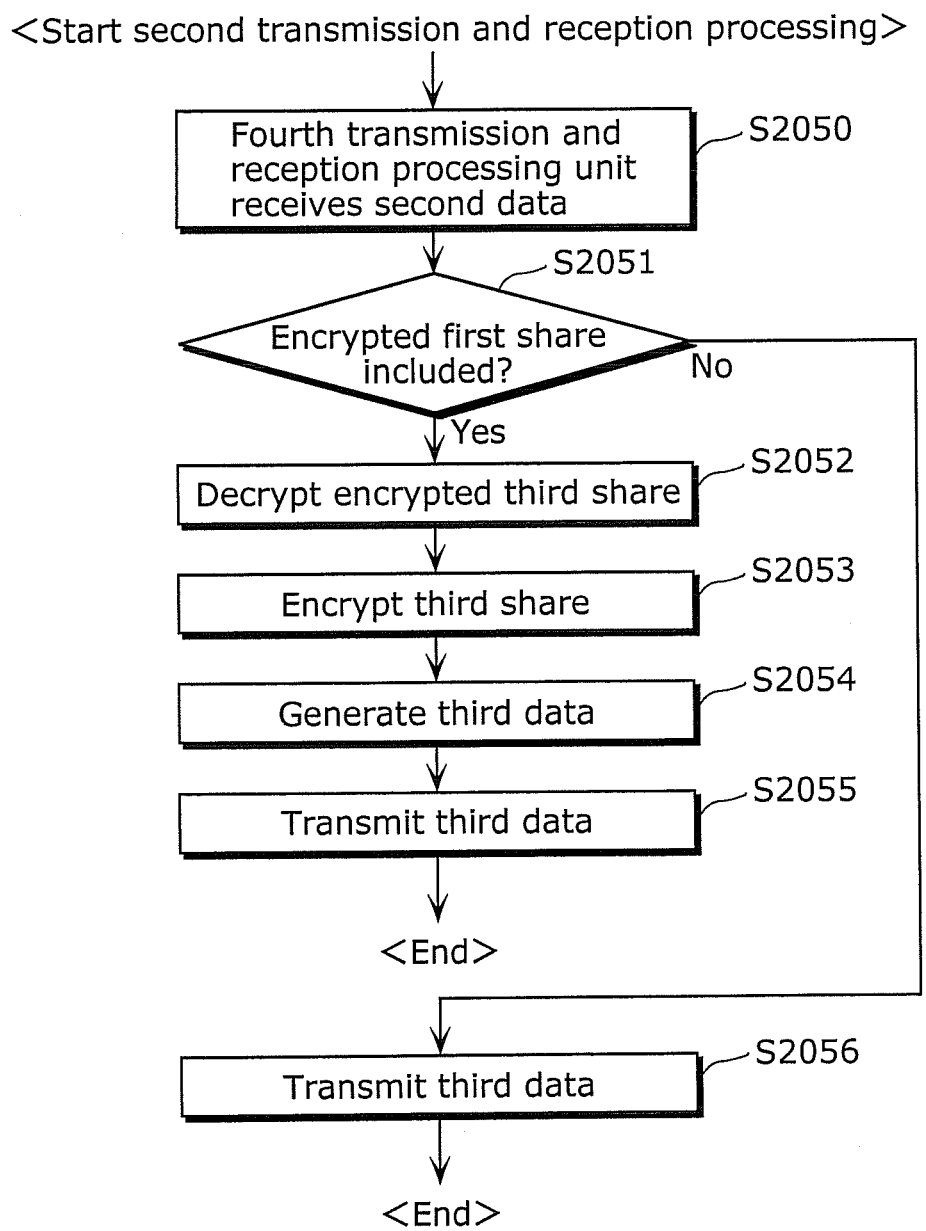
FIG. 76 is a flowchart showing details of "second transmission and reception processing" performed by the access device.

[Details of Second Transmission and Reception Process (Step S205): see FIG. 76]

The fourth transmission and reception processing unit 266 receives the second data SD from the intermediate device 23 (Step S2050).

When the second data SD includes the encrypted first share EFSD (Yes in Step S2051), the fourth encryption unit 264 decrypts the encrypted third share ETSD (Step S2052).

The fourth encryption unit 264 encrypts the third share TSD (Step S2053).

The fourth transmission and reception processing unit 266 generates the third data TD by replacing the encrypted third share ETSD included in the second data SD with the second encrypted third share E2TSD (Step S2054).

The fourth transmission and reception processing unit 266 transmits (Step S2055) the third data TD to the server device 25 to complete the sequential processes.

When the encrypted first share EFSD is not included in the second data FD (No in Step S2051), the fourth transmission and reception processing unit 266 transmits (Step S2056) the second data SD as the third data TD to the server device 25 to complete the sequential processes.

Lastly, detailed descriptions are given for the respective operations performed by the server device 25.

Figure 77:
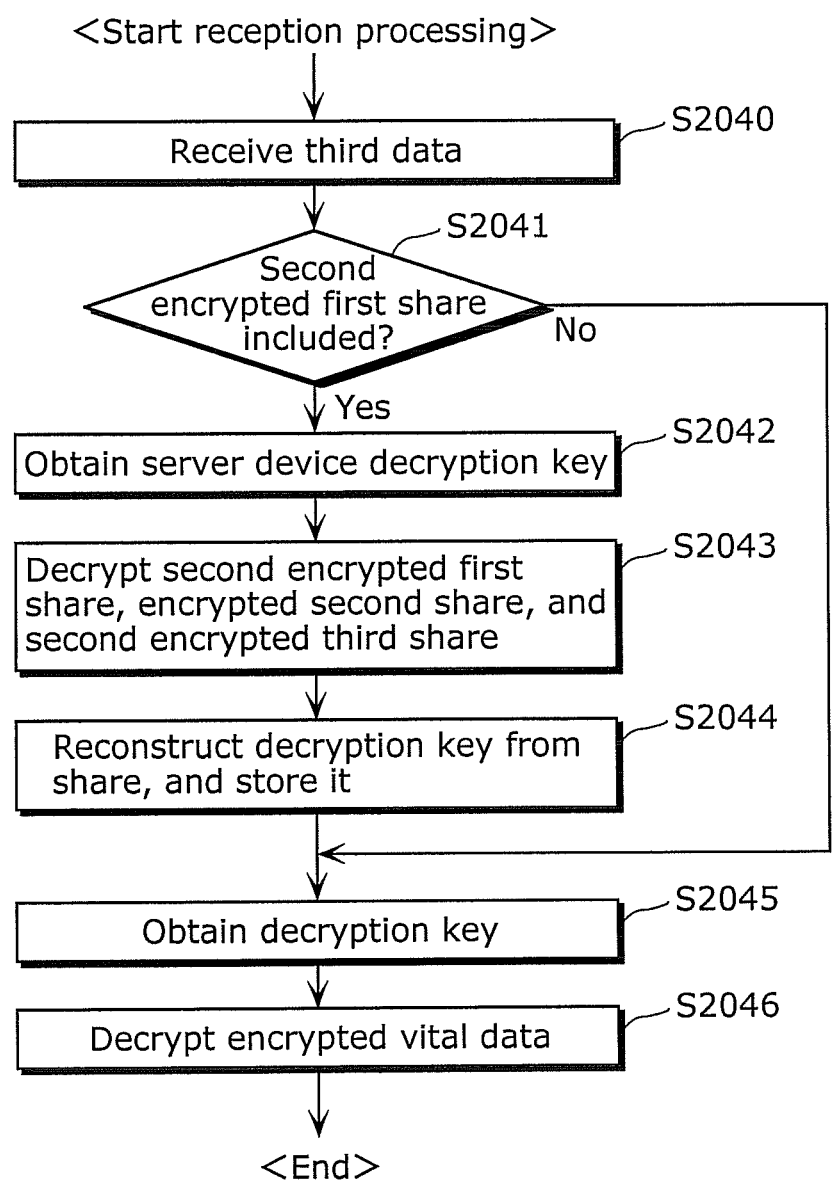
FIG. 77 is a flowchart showing details of "reception processing" performed by the server device.

[Details of Reception Process (Step S204): see FIG. 77]

The third transmission and reception processing unit 256 receives the third data TD from the access device 26 (Step S2040).

The third transmission and reception processing unit 256 checks whether or not the second encrypted first share E2FSD is included in the third data TD (Step S2041).

When the second encrypted first share E2FSD is included in the third data TD (Yes in Step S2041), the third transmission and reception processing unit 256 obtains the server device decryption key SSK from the third device information DB 822 in the fifth storage unit 254 (Step S2042).

The third encryption unit 255 decrypts the second encrypted first share E2FSD, the encrypted second share ESSD, and the second encrypted third share E2TSD, using the server device decryption key SSK (Step S2043).

The second decryption unit 251 obtains the decryption key SK using the first share FSD, the second share SSD, and the third share TSD. The second decryption unit 251 stores the obtained decryption key SK into the second encryption key DB 821 in the fifth storage unit 254 (Step S2044).

After the processing in Step S2044, or when the second encrypted first share E2FSD is not included in the third data TD (No in Step S2041), in order to obtain vital data VD, the second decryption unit 251 decrypts the encrypted vital data EVD using the decryption key SK obtained (Step S2045) from the second encryption key DB 821 in the fifth storage unit 254. The second decryption unit 251 stores the vital data VD into the third vital data DB 820 in the fifth storage unit 254 to complete the sequential processes (Step S2046).

[(ii) Operations that Intermediate Device 23 Performs when Displaying Vital Data Using Measurement Device 21]

Figure 78:
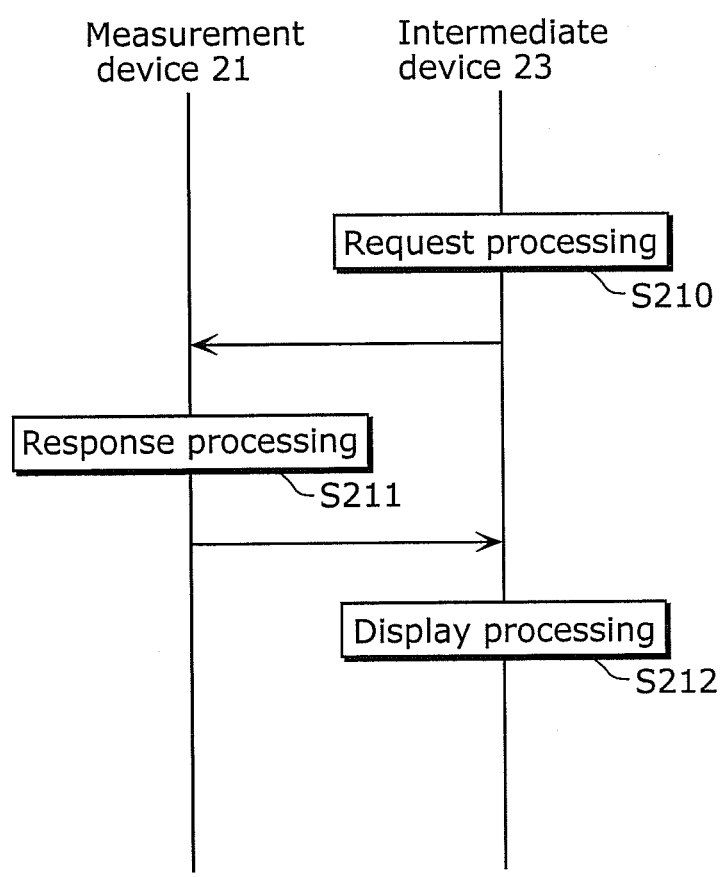
FIG. 78 is a flowchart of exemplary operations at the time of display of vital data in the health care system.

Hereinafter, with reference to a flowchart in FIG. 78, descriptions are given of operations performed by the intermediate device 23 to display the vital data.

The intermediate device 23 performs a "request process (Step S210)".

The measurement device 21 performs a "response process (Step S211)".

The intermediate device 23 performs a "display process (Step S212)" to complete the sequential processes.

Next, descriptions are given of operations performed by the respective structural elements of the intermediate device 23 to display the vital data.

Figure 79A:
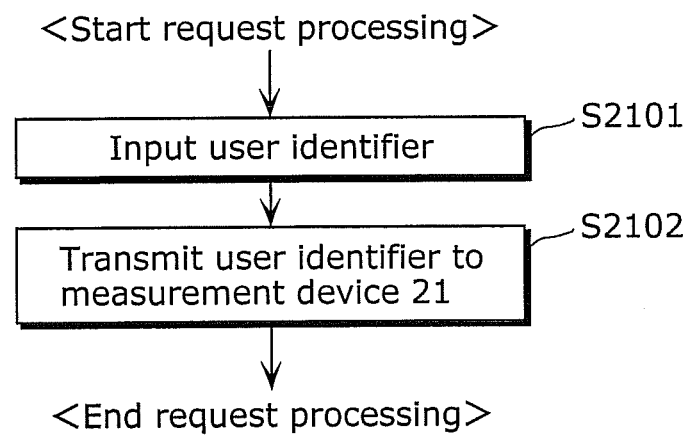
FIG. 79A is a flowchart showing details of "request processing" performed by the intermediate device.

[Details of Request Process (Step S210): see FIG. 79A]

The control unit 234 receives an input of a user identifier ID from the outside (Step S2101).

The reconstructed request processing unit 238 transmits the user identifier ID to the measurement device 21 (Step S2102).

Figure 79B:
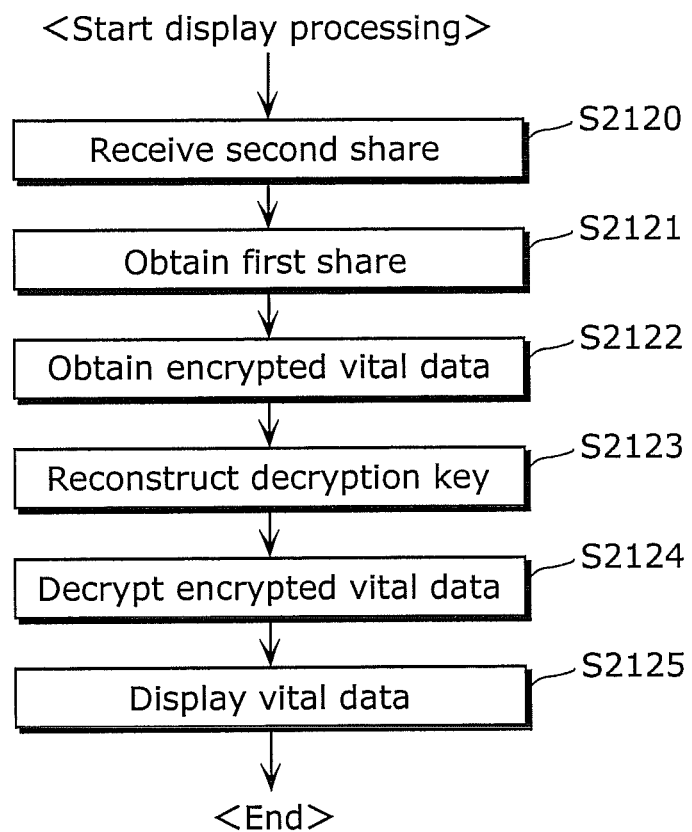
FIG. 79B is a flowchart showing details of "display processing" performed by the intermediate device.

[Details of Display Process (Step S212): see FIG. 79B]

The control unit 234 receives the second share SSD (Step S2120).

The control unit 234 obtains the first share FSD corresponding to the user identifier ID from the second share DB 510 in the second storage unit 231 (Step S2121).

The control unit 234 obtains the encrypted vital data EVD corresponding to the user identifier ID from the second vital data DB 511 in the second storage unit 231 (Step S2122).

The first decryption unit 233 reconstructs the decryption key SK from the first share FSD, the second share SSD, and the third share TSD (Step S2123).

The first decryption unit 233 decrypts the encrypted vital data EVD using the decryption key SK to obtain the vital data VD (Step S2124).

The display unit 232 displays vital data VD (Step S2125).

Figure 80:
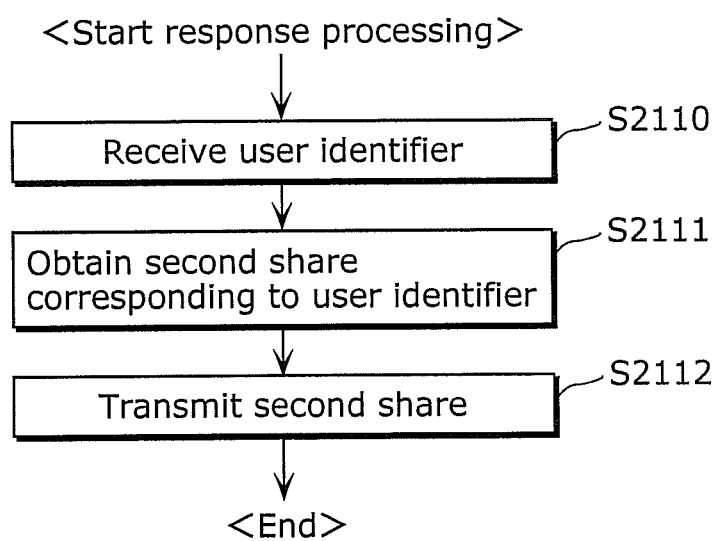
FIG. 80 is a flowchart showing details of the "response processing" performed by the measurement device.

[Details of Response Process (Step S211): FIG. 80]

The reconstructed response processing unit 217 receives a user identifier ID from the intermediate device 23 (Step S2110).

The reconstructed response processing unit 217 obtains the second share SSD from the share DB 500 in the first storage unit 213 (Step S2111).

The reconstructed response processing unit 217 transmits the second share SSD to the intermediate device 23 (Step S2112).

[(iii) Operations Performed to Set Share into Intermediate Device 23y when Intermediate in Use Device has Trouble]

Figure 81:
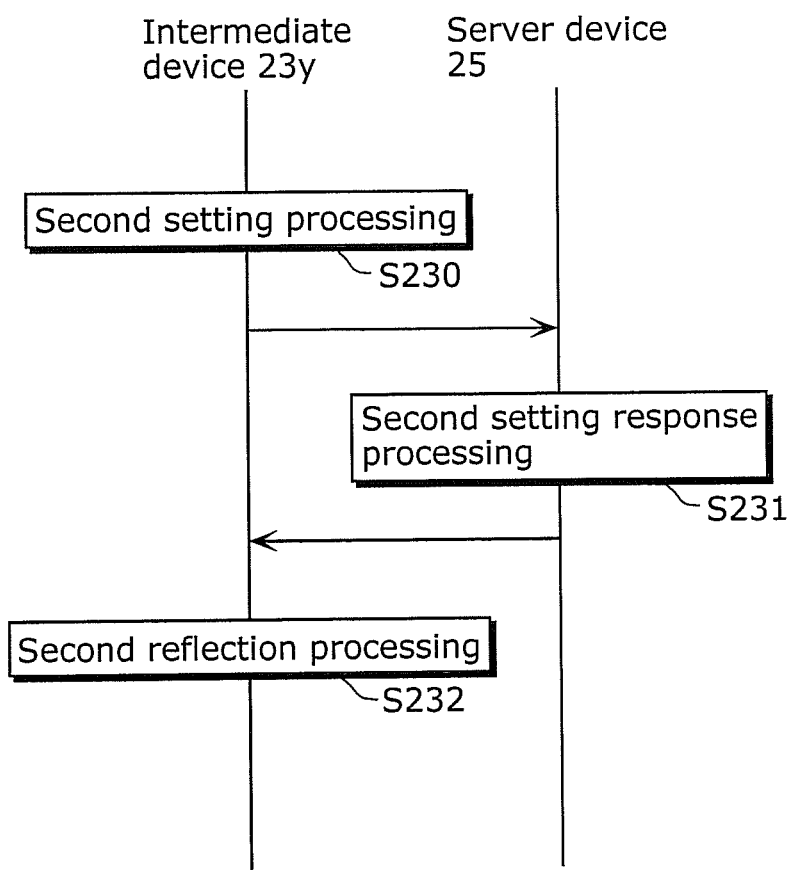
FIG. 81 is another diagram showing a concept of operations in the health care system.

Hereinafter, with reference to a flowchart in FIG. 81, descriptions are given of operations for setting the substitute intermediate device.

The intermediate device 23y performs a "second setting process (Step S230)".

The server device 25 performs a "second setting response process (Step S231)".

The intermediate device 23y performs a "second reflection process (Step S232)" to complete the sequential processes.

Next, a description is given of operations performed by the respective structural elements to set the substitute intermediate device.

Figure 82A:
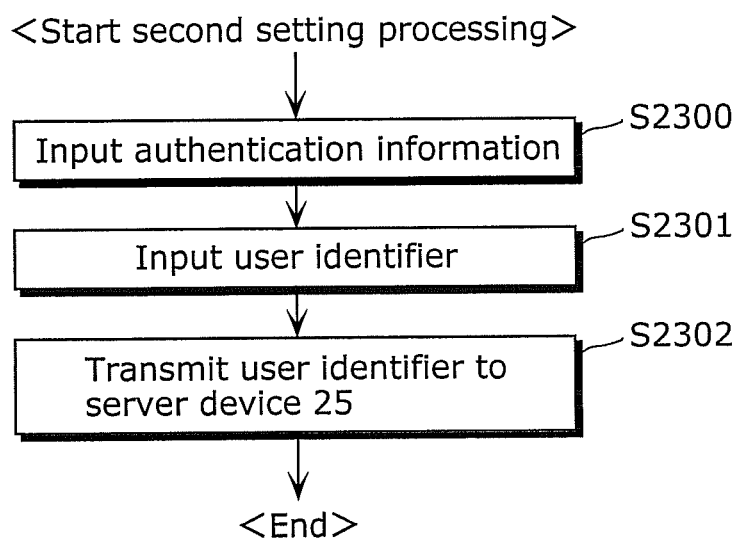
FIG. 82A is a flowchart showing details of "second setting processing" performed by the intermediate device.

[Details of Second Setting Process (Step S230): see FIG. 82A]

The second setting processing unit 239 receives an input of authentication information (Step S2300).

When the authentication information is correct, the second setting processing unit 239 receives an input of a user identifier ID (Step S2301).

The second setting processing unit 239 transmits the user identifier ID to the server device 25 (Step S2302).

Figure 82B:
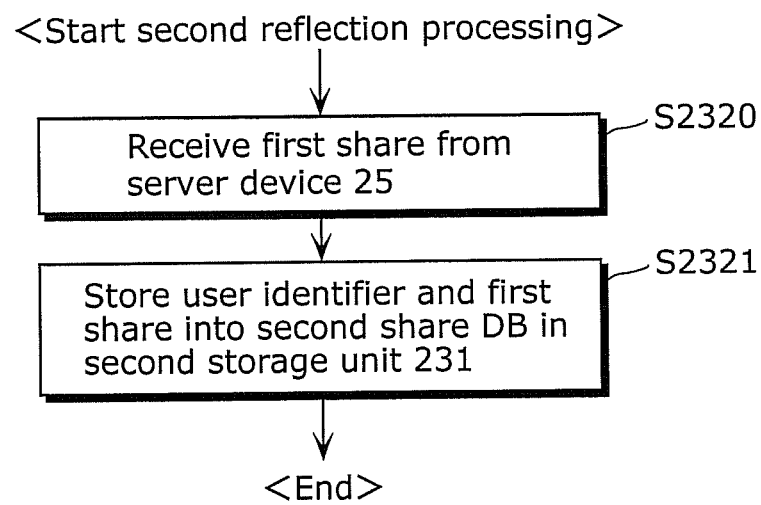
FIG. 82B is a flowchart showing details of "second reflection processing" performed by the intermediate device.

[Details of Second Reflection Process (Step S232): see FIG. 82B]

The second setting processing unit 239 receives the first share FSD from the server device 25 (Step S2320).

The second setting processing unit 239 stores the first share FSD into the second share DB 510 in the second storage unit 231 (Step S2321).

Figure 83:
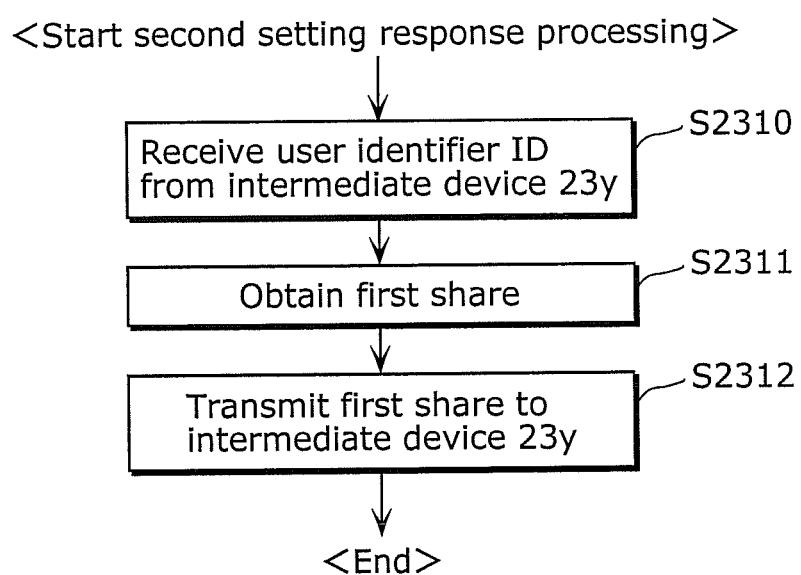
FIG. 83 is a flowchart showing details of "second setting response processing" performed by the server device.

[Details of Second Setting Response Process (Step S231): see FIG. 83]

The third setting processing unit 257 receives the user identifier ID from the intermediate device 23y (Step S2310).

The third setting processing unit 257 obtains the first share FSD corresponding to the user identifier ID from the third storage unit 252 (Step S2311).

The third setting processing unit 257 transmits the first share FSD to the intermediate device 23y (Step S2312).

[(iv) Operations Performed to Set Share into Measurement Device 21x when Measurement Device in Use has Trouble]

Figure 84:
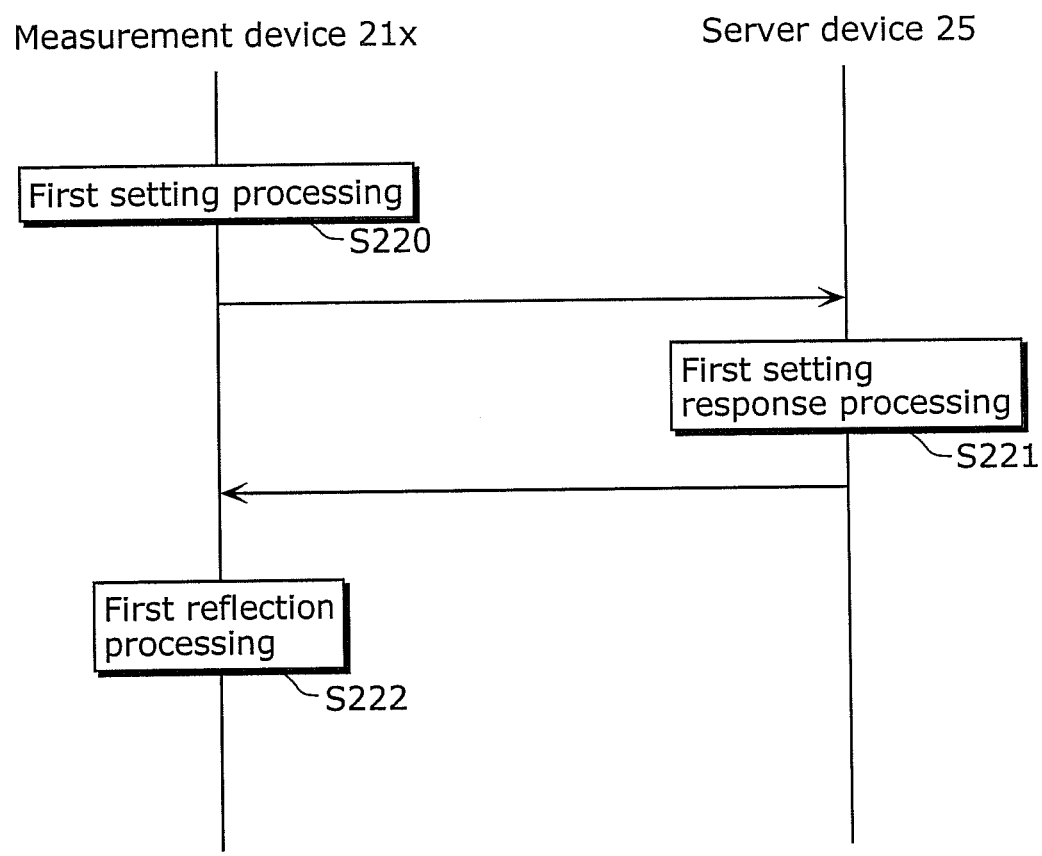
FIG. 84 is yet another diagram showing a concept of operations in the health care system.

Hereinafter, with reference to a flowchart in FIG. 84, descriptions are given of operations for setting the substitute measurement device.

The measurement device 21x performs a "first setting process (Step S220)".

The server device 25 performs a "first setting response process (Step S221)".

The measurement device 21x performs a "first reflection process (Step S222)" to complete the sequential processes.

Next, a description is given of operations performed by the respective structural elements to set the substitute measurement device.

Figure 85A:
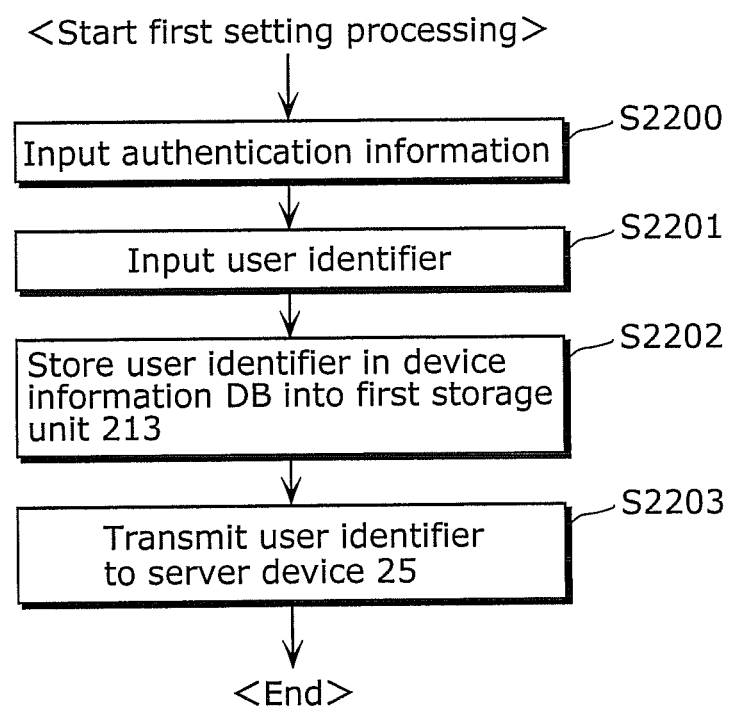
FIG. 85A is a flowchart showing details of the "first setting processing" performed by the measurement device.

[Details of First Setting Process (Step S220): see FIG. 85A]

The first setting processing unit 218 receives an input of authentication information (Step S2200).

When the authentication information is correct, the first setting processing unit 218 receives an input of a user identifier ID (Step S2201).

The first setting processing unit 218 stores the user identifier ID into the device information DB 503 in the first storage unit 213 (Step S2202).

The first setting processing unit 218 transmits the user identifier ID to the server device 25 (Step S2203).

Figure 85B:
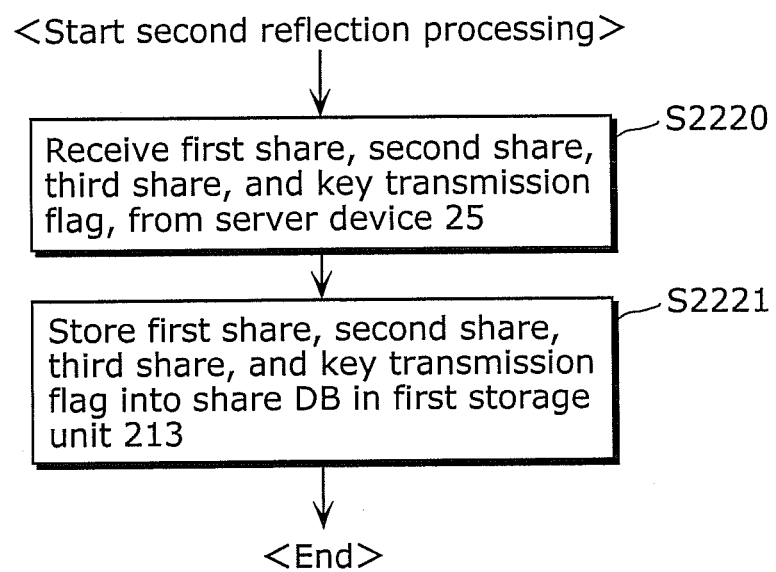
FIG. 85B is a flowchart showing details of the "first reflection processing" performed by the measurement device.

[Details of First Reflection Process (Step S222): see FIG. 85B]

The first setting processing unit 218 receives, from the server device 25, the first share FSD, the second share SSD, the third share TSD, and the key transmission flag SF (Step S2220).

The first setting processing unit 218 stores the first share FSD, the second share SSD, the third share TSD, and the key transmission flag SF into the share DB 500 in the first storage unit 213 (Step S2221).

Figure 86:
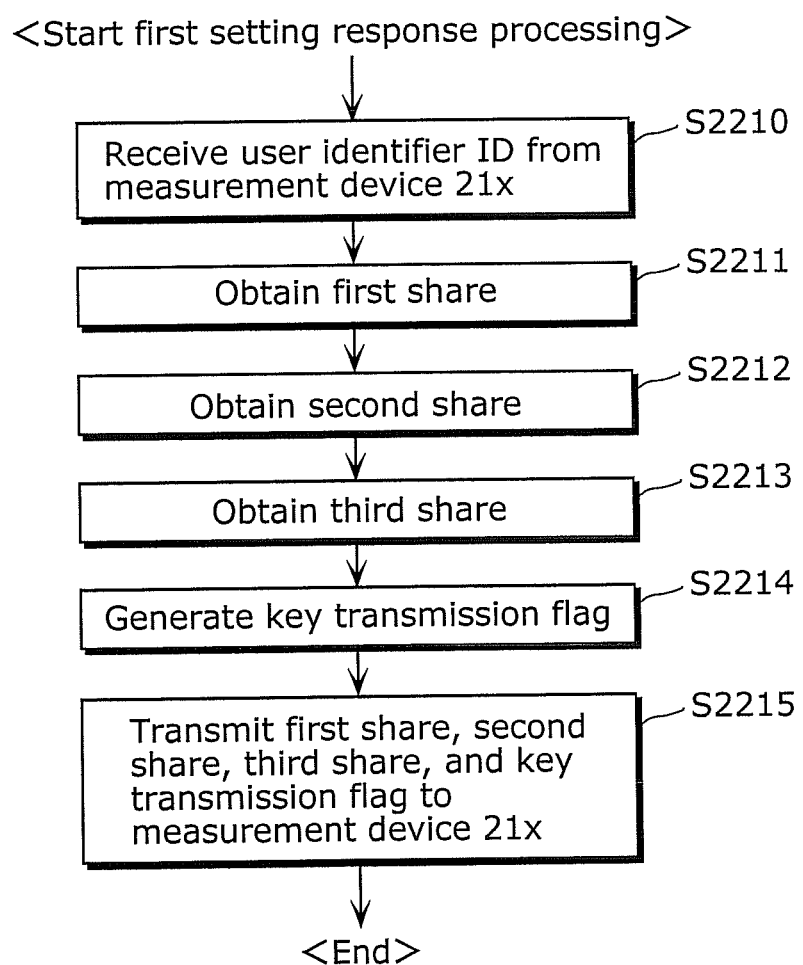
FIG. 86 is a flowchart showing details of "first setting response processing" performed by the server device.

[Details of First Setting Response Process (Step S221): see FIG. 86]

The third setting processing unit 257 receives the user identifier ID from the measurement device 21x (Step S2210).

The third setting processing unit 257 obtains the first share FSD corresponding to the user identifier ID from the third storage unit 252 (Step S2211).

The third setting processing unit 257 obtains the second share SSD corresponding to the user identifier ID from the fourth storage unit 253 (Step S2212).

The third setting processing unit 257 obtains the third share TSD corresponding to the user identifier ID from the fifth storage unit 254 (Step S2213).

The third setting processing unit 257 generates a key transmission flag SF indicating "Yes (already transmitted)" (Step S2214).

The third setting processing unit 257 transmits the first share FSD, the second share SSD, the third share TSD, and the key transmission flag SF to the measurement device 21x (Step S2215).

[(v) Operations that Intermediate Device 23 Performs when Displaying Vital Data Using Access Device 26]

Figure 87:
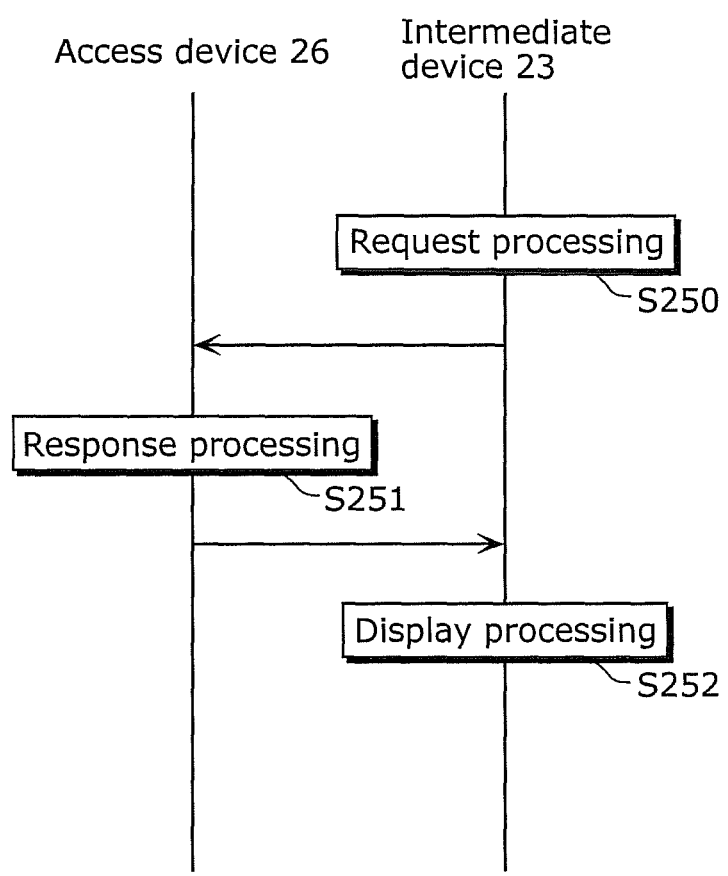
FIG. 87 is yet another diagram showing a concept of operations in the health care system.

Hereinafter, with reference to a flowchart in FIG. 87, descriptions are given of operations performed by the intermediate device 23 to display the vital data.

The intermediate device 23 performs a "request process (Step S250)".

The access device 26 performs a "response process (Step S251)".

The intermediate device 23 performs a "display process (Step S252)" to complete the sequential processes.

Next, descriptions are given of operations performed by the respective structural elements of the intermediate device 23 to display the vital data.

Figure 88A:
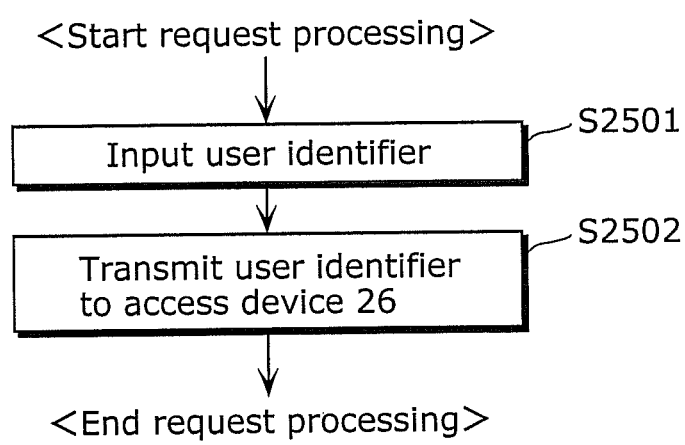
FIG. 88A is a flowchart showing details of "request processing" performed by the intermediate device.

[Details of Response Process (Step S250): FIG. 88A]

The control unit 234 receives an input of a user identifier ID from the outside (Step S2501).

The reconstructed request processing unit 238 transmits the user identifier ID to the access device 26 (Step S2502).

Figure 88B:
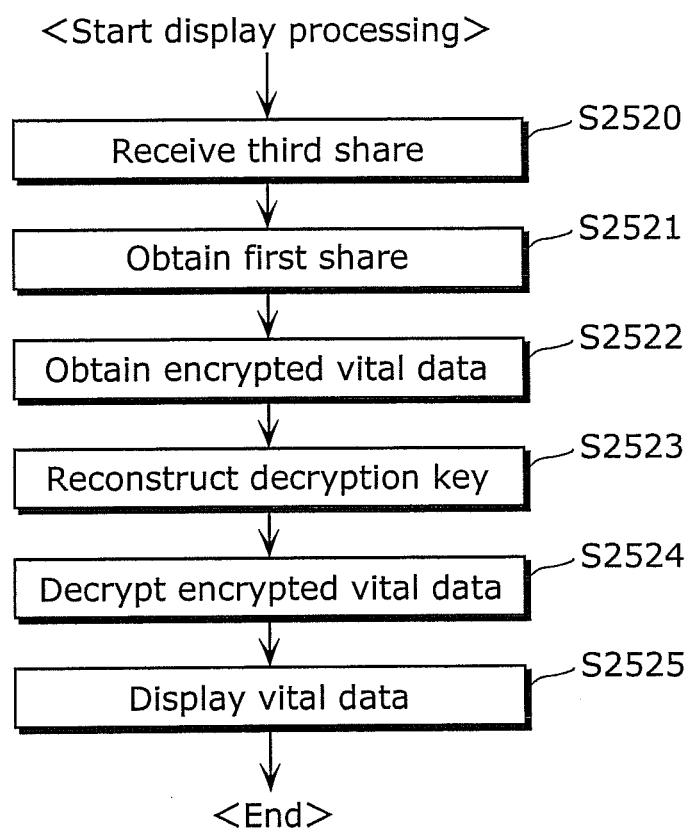
FIG. 88B is a flowchart showing details of "display processing" performed by the intermediate device.

[Details of Display Process (Step S252): see FIG. 88B]

The control unit 234 receives the third share TSD (Step S2520).

The control unit 234 obtains the first share FSD corresponding to the user identifier ID from the second share DB 510 in the second storage unit 231 (Step S2521).

The control unit 234 obtains the encrypted vital data EVD corresponding to the user identifier ID from the second vital data DB 511 in the second storage unit 231 (Step S2522).

The first decryption unit 233 reconstructs the decryption key SK from the first share FSD and the third share TSD (Step S2523).

The first decryption unit 233 decrypts the encrypted vital data EVD using the decryption key SK to obtain the vital data VD (Step S2524).

The display unit 232 displays vital data VD (Step S2525).

Figure 89:
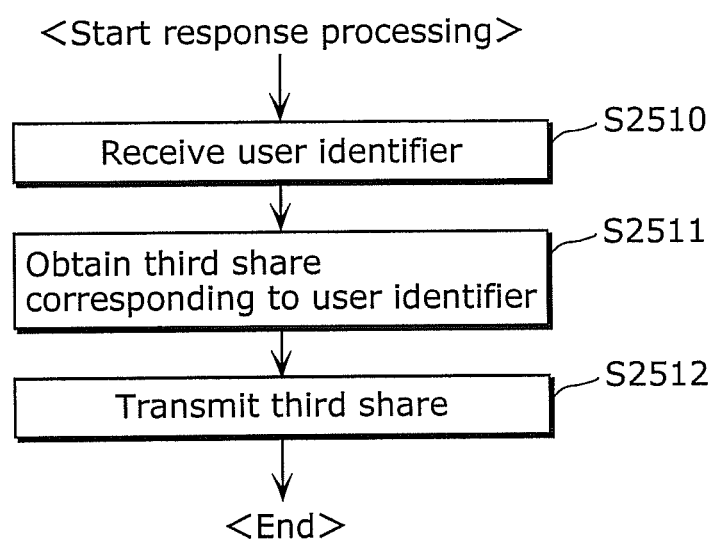
FIG. 89 is a flowchart showing details of the "response processing" performed by the access device.

[Details of Response Process (Step S251): FIG. 89]

The reconstructed response processing unit 267 receives a user identifier ID from the intermediate device 23 (Step S2510).

The reconstructed response processing unit 267 obtains the third share TSD from the share DB 520 in the sixth storage unit 263 (Step S2511).

The reconstructed response processing unit 267 transmits the third share TSD to the intermediate device 23 (Step S2512).

[(vi) Operations Performed to Set Share into Access Device 26z when Access Device in Use has Trouble]

Figure 90:
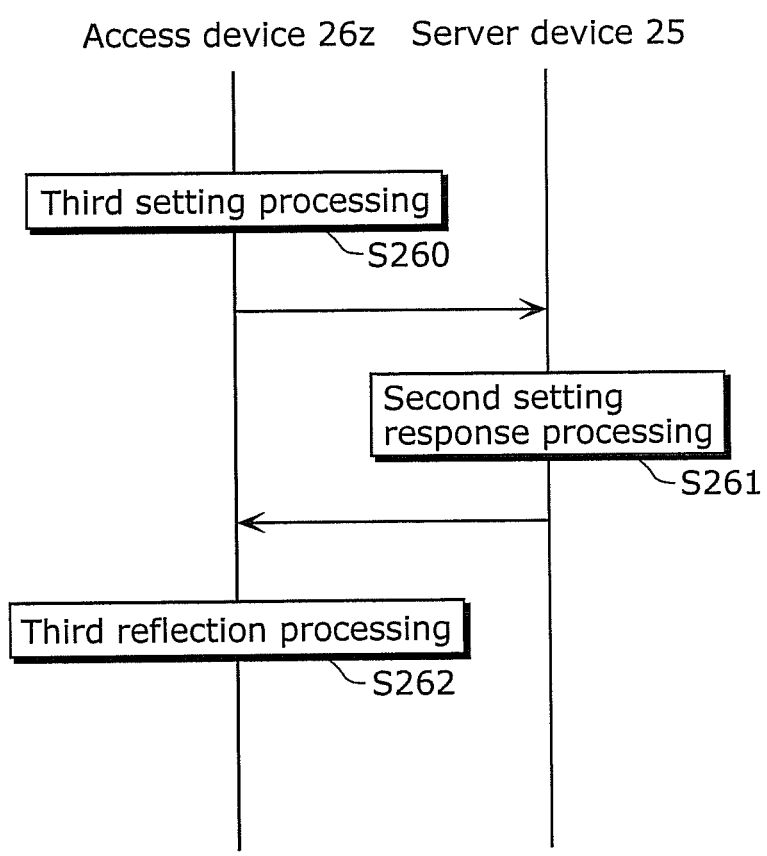
FIG. 90 is a flowchart of exemplary operations at the time of setting a substitute access device in the health care system.

Hereinafter, with reference to a flowchart in FIG. 90, descriptions are given of operations for setting the substitute access device.

The access device 26z performs a "third setting process (Step S260)".

The server device 25 performs a "third setting response process (Step S261)".

The access device 26z performs a "third reflection process (Step S262)" to complete the sequential processes.

Next, a description is given of operations performed by the respective structural elements to set the substitute access device.

Figure 91A:
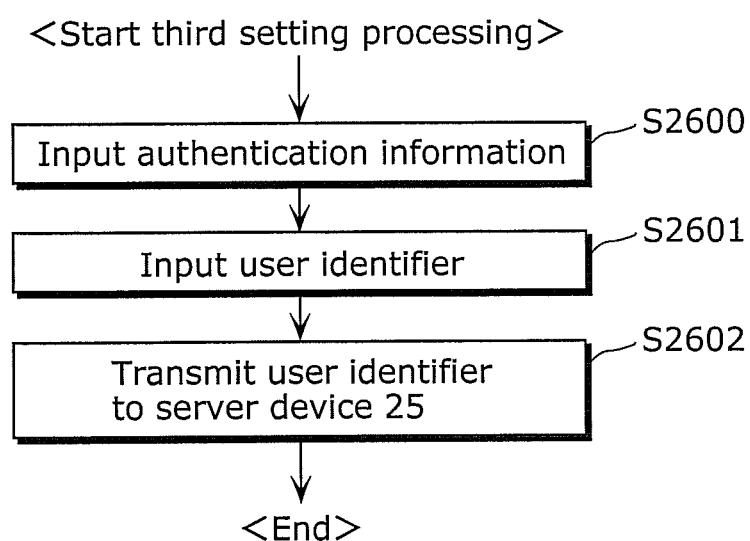
FIG. 91A is a flowchart showing details of "third setting processing" performed by the intermediate device.

[Details of Third Setting Process (Step S260): see FIG. 91A]

Next, a description is given of detailed operations performed by the respective structural elements.

The fourth setting processing unit 268 receives an input of authentication information (Step S2600).

When the authentication information is correct, the fourth setting processing unit 268 receives an input of a user identifier ID (Step S2601).

The fourth setting processing unit 268 transmits the user identifier ID to the server device 25 (Step S2602).

Figure 91B:
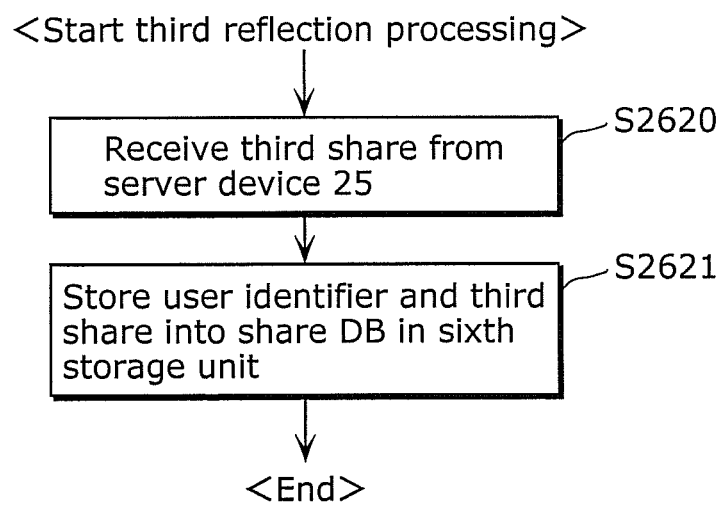
FIG. 91B is a flowchart showing details of "third reflection processing" performed by the intermediate device.

[Details of Second Reflection Process (Step S262): see FIG. 91B]

The fourth setting processing unit 268 receives the third share TSD from the server device 25 (Step S2620).

The fourth setting processing unit 268 stores the user identifier ID and the third share TSD into the share DB 520 in the sixth storage unit 263 (Step S2621).

Figure 92:
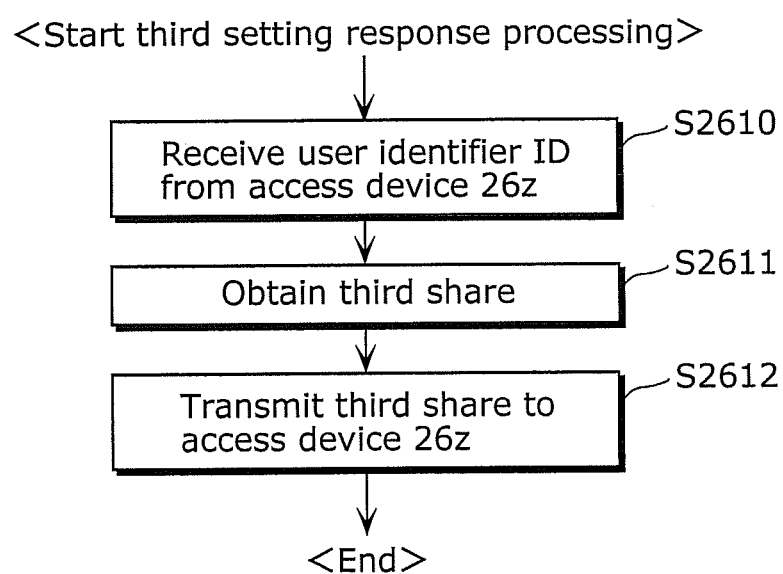
FIG. 92 is a flowchart showing details of "third setting response processing" performed by the server device.

[Details of Second Setting Response Process (Step S261): see FIG. 92]

The third setting processing unit 257 receives the user identifier ID from the access device 26z (Step S2610).

The third setting processing unit 257 obtains the third share TSD corresponding to the user identifier ID from the seventh storage unit 258 (Step S2611).

The third setting processing unit 257 transmits the third share TSD to the access device 26z (Step S2612).

The above descriptions have been given of the exemplary operations performed by the measurement device 21, intermediate device 23, sever device 25, and access device 26 which are structural elements of the health care system according to an aspect of the present invention.

(Advantageous Effect of Embodiment 2)

The access device 26 further holds the third share TSD, in addition to shares stored in Embodiment 1. In this way, both the second share SSD and the third share TSD become available when the intermediate device 23 obtains the third share TSD from the access device 26, the intermediate device 23 can reproduce the decryption key, and thereby can reproduce and display the vital data encrypted using the encryption key. This makes it is possible to check the vital data VD on the display unit 232 of the intermediate device 23 also when the measurement device 21 and the access device 26 are present at a same place. Therefore, it is possible to increase the convenience for the operator of the intermediate device 23, and prevent the vital data VD from leaking when the intermediate device 23 is lost.

It is to be noted that the access device cannot independently obtain two shares, and thus that it is impossible for a third party to reconstruct the decryption key using only the access device even if the access device is lost. Accordingly, it is possible to securely distribute the share even when it is impossible to directly transmit the share from the measurement device to the server device.

(Variation)

The above-described embodiments are mere exemplary embodiments according to the present invention. Thus, the present invention is not limited by these embodiments, and can be implemented as embodiments obtained by modifying the above embodiments within the scope of the present invention. The following cases are also included in the scope of the present invention.

(1) Methods for distributing the respective shares are not limited to the methods as described above. For example, by increasing the number of devices and the number of shares, it is possible to increase the number of times of browsing vital data using the intermediate device.

(2) The numbers of shares is not limited to the numbers of the shares disclosed in the above embodiments. For example, even in the case of Embodiment 1, it is possible to generate (2×N) number of shares, and distribute each unit of N shares among the (2×N) number of shares to a corresponding one of the intermediate device and the measurement device (here, N denotes a natural number equal to or greater than 2).

Figure 93:
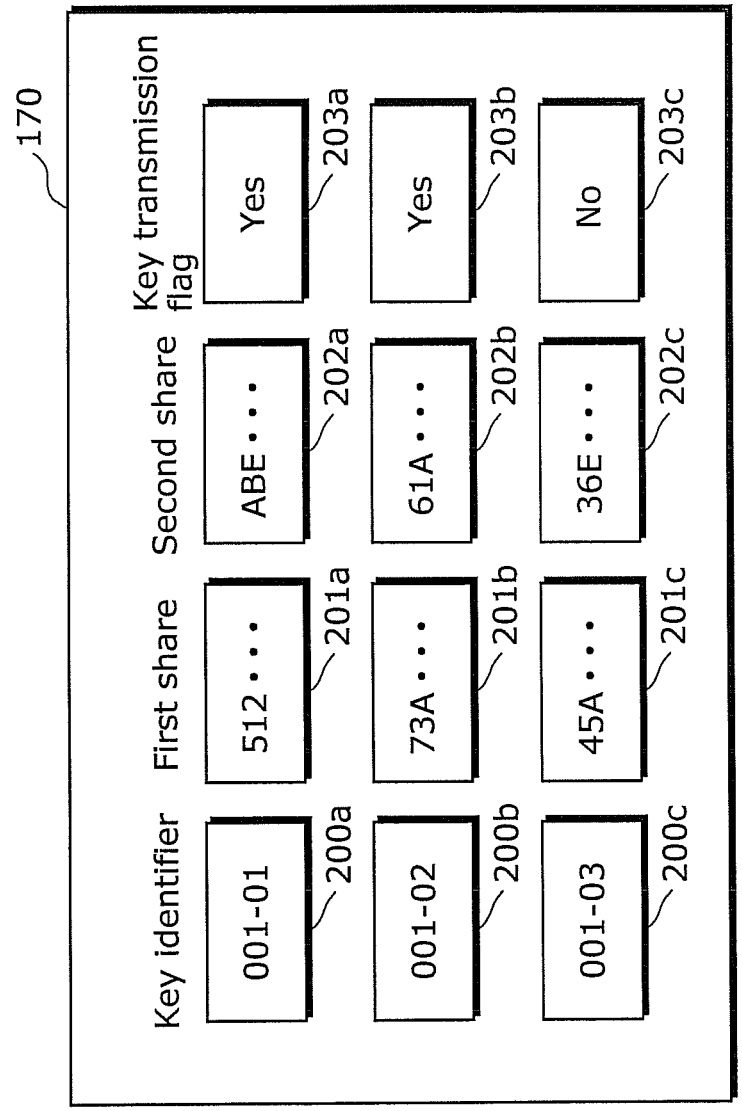
FIG. 93 is a diagram showing a structure of a share DB in (3) of Variation.

(3) Although the measurement devices hold a pair of encryption key and a decryption key in the respective embodiments, data that can be held are not limited thereto. For example, such an encryption key and a decryption key may be updated in units of a predetermined time period. This is achievable by assigning a key identifier to the pair of the encryption key and the decryption key. For example, as shown in FIG. 93, the share DB includes one or more sets of a key identifier, a first share FSD, a second share SSD, and a key transmission flag SF (the number of the sets is three in FIG. 93). For example, one of the sets is the set composed of a key identifier 200a, a first share 201a, a second share 202a, and a key transmission flag 203a. In addition, as shown in FIG. 94, the encryption key DB 172 includes one or more pairs of a key identifier, an encryption key PK, a decryption key SK, and a valid period (the number of the sets is three in FIG. 94). For example, one of the sets is the set composed of a key identifier 220a, an encryption key 221a, a decryption key 222a, and a valid period 223a.

Figure 95:
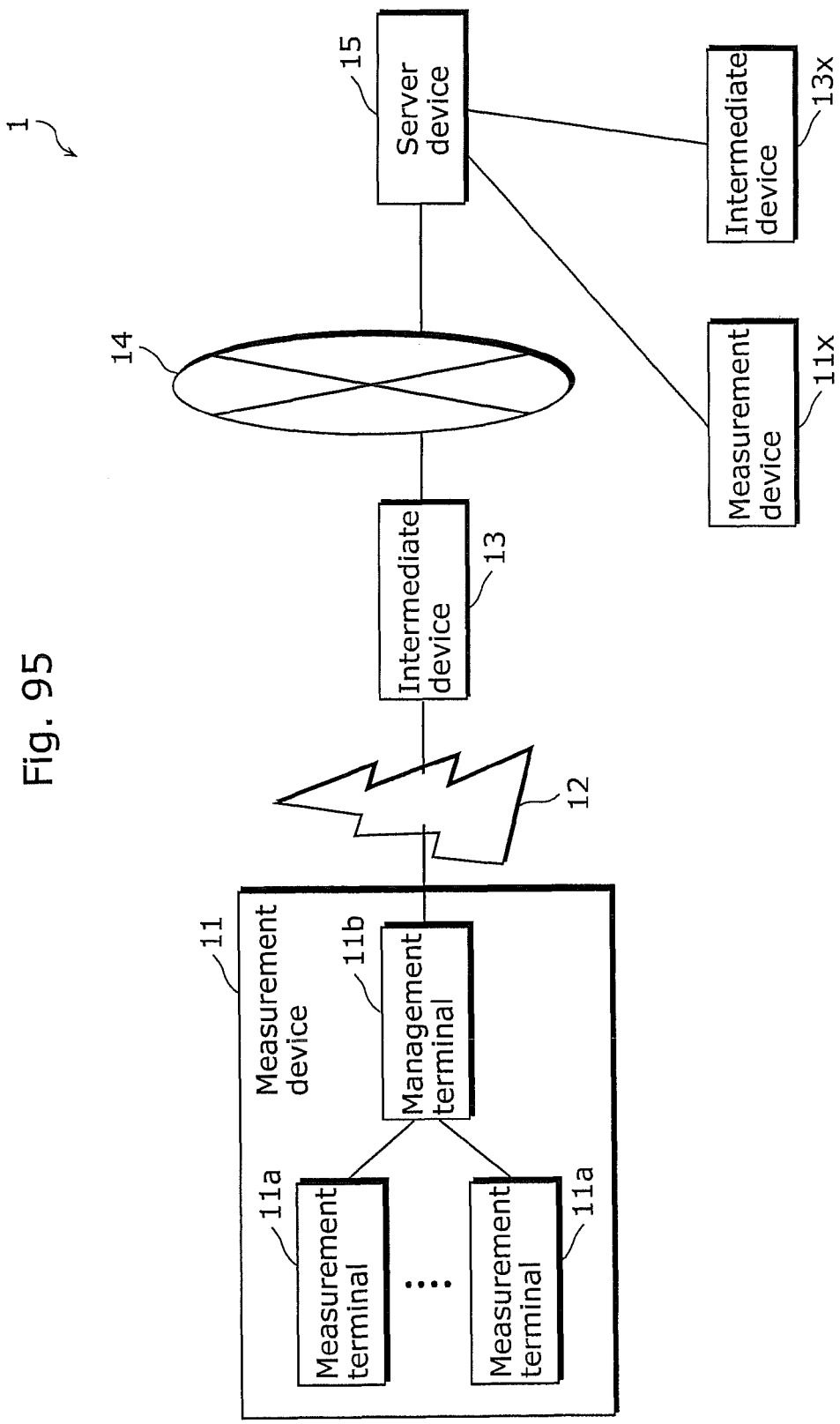
FIG. 95 is a block diagram showing a structure of a health care system in (4) of Variation.

(4) The measurement device may be configured with at least one measurement terminal and a management terminal which collects vital data measured by each of the at least one measurement device and transmits the collected vital data to an intermediate device. FIG. 95 is a block diagram showing a structure of a health care system including such a measurement device. The measurement device 11 includes at least one measurement terminal 11a, and a management terminal 11b connected to each of the at least one measurement terminal 11a.

Figure 96:
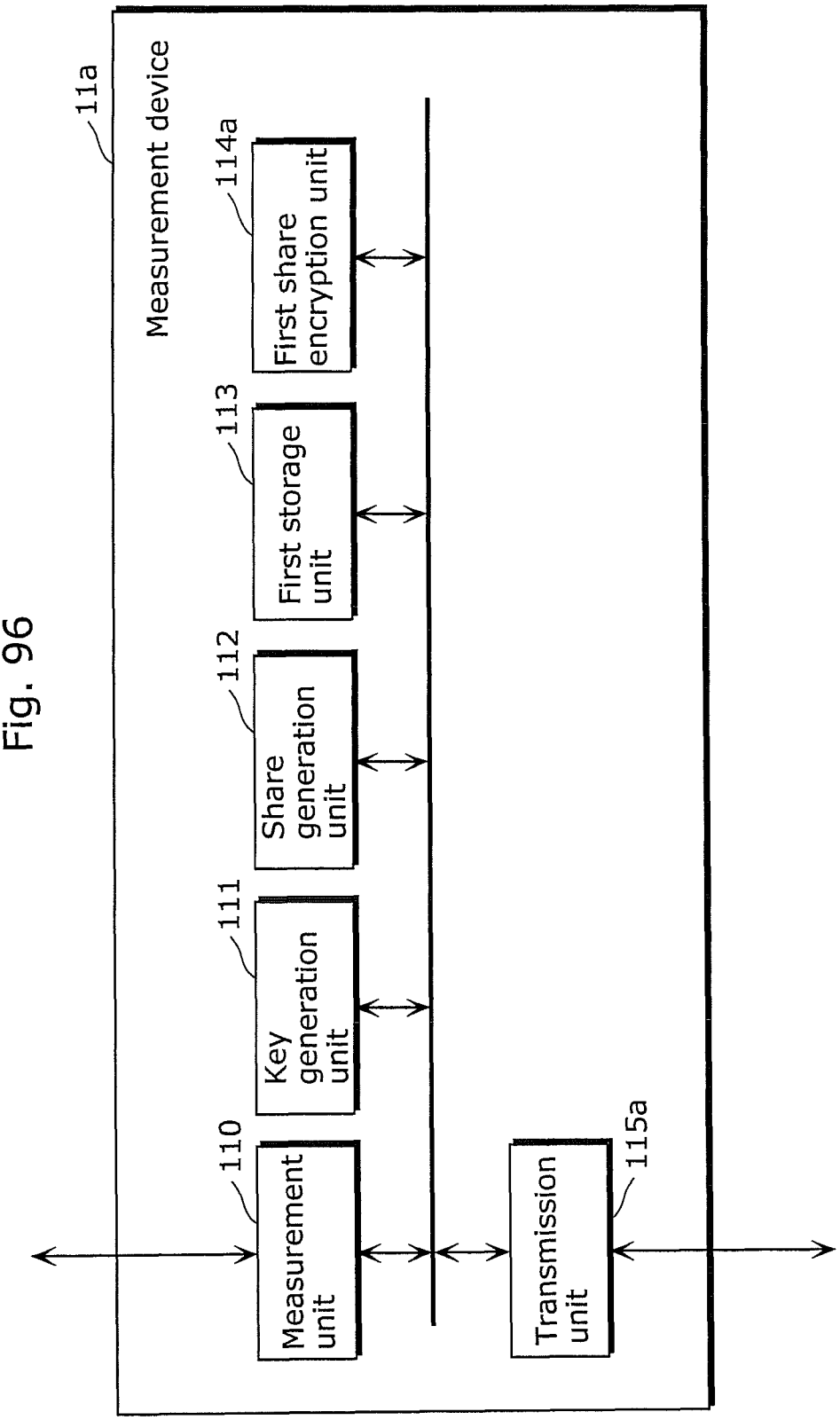
FIG. 96 is a block diagram showing a structure of a measurement terminal in (4) of Variation.

FIG. 96 is a block diagram showing a structure of the measurement terminal 11a. The measurement terminal 11a includes a measurement unit 110, a key generation unit 111, a share generation unit 112, a first storage unit 113, a first share encryption unit 114a, and a transmission unit 115a. The structures of the measurement unit 110, the key generation unit 111, the share generation unit 112, and the first storage unit 113 are the same as those in Embodiment 1. The first share encryption unit 114a performs encryption of the vital data VD and the encryption of the first share FSD among the processes performed by the first encryption unit 114 as shown in Embodiment 1. The transmission unit 115a transmits, to the management terminal 11b, the encrypted vital data EVD, the encrypted first share EFSD, and the second share SSD.

Figure 97:
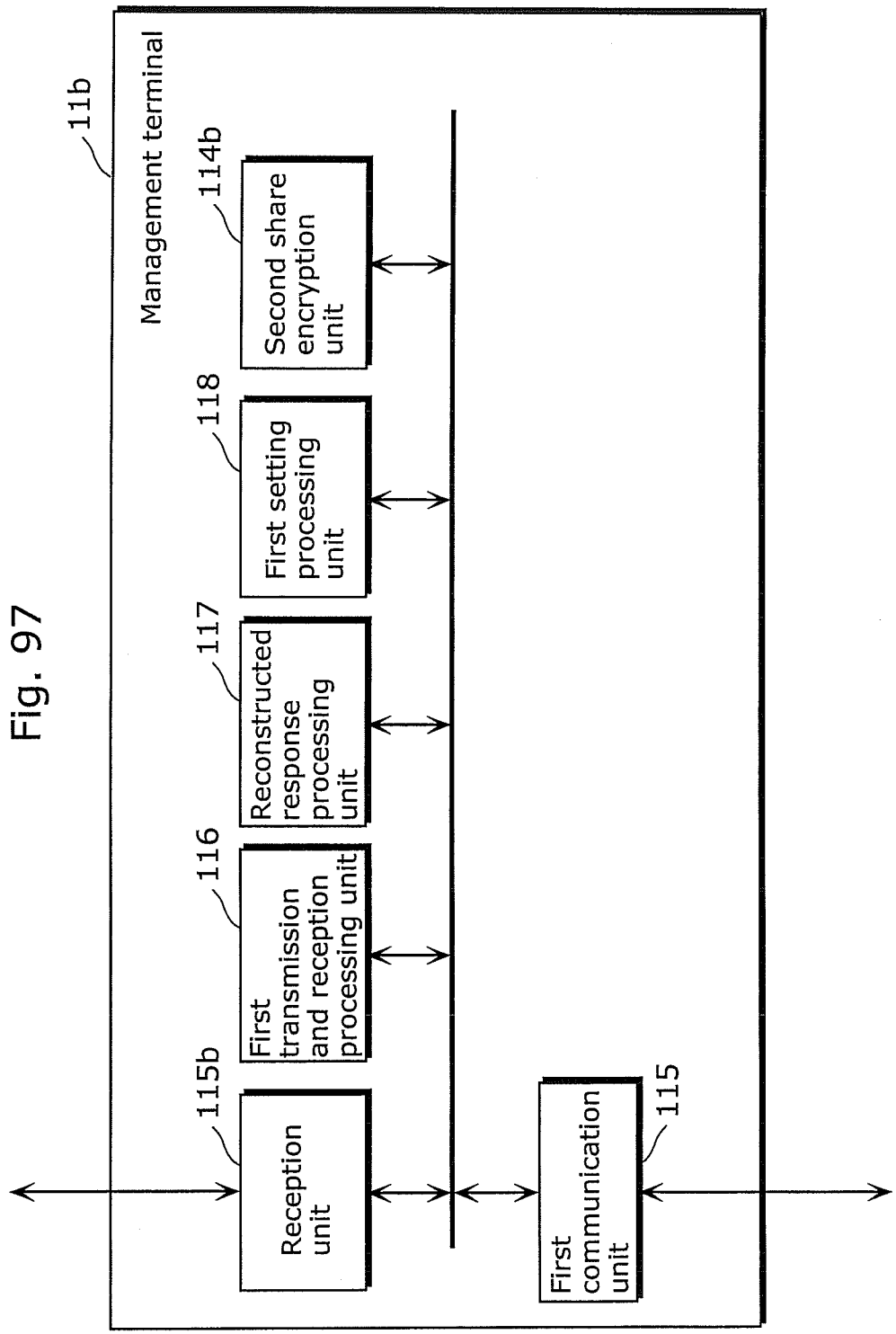
FIG. 97 is a block diagram showing a structure of a management terminal in (4) of Variation.

FIG. 97 is a block diagram showing a structure of the management terminal 11b. The management terminal 11b includes a reception unit 115b, a first transmission and reception processing unit 116, a reconstructed response processing unit 117, a first setting processing unit 118, a second share encryption unit 114b, and a first communication unit 115. The first transmission and reception processing unit 116, the reconstructed response processing unit 117, the first setting processing unit 118, and the first communication unit 115 are the same as those in Embodiment 1. The reception unit 115b receives, from the measurement terminal 11a, the encrypted vital data EVD, the encrypted first share EFSD, and the second share SSD. The second share encryption unit 114b performs the encryption of the second share SSD among the processes performed by the first encryption unit 114 as shown in Embodiment 1.

In this way, separately encrypting the two shares using the terminals makes it difficult to reconstruct the shares in the case where the data leaks to the outside.

(5) Although the first share FSD that is transmitted from the measurement device to the intermediate device and the first share FSD that is transmitted from the intermediate device to the server device are encrypted in the respective embodiments, encryption of the first share FSD and the second share FSD may be skipped. Furthermore, although the third share TSD that is transmitted from the access device 26 to the server device 25 is also encrypted in one of the above embodiments, encryption of the third share TSD may also be skipped.

(6) Although the public key encryption scheme is used as the encryption scheme in the embodiments, but the encryption scheme for use therein is not limited to the used one. For example, it is possible to use the secret key encryption scheme in which a common key functions as both an encryption key and a decryption key. For example, the Advanced Encryption Standard (AES) scheme may be used.

(7) Although the vital data is encrypted using the public key encryption scheme in each of the above embodiments, the encryption scheme for use is not limited thereto. For example, a hybrid encryption scheme may be used for the encryption. More specifically, it is possible to encrypt the vital data using a session key that is temporarily generated using a secret key encryption, encrypt the temporarily generated session key using an encryption key that is a public key, and perform sharing on the decryption key corresponding to the encryption key.

(8) Although each of the embodiments focuses on the encryption of the vital data, focuses may be placed on other things in the present invention. For example, it is possible to generate a digital signature of vital data when a certain number or more of shares are collected.

(9) The secret sharing schemes for use are not limited to the secret sharing schemes as described in the above embodiments. It is possible to replace the secret sharing schemes used above with other secret sharing schemes having the similar functions.

(10) Each of the aforementioned devices is, for example, a computer system composed of a microprocessor, a ROM, a RAM, a hard disc unit, a display unit, a keyboard, a mouse, etc. The RAM or the hard disc unit has a computer program recorded therein. Each of the devices achieves its functions through the microprocessor's operations according to the computer program. Here, the computer program is programmed with a combination of instruction codes each of which indicates a command to the computer to achieve a corresponding one of the predetermined functions.

(11) A part or all of the structural elements of the respective devices may be configured with a single system LSI (Large Scale Integration). The system LSI is a super-multi-functional LSI manufactured by integrating structural elements on a single chip, and is specifically a computer system configured to include a microprocessor, a ROM, a RAM, and so on. A computer program is stored in the RAM. The system LSI achieves its functions through the microprocessor's operations according to the computer program.

(12) A part or all of the constituent elements constituting the respective devices may be configured as an IC card which can be attached to and detached from the respective devices or as a stand-alone module. The IC card or the module is a computer system configured with a microprocessor, a ROM, a RAM, and so on. The IC card or the module may also be included in the aforementioned super-multi-function LSI. The IC card or the module achieves its functions through the microprocessor's operations according to the computer program. The IC card or the module may also be implemented to be tamper-resistant.

(13) The present invention may be implemented as the methods described above. Furthermore, these methods may be implemented as computer programs executed by computers, or as digital signals representing the computer programs.

(14) Furthermore, the present invention may also be implemented as computer programs or digital signals recorded on computer-readable recording media such as a flexible disc, a hard disk, a CD-ROM, an MO, a DVD, a DVD-ROM, a DVD-RAM, a Blu-ray (trademark) (BD) Disc, a semiconductor memory, and the like. Furthermore, the present invention may also be implemented as the digital signals recorded on these recording media.

(15) Furthermore, the present invention may also be implemented as the aforementioned computer programs or digital signals transmitted via a telecommunication line, a wireless or wired communication line, a network represented by the Internet, a data broadcast, and so on.

(16) Furthermore, the present invention may also be implemented as a computer system including a microprocessor and a memory, in which the memory stores the aforementioned computer program and the microprocessor operates according to the computer program.

(17) Furthermore, it is also possible to execute another independent computer system by transmitting the programs or the digital signals recorded on the aforementioned recording media, or by transmitting the programs or digital signals via the aforementioned network and the like.

(18) The above-described embodiments and variations may be arbitrarily combined.

The embodiments disclosed above are exemplary in all respects, and should be interpreted as not limiting the present invention. The scope of the present invention is defined by the CLAIMS of the present application not by the DESCRIPTION of the present application, and all possible modifications having equivalents to those in the CLAIMS and within the scope of the CLAIMS are intended to be included in the scope of the present invention.

The present invention is particularly applicable as a health care system etc. which achieves both the confidentiality of confidential data and convenience for an operator.

REFERENCE SIGNS LIST 1, 2 Health care system
11, 21 Measurement device
12, 22 First computer network
13, 23 Intermediate device
14, 24 Second computer network
15, 25 Server device 26 Access device
110, 210 Measurement unit
111, 211 Key generation unit
112, 212 Share generation unit
113, 213 First storage unit
114, 214 First encryption unit
115, 215 First communication unit
116, 216 First transmission and reception processing unit
117, 217 Reconstructed response processing unit
118, 218 First setting processing unit
130, 230 Second communication unit
131, 231 Second storage unit
132, 232 Display unit
133, 233 First decryption unit
134, 234 Control unit
135, 235 Second encryption unit
136, 236 Third communication unit
137, 237 Second transmission and reception processing unit
138, 238 Reconstructed request processing unit
139, 239 Second setting processing unit
150, 250 Fourth communication unit
151, 251 Second decryption unit
152, 252 Third storage unit
153, 253 Fourth storage unit
154, 254 Fifth storage unit
155, 255 Third encryption unit
156, 256 Third transmission and reception processing unit
157, 257 Third setting processing unit
258 Seventh storage unit
260 Fifth communication unit
263 Sixth storage unit
264 Fourth encryption unit
265 Sixth communication unit
266 Fourth transmission and reception processing unit
267 Reconstructed response processing unit
268 Fourth setting processing unit

The invention claimed is:

1. A health care system for measuring vital data, comprising:
   a measurement device which measures the vital data;
   a server device which collects the vital data; and
   an intermediate device which receives encrypted vital data from the measurement device, and transmits the encrypted vital data to the server device,
   wherein the measurement device includes:
   a measurement unit configured to measure the vital data of a patient;
   a vital data encryption unit configured to encrypt the vital data using a first encryption key generated by the measurement device to generate encrypted vital data;
   a share generation unit configured to generate a first share and a second share of a first decryption key which is for decrypting the encrypted vital data and generated by the measurement device, the first share and the second share being two mutually different shares which enable reconstruction of the first decryption key only when both of the two shares are available;
   a second share encryption unit configured to generate an encrypted second share by encrypting the second share generated by the share generation unit using a second encryption key corresponding to a second decryption key that is stored in the server device but is not stored in the intermediate device; and
   a first communication unit configured to transmit, to the intermediate device, the encrypted vital data generated by the vital data encryption unit, the first share generated by the share generation unit, and the encrypted second share generated by the second share encryption unit,
   the intermediate device includes:
   a second communication unit configured to receive, from the measurement device, the encrypted vital data, the first share, and the encrypted second share; and
   a third communication unit configured to transmit, to the server device, the encrypted vital data, the first share, and the encrypted second share received by the second communication unit, and
   the server device includes:
   a fourth communication unit configured to receive, from the intermediate device, the encrypted vital data, the first share, and the encrypted second share;
   a share decryption unit configured to decrypt the encrypted second share received by the fourth communication unit using the second decryption key stored in the server device, to generate the second share;
   a reconstruction unit configured to reconstruct the first decryption key for decrypting the encrypted vital data using the first share received by the fourth communication unit and the second share generated by the share decryption unit; and
   a vital data decryption unit configured to decrypt the encrypted vital data received by the fourth communication unit, using the first decryption key reconstructed by the reconstruction unit, to generate the vital data.

2. The health care system according to claim 1,
   wherein the first communication unit is further configured to transmit the second share to the intermediate device,
   the second communication unit is further configured to receive the second share from the measurement device,
   the intermediate device further includes:
   a storage unit configured to store only the first share received by the second communication unit;
   an intermediate device side vital data decryption unit configured to reconstruct the first decryption key for decrypting the encrypted vital data using the first share stored in the storage unit and the second share received by the second communication unit, and decrypt the encrypted vital data received by the second communication unit using the reconstructed first decryption key, to generate the vital data; and
   a display unit configured to display the vital data generated by the intermediate device side vital data decryption unit.

3. The health care system according to claim 1,
   wherein the measurement device further includes
   a first share encryption unit configured to encrypt the first share generated by the share generation unit using a third encryption key corresponding to a third decryption key stored in the intermediate device, to generate an encrypted first share,
   the first communication unit is configured to transmit, to the intermediate device, the encrypted vital data generated by the vital data encryption unit, the encrypted first share generated by the first share encryption unit, and the encrypted second share generated by the second share encryption unit, and
   the second communication unit receives, from the measurement device, the encrypted vital data, the encrypted first share, and the encrypted second share, and
   the intermediate device further includes
   a first share decryption unit configured to decrypt the encrypted first share received by the second communication unit using the third decryption key stored in the intermediate device, to generate the first share.

4. The health care system according to claim 3,
wherein the first share decryption unit is further configured to encrypt the first share generated by the first share decryption unit using the second encryption key corresponding to the second decryption key stored in the server device, to generate a second encrypted first share, the third communication unit is configured to transmit, to the server device, the encrypted vital data received by the second communication unit, the second encrypted first share generated by the first share decryption unit and the encrypted second share received by the second communication unit, the fourth communication unit is configured to receive, from the intermediate device, the encrypted vital data, the second encrypted first share, and the encrypted second share, the share decryption unit is further configured to decrypt the second encrypted first share using the second decryption key stored in the server device, to generate the first share, and the reconstruction unit is configured to reconstruct the first decryption key for decrypting the encrypted vital data using the first share and the second share generated by the share decryption unit.

5. The health care system according to claim 1, the health care system further comprising:

an access device which receives the vital data from the intermediate device, and transmits the received vital data to the server device, wherein the share generation unit is configured to generate a third share from the first decryption key for decrypting the encrypted vital data, wherein the first share, the second share, and the third share are different from each other and enable reconstruction of the first decryption key when selected as two shares available for the reconstruction, the measurement device further includes a third share encryption unit configured to encrypt the third share generated by the share generation unit using a fourth encryption key corresponding to a fourth decryption key stored in the access device, to generate an encrypted third share, the first communication unit further transmits the encrypted third share to the intermediate device, the second communication unit further receives the encrypted third share from the measurement device, the third communication unit transmits, to the access device, the encrypted vital data, the first share, the encrypted second share, and the encrypted third share received by the second communication unit, the access device includes:

a fifth communication unit configured to receive, from the intermediate device, the encrypted vital data, the first share, the encrypted second share, and the encrypted third share;

a third share decryption unit configured to decrypt the encrypted third share received by the fifth communication unit using the fourth decryption key stored in the access device, to generate the third share; and a sixth communication unit configured to transmit, to the server device, the encrypted vital data, the first share, the encrypted second share received by the fifth communication unit, and the fourth communication unit is configured to receive, from the access unit, the encrypted vital data, the first share, and the encrypted second share.

6. The health care system according to claim 5,
wherein the third share decryption unit is further configured to generate a second encrypted third share by encrypting the generated third share using a fifth encryption key corresponding to the second decryption key stored in the server device, the sixth communication unit is further configured to transmit, to the server device, the second encrypted third share generated by the third share decryption unit, the fourth communication unit is further configured to receive the second encrypted third share from the access device, the share decryption unit is further configured to decrypt the second encrypted third share received by the fourth communication unit using the second decryption key stored in the server device, to generate the third share, and the reconstruction unit is configured to reconstruct the first decryption key for decrypting the encrypted vital data using two shares among (i) the first share received by the fourth communication unit and (ii) the second share and the third share generated by the share decryption unit.

7. The health care system according to claim 1,
wherein the server device further includes:
a holding unit configured to hold the second share; and
a supply unit configured to supply the second share held in the holding unit to another measurement device having the same structure as a structure of the measurement device.

8. The health care system according to claim 1,
wherein the server device further includes:
a holding unit configured to hold the first share; and
a supply unit configured to supply the first share held in the holding unit to another intermediate device having the same structure as a structure of the intermediate device.

9. The health care system according to claim 1,
wherein the server device further includes
a supply unit configured to generate, from the first decryption key reconstructed by the reconstruction unit, a share associated with another measurement device having a same structure as the measurement device, and supply the generated share to the other measurement device, the supplied share being different from the first share and the second share.

10. The health care system according to claim 1,
wherein the server device further includes:
a supply unit configured to generate, from the first decryption key reconstructed by the reconstruction unit, a share associated with another intermediate device having a same structure as the intermediate device, and supply the generated share to the other intermediate device, the supplied share being different from the first share and the second share.

11. The health care system according to claim 3,
wherein the measurement device includes a measurement terminal and a management terminal,
the measurement terminal includes:
the measurement unit;
the vital data encryption unit;
the share generation unit;
the first share encryption unit; and
a transmission unit configured to transmit, to the management terminal, the encrypted vital data, the encrypted first share, and the second share, and the management terminal includes:
a reception unit configured to receive, from the measurement terminal, the encrypted vital data, the encrypted first share, and the second share;
a second share encryption unit; and
a first communication unit, and
the second share encryption unit is configured to encrypt the second share received by the reception unit using a sixth encryption key corresponding to the fifth decryption key stored in the server device, to generate the encrypted second share.

12. The health care system according to claim 1,
wherein each of the first share and the second share is a set of data.

13. A vital data measurement method of measuring vital data, the vital data measurement method comprising:
in a measurement device:
measuring the vital data of a patient;
encrypting the vital data using a first encryption key generated by the measurement device to generate encrypted vital data;
generating a first share and a second share of a first decryption key which is for decrypting the encrypted vital data and generated by the measurement device, and the first share and the second share being two mutually different shares which enable reconstruction of the first decryption key only when both of the two shares are available;
encrypting the second share using a second encryption key corresponding to a second decryption key that is stored in a server device but is not stored in an intermediate device, to generate an encrypted second share; and
transmitting, to the intermediate device, the encrypted vital data, the first share, and the encrypted second share,
the following performed by the intermediate device:
receiving, from the measurement device, the encrypted vital data, the first share, and the encrypted second share; and
transmitting, to the server device, the encrypted vital data, the first share, and the encrypted second share, and
in the server device:
receiving, from the intermediate device, the encrypted vital data, the first share, and the encrypted second share;
decrypting the encrypted second share using the second decryption key stored in the server device, to generate the second share;
reconstructing the first decryption key for decrypting the encrypted vital data, using the first share and the second share; and
decrypting the encrypted vital data using the first decryption key to generate the vital data.

14. A measurement device which measures vital data, comprising:
a measurement unit configured to measure the vital data of a patient;
a vital data encryption unit configured to encrypt the vital data using a first encryption key generated by the measurement device to generate encrypted vital data;
a share generation unit configured to generate a first share and a second share of a first decryption key which is for decrypting the encrypted vital data and generated by the measurement device, and the first share and the second share being two mutually different shares which enable reconstruction of the first decryption key only when both of the two shares are available;
a second share encryption unit configured to generate an encrypted second share by encrypting the second share generated by the share generation unit using a second encryption key corresponding to a second decryption key that is stored in a server device but is not stored in an intermediate device; and
a first communication unit configured to transmit, to the intermediate device, the encrypted vital data generated by the vital data encryption unit, the first share generated by the share generation unit, and the encrypted second share generated by the second share encryption unit.

15. A measurement method of measuring vital data, comprising:
measuring the vital data of a patient;
encrypting the vital data using a first encryption key generated by a measurement device to generate encrypted vital data;
generating a first share and a second share of a first decryption key which is for decrypting the encrypted vital data and generated by the measurement device, and the first share and the second share being two mutually different shares which enable reconstruction of the first decryption key only when both of the two shares are available;
encrypting the generated second share using a second encryption key corresponding to a second decryption key that is stored in a server device but is not stored in an intermediate device, to generate an encrypted second share; and
transmitting, to outside, the encrypted vital data, the first share, and the encrypted second share.

16. A non-transitory computer-readable recording medium having recorded thereon a program for measuring vital data, the program causing a computer to execute steps comprising:
measuring the vital data of a patient;
encrypting the vital data using a first encryption key generated by the computer to generate encrypted vital data;
generating a first share and a second share of a first decryption key which is for decrypting the encrypted vital data and generated by the computer, and the first share and the second share being two mutually different shares which enable reconstruction of the first decryption key only when both of the two shares are available;
encrypting the generated second share using a second encryption key corresponding to a second decryption key that is stored in a server device but is not stored in an intermediate device, to generate an encrypted second share; and
transmitting, to outside, the encrypted vital data, the first share, and the encrypted second share.

17. An integrated circuit which measures vital data, comprising:
a measurement unit configured to measure the vital data of a patient;
a vital data encryption unit configured to encrypt the vital data using a first encryption key generated by the integrated circuit to generate encrypted vital data;
a share generation unit configured to generate a first share and a second share of a first decryption key which is for decrypting the encrypted vital data and generated by the integrated circuit, and the first share and the second share being two mutually different shares which enable reconstruction of the first decryption key only when both of the two shares are available;
a second share encryption unit configured to encrypt the second share generated by the share generation unit using a second encryption key corresponding to a second decryption key that is stored in a server device but is not stored in an intermediate device, to generate an encrypted second share; and a first communication unit configured to transmit, to the intermediate device, the encrypted vital data generated by the vital data encryption unit, the first share generated by the share generation unit, and the encrypted second share generated by the second share encryption unit.

18. An intermediate device which relays vital data measured by a measurement device to a server device, the intermediate device comprising:
    a reception unit configured to receive, from the measurement device, (i) encrypted vital data obtained by encrypting the vital data using an encryption key generated by the measurement device, (ii) a first share that is one of two mutually different shares which enable reconstruction of a decryption key which is for decrypting the encrypted vital data and generated by the measurement device only when both of the two shares are available, and (iii) an encrypted second share obtained by encrypting a second share, which is the other one of the two mutually different shares, using a second encryption key corresponding to a second decryption key that is stored in the server device but not stored in the intermediate device;
    a transmission unit configured to transmit, to the server device, the encrypted vital data, the first share, and the encrypted second share received by the reception unit; and
    a storage unit configured to store only the first share received by the reception unit,
    wherein the reception unit is further configured to receive the second share from the measurement device,
    the intermediate device further comprising:
    an intermediate device side vital data decryption unit configured to reconstruct the decryption key for decrypting the encrypted vital data using the first share stored in the storage unit and the second share received by the reception unit, and to decrypt the encrypted vital data received by the reception unit using the reconstructed decryption key to generate the vital data; and
    a display unit configured to display the vital data generated by the intermediate device side vital data decryption unit.

19. A relay method of relaying vital data measured by a measurement device to a server device via an intermediate device, the relay method comprising:
    receiving, from the measurement device, (i) encrypted vital data obtained by encrypting the vital data using an encryption key generated by the measurement device, (ii) a first share that is one of two mutually different shares which enable reconstruction of a decryption key which is for decrypting the encrypted vital data and generated by the measurement device only when both of the two shares are available, and (iii) an encrypted second share obtained by encrypting a second share, which is the other one of the two mutually different shares, using a second encryption key corresponding to a second decryption key that is stored in the server device but not stored in the intermediate device; and
    transmitting, to the server device, the encrypted vital data, the first share, and the encrypted second share received by the reception unit,
    wherein, in the receiving, the second share is further received from the measurement device,
    the relay method further comprising:
    reconstructing the decryption key for decrypting the encrypted vital data using the first share stored in a storage unit and the received second share, and to decrypt the encrypted vital data received using the reconstructed decryption key to generate the vital data; and
    displaying the generated vital data.

20. A non-transitory computer-readable recording medium having recorded thereon a program for relaying vital data measured by a measurement device to a server device via an intermediate device, the program causing a computer to execute steps comprising:
    receiving, from the measurement device, (i) encrypted vital data obtained by encrypting the vital data using an encryption key generated by the measurement device, (ii) a first share that is one of two mutually different shares which enable reconstruction of a decryption key which is for decrypting the encrypted vital data and generated by the measurement device only when both of the two shares are available, and (iii) an encrypted second share obtained by encrypting a second share, which is the other one of the two mutually different shares, using a second encryption key corresponding to a second decryption key that is stored in the server device but not stored in the intermediate device; and
    transmitting, to the server device, the encrypted vital data, the first share, and the encrypted second share received by the reception unit,
    wherein, in the receiving step, the second share is further received from the measurement device, and
    the program causes the computer to further execute steps including:
    reconstructing the decryption key for decrypting the encrypted vital data using the first share stored in a storage unit and the received second share, and to decrypt the encrypted vital data received using the reconstructed decryption key to generate the vital data; and
    displaying the generated vital data.

21. An integrated circuit which relays vital data measured by a measurement device to a server device via an intermediate device, the integrated circuit comprising:
    a reception unit configured to receive, from the measurement device, (i) encrypted vital data obtained by encrypting the vital data using an encryption key generated by the measurement device, (ii) a first share that is one of two mutually different shares which enable reconstruction of a decryption key which is for decrypting the encrypted vital data and generated by the measurement device only when both of the two shares are available, and (iii) an encrypted second share obtained by encrypting a second share, which is the other one of the two mutually different shares, using a second encryption key corresponding to a second decryption key that is stored in the server device but not stored in the intermediate device;
    a transmission unit configured to transmit, to the server device, the encrypted vital data, the first share, and the encrypted second share received by the reception unit; and
    a storage unit configured to store only the first share received by the reception unit,
    wherein the reception unit is further configured to receive the second share from the measurement device,
    the intermediate device further comprising:
    an intermediate device side vital data decryption unit configured to reconstruct the decryption key for decrypting the encrypted vital data using the first share stored in the storage unit and the second share received by the reception unit, and to decrypt the encrypted vital data received by the reception unit using the reconstructed decryption key to generate the vital data; and a display unit configured to display the vital data generated by the intermediate device side vital data decryption unit.

* * * * *